US010703782B2

(12) United States Patent
Baum et al.

(10) Patent No.: US 10,703,782 B2
(45) Date of Patent: Jul. 7, 2020

(54) PESTICIDAL TOXIN PROTEINS ACTIVE AGAINST LEPIDOPTERAN INSECTS

(71) Applicant: Monsanto Technology LLC, St. Louis, MO (US)

(72) Inventors: James A. Baum, Webster Groves, MO (US); David J. Bowen, Wildwood, MO (US); Catherine A. Chay, Ballwin, MO (US); David J. Chi, Ballwin, MO (US); William P. Clinton, University City, MO (US); Crystal L. Dart, Norton, MA (US); Leigh English, Chesterfield, MO (US); Stanislaw Flasinski, Ballwin, MO (US); Victor M. Guzov, Cambridge, MA (US); Kevin A. Jarrell, Woburn, MA (US); Uma R. Kesanapalli, Chesterfield, MO (US); Thomas M. Malvar, N. Stonington, CT (US); Robert M. McCarroll, Lexington, MA (US); Jason S. Milligan, Troy, IL (US); Jay P. Morgenstern, Cambridge, MA (US); Deborah G. Rucker, St. Louis, MO (US); Sara A. Salvador, Wildwood, MO (US); Temple F. Smith, Woburn, MA (US); Carlos E. Soto, Granite City, IL (US); Collin M. Stultz, Woburn, MA (US); Brian M. Turczyk, Woburn, MA (US); Ty T. Vaughn, Clayton, MO (US); Moritz W. F. Von Rechenberg, Waltham, MA (US)

(73) Assignee: Monsanto Technology LLC, St. Louis, MO (US)

( * ) Notice: Subject to any disclaimer, the term of this patent is extended or adjusted under 35 U.S.C. 154(b) by 152 days.

(21) Appl. No.: 15/868,676

(22) Filed: Jan. 11, 2018

(65) Prior Publication Data

US 2018/0208631 A1 Jul. 26, 2018

Related U.S. Application Data

(60) Provisional application No. 62/445,313, filed on Jan. 12, 2017.

(51) Int. Cl.
*C07K 14/325* (2006.01)
*C12N 15/82* (2006.01)

(52) U.S. Cl.
CPC ........ *C07K 14/325* (2013.01); *C12N 15/8286* (2013.01); *Y02A 40/162* (2018.01)

(58) Field of Classification Search
None
See application file for complete search history.

(56) References Cited

U.S. PATENT DOCUMENTS 7,250,501 B2 * 7/2007 Malvar ................ C07K 14/325 536/23.1
8,697,642 B2 * 4/2014 Lira ..................... C07K 14/325 514/4.5
2012/0035135 A1 2/2012 Andersch et al.
2015/0148288 A1 5/2015 Kennedy et al.
2018/0220656 A1 * 8/2018 Gockel .................. A01N 43/90

FOREIGN PATENT DOCUMENTS

WO WO2015/144652 * 10/2015
WO WO 2017/003811 1/2017

OTHER PUBLICATIONS

De Maagd et al. (1999) Appl Environ Microbiol 65:4369-74.*
Tounsi et al. (2003) J Appl Microbiol 95:23-28.*
Angsuthanasonnbat et al. (2001) J Biochem Mol Biol 34:402-07.*
Aronson & Shai (2001) FEMS Microbiol Lett 195:1-8.*
De Maagd et al. (2001) Trends Genet 17:193-99.*
Guo et al. (2004) Proc Natl Acad Sci USA 101:9205-10.*
Yu et al. (2014) AIW52617.*
Govaerts et al. (2006) Appl Soil Ecol 32:305-15.*
International Search Report and Written Opinion regarding International Application No. PCT/US2018/013298, dated May 8, 2018.

* cited by examiner

*Primary Examiner* — Russell T Boggs
(74) *Attorney, Agent, or Firm* — Dentons US LLP; Timothy Ball; Carine Doyle

(57) ABSTRACT

Disclosed herein are nucleotide sequences encoding an insecticidal protein exhibiting Lepidopteran inhibitory activity, as well as novel insecticidal proteins referred to herein as a BCW 001, BCW 002, BCW 003, and BCW toxic protein-containing chimeras and BCW toxin insecticide, transgenic plants expressing the chimeras or the insecticide, and methods for detecting the presence of the nucleotide sequences or the insecticide in a biological sample.

14 Claims, 3 Drawing Sheets

Specification includes a Sequence Listing.

| Insect Species | BCW 001 | BCW 002 | BCW 003 |
|---|---|---|---|
| A. ipsilon | + | + | + |
| S. albicosta | + | + | + |
| H. zea | + | + | + |
| O. nubilalis | + | + | + |
| D. saccharalis | ND | ND | + |
| D. grandiosella | + | ND | + |
| T. ni | + | ND | + |
| P. includens | + | ND | +

```
SEQ ID NO:2    MEEN-NQNQCVPYNCLNNPAIEILEGDRISVGNTPIDISLSLVELLISEFVPGGGIITGL     59
SEQ ID NO:4    MDNNPNINECIPYNCLSNPEVEVLGGERIETGYTPIDISLSLTQFLLSEFVPGAGFVLGL     60
SEQ ID NO:6    MDNNPNINECIPYNCLSNPEVEVLGGERIETGYTPIDISLSLTQFLLSEFVPGAGFVLGL     60
               **  *  *  *    *  ** *  *  **  *         *** *       * ***

SEQ ID NO:2    LNIVWGFVGPSQWDAFLAQVEQLINQRISEAVRNTAIQELEGMARVYRTYATAFAEWERD    119
SEQ ID NO:4    VDIIWGIFGPSQWDAFLVQIEQLINQRIEEFARNQAISRLEGLSNLYQIYAESFREWEAD    120
SEQ ID NO:6    VDIIWGIFGPSQWDAFLVQIEQLINQRIEEFARNQAISRLEGLSNLYQIYAESFREWEAD    120
                 ** *  **        * *          * **   *  **   **** **  ** *    *

SEQ ID NO:2    PNNTDLREAVRTQFTATETYISGRISVLKIQNFEVQLLSVFAQAANLHLSLLRDVVFFGQ    179
SEQ ID NO:4    PTNPALREEMRIQFNDMNSALTTAIPLLAVQNYQVPLLSVYVQAANLHLSVLRDVSVFGQ    180
SEQ ID NO:6    PTNPALREEMRIQFNDMNSALTTAIPLLAVQNYQVPLLSVYVQAANLHLSVLRDVSVFGQ    180
                * **     ** *   **********  ** **    ** *      **     *   **

SEQ ID NO:2    RWGFSTTTVNNYYNDLTEEISTYTDYAVRWYNTGLERVWGPDSRDWVRYNQFRRELTLTV    239
SEQ ID NO:4    RWGFDAATINSRYNDLTRLIGNYTDYAVRWYNTGLERVWGPDSRDWVRYNQFRRELTLTV    240
SEQ ID NO:6    RWGFDAATINSRYNDLTRLIGNYTDYAVRWYNTGLERVWGPDSRDWVRYNQFRRELTLTV    240
                   *** *  **      ** **

SEQ ID NO:2    LDIVALFPNYDSRRYPIRTVSQLTREIYTNPVLENFDGSFRGMAQRIEQNIRQPHLMDIL    299
SEQ ID NO:4    LDIVALFPNYDSRRYPIRIVSQLTREIYTNPVLENFDGSFRGMAQRIEQNIRQPHLMDIL    300
SEQ ID NO:6    LDIVALFPNYDSRRYPIRTVSQLTREIYTNPVLENFDGSFRGMAQRIEQNIRQPHLMDIL    300
                                 *

SEQ ID NO:2    NSITIYTDVHRGFNYWSGHQITASPVGFSGPEFAFPLFGNAGNAAPPVLVSLTGLGIFRT    359
SEQ ID NO:4    NSITIYTDVHRGFNYWSGHQITASPVGFSGPEFAFPLFGNAGNAAPPVLVSLTGLGIFRT    360
SEQ ID NO:6    NSITIYTDVHRGFNYWSGHQITASPVGFSGPEFAFPLFGNAGNAAPPVLVSLTGLGIFRT    360

SEQ ID NO:2    LSSPLYRRIILGSGPNNQELFVLDGTEFSFASLTTNLPSTIYRQRGTVDSLDVIPPQDNS    419
SEQ ID NO:4    LSSPLYRRIILGSGPNNQELFVLDGTEFSFASLTTNLPSTIYRQRGTVDSLDVIPPQDNS    420
SEQ ID NO:6    LSSPLYRRIILGSGPNNQELFVLDGTEFSFASLTTNLPSTIYRQRGTVDSLDVIPPQDNS    420

SEQ ID NO:2    VPPRAGFSHRLSHVTMLSQAAGAVYTLRAPTFSWQHRSATTTNIIAADSITQIPAVKGRS    479
SEQ ID NO:4    VPPRAGFSHRLSHVTMLSQAAGAVYTLRAPTFSWQHRSATTTNIIAADSITQIPAVKGRS    480
SEQ ID NO:6    VPPRAGFSHRLSHVTMLSQAAGAVYTLRAPTFSWQHRSATTTNIIAADSITQIPAVKGRS    480

SEQ ID NO:2    IINNGTVISGPGFTGGDLVRLYNADFNINNRAYLEVPIFFQSPSTNYRVRVRYASTSSLP    539
SEQ ID NO:4    IINNGTVISGPGFTGGDLVRLYNADFNINNRAYLEVPIFFQSPSTNYRVRVRYASTSSLP    540
SEQ ID NO:6    IINNGTVISGPGFTGGDLVRLYNADFNINNRAYLEVPIFFQSPSTNYRVRVRYASTSSLP    540

SEQ ID NO:2    VDVVFGNISHPTTFPATARSLDNLQSNDFGYIDIAGTFLPSLGPSIGIRPMLSTINLIVD    599
SEQ ID NO:4    VDVVFGNISHPTTFPATARSLDNLQSNDFGYIDIAGTFLPSLGPSIGIRPMLSTINLIVD    600
SEQ ID NO:6    VDVVFGNISHPTTFPATARSLDNLQSNDFGYIDIAGTFLPSLGPSIGIRPMLSTINLIVD    600

SEQ ID NO:2    RFEFIPVTATFEAESDLERAQKAVNALFTSTNQLGIKTDVTDYHIDQVSNLVECLSDEFY    659
SEQ ID NO:4    RFEFIPVTATFEAESDLERAQKAVNALFTSTNQLGIKTDVTDYHIDQVSNLVECLSDEFY    660
SEQ ID NO:6    RFEFIPVTATFEAESDLERAQKAVNALFTSTNQLGIKTDVTDYHIDQVSNLVECLSDEFY    660
```

FIGURE 2

```
SEQ ID NO:2    LDEKRELSEKVKHAKRLSDERNLLQDPNFRGINRQPDRGWRGSTDITIQGGDDVFKENYV    719
SEQ ID NO:4    LDEKRELSEKVKHAKRLSDERNLLQDPNFRGINRQPDRGWRGSTDITIQGGDDVFKENYV    720
SEQ ID NO:6    LDEKRELSEKVKHAKRLSDERNLLQDPNFRGINRQPDRGWRGSTDITIQGGDDVFKENYV    720

SEQ ID NO:2    TLPGTFDECYPTYLYQKIDESKLKAYTRYQLRGYIEDSQDLEIYLIRYNAKHETVNVPGT    779
SEQ ID NO:4    TLPGTFDECYPTYLYQKIDESKLKAFTRYQLRGYIEDSQDLEIYLIRYNAKHETVNVPGT    780
SEQ ID NO:6    TLPGTFDECYPTYLYQKIDESKLKAFTRYQLRGYIEDSQDLEIYLIRYNAKHETVNVPGT    780
                                       *

SEQ ID NO:2    GSLWPLSAQSPIGKCGEPNRCAPHLEWNPDLHCSCRDGEKCAHHSHHFSLDIDVGCTDLN    839
SEQ ID NO:4    GSLWPLSAQSPIGKCGEPNRCAPHLEWNPDLDCSCRDGEKCAHHSHHFSLDIDVGCTDLN    840
SEQ ID NO:6    GSLWPLSAQSPIGKCGEPNRCAPHLEWNPDLDCSCRDGEKCAHHSHHFSLDIDVGCTDLN    840
                                              *

SEQ ID NO:2    EDLGVWVIFKIKTQDGHARLGNLEFLEEKPLVGEALARVKRAEKKWRDKREKLQLETNIV    899
SEQ ID NO:4    EDLGVWVIFKIKTQDGHARLGNLEFLEEKPLVGEALARVKRAEKKWRDKREKLEWETNIV    900
SEQ ID NO:6    EDLGVWVIFKIKTQDGHARLGNLEFLEEKPLVGEALARVKRAEKKWRDKREKLEWETNIV    900
                                                                   **

SEQ ID NO:2    YKEAKESVDALFVNSQYDQLQADTNIAMIHAADKRVHRIREAYLPELSVIPGVNADISEE    959
SEQ ID NO:4    YKEAKESVDALFVNSQYDQLQADTNIAMIHAADKRVHSIREAYLPELSVIPGVNAAIFEE    960
SEQ ID NO:6    YKEAKESVDALFVNSQYDQLQADTNIAMIHAADKRVHSIREAYLPELSVIPGVNAAIFEE    960
                                                *                   * *

SEQ ID NO:2    LEGRIFTAFSLYDARNVIKNGDFNNGLLCWNVKGHVDVEEQNNHRSVLVVPEWEAEVSQE    1019
SEQ ID NO:4    LEGRIFTAFSLYDARNVIKNGDFNNGLSCWNVKGHVDVEEQNNQRSVLVVPEWEAEVSQE    1020
SEQ ID NO:6    LEGRIFTAFSLYDARNVIKNGDFNNGLSCWNVKGHVDVEEQNNQRSVLVVPEWEAEVSQE    1020
                                          *               *

SEQ ID NO:2    VRVCPGRGYILRVTAYKEGYGEGCVTIHEIENNTDELKFSNCVEEEVYPNNTVTCNDYTA    1079
SEQ ID NO:4    VRVCPGRGYILRVTAYKEGYGEGCVTIHEIENNTDELKFSNCVEEEIYPNNTVTCNDYTV    1080
SEQ ID NO:6    VRVCPGRGYILRVTAYKEGYGEGCVTIHEIENNTDELKFSNCVEEEIYPNNTVTCNDYTV    1080
                                                             *                *

SEQ ID NO:2    NQEEYEGTYTSRNRGYDEAYESNSSVPAEYASVYEEKVYTDGRRGNPCESNRGYGDYTPL    1139
SEQ ID NO:4    NQEEYGGAYTSRNRGYNEAP----SVPADYASVYEEKSYTDGRRENPCEFNRGYRDYTPL    1136
SEQ ID NO:6    NQEEYGGAYTSRNRGYNEAP----SVPADYASVYEEKSYTDGRRENPCEFNRGYRDYTPL    1136
                    * *         *  *****     *    *         *      *    *

SEQ ID NO:2    PAGYVTKELEYFPETDKVWIEIGETEGTFIVDSVELLLMEE    1180
SEQ ID NO:4    PVGYVTKELEYFPETDKVWIEIGETEGTFIVDSVELLLMEE    1177
SEQ ID NO:6    PVGYVTKELEYFPETDKVWIEIGETEGTFIVDSVELLLMEE    1177
                *
```

FIGURE 2 (continued)

PESTICIDAL TOXIN PROTEINS ACTIVE AGAINST LEPIDOPTERAN INSECTS

REFERENCE TO RELATED APPLICATION

This application claims the benefit of U.S. Provisional Application No. 62/445,313, filed Jan. 12, 2017, which is herein incorporated by reference in its entirety.

INCORPORATION OF SEQUENCE LISTING

A computer readable form of the sequence listing is provided herein, containing the file named "MONS434US-sequence listing.txt" was created on Jan. 11, 2018. This file is 166,134 bytes as measured in MS-Windows®, and is herein incorporated by reference in its entirety. This sequence listing consists of SEQ ID NO:1-SEQ IDNO:12.

FIELD OF THE INVENTION

The invention relates generally to the field of insect inhibitory proteins, in particular to proteins exhibiting insect inhibitory activity against agriculturally relevant Lepidopteran pests of plants and seeds, particularly Lepidopteran pests such as black cutworm ("BCW", *Agrotis ipsilon*).

BACKGROUND OF THE INVENTION

Insect inhibitory proteins produced by *Bacillus thuringiensis* (Bt) bacterial species are known in the art. Certain Bt proteins can be used to control agricultural pests of crop plants by spraying agriculturally acceptable formulations containing one or more such proteins onto plants, coating seeds with a composition formulated to contain an insecticidally effective amount of such proteins, or by expressing the result effective one or more proteins in plants/seeds.

Only a few Bt proteins have been developed for use as transgenic traits for commercial use by farmers to control insect pests. Farmers rely on these proteins to provide a prescribed spectrum of pest control, and may continue to rely on broad spectrum chemistries in foliar and soil applications to control pests. Certain Lepidopteran insects, such as *Agrotis* species and *Striacosta* species, have proven to be particularly difficult to control using transgenic insecticidal traits currently in use including Cry1Ab, Cry1Ac, Cry1Fa, Cry2Ab, Cry2Ae, VIP3Aa, and various other Bt toxins that have been used less frequently. Hence, there is a need for insect inhibitory proteins that exhibit activity against a broader spectrum of insect pest species, and for use in toxins for use in overcoming resistance development of pests to existing pesticides, including toxins used currently in pest management systems.

This application describes a novel protein family, variants, and chimeric toxin protein constructs that each exhibit surprisingly efficacious insecticidal activity against Lepidoptera, particularly against *Agrotis* species pests, such as black cutworm.

BRIEF SUMMARY OF THE INVENTION

A novel group of insect inhibitory polypeptides (toxin proteins BCW 001, BCW 002 and BCW 003 and pesticidal fragments thereof) are shown to exhibit inhibitory activity against several Lepidopteran pests of crop plants, particularly against black cutworm species (*Agrotis* species). Each of the proteins can be used alone or in combination with each other and with other Bt proteins and insect inhibitory agents in formulations and in planta, thus providing alternatives to Bt proteins and insecticide chemistries currently in use in agricultural systems.

The present invention provides polynucleotide constructs that contain, in operable linkage, a heterologous promoter segment linked to a nucleotide sequence encoding an insecticidal protein having Cry1A characteristics that is less than full length relative to a Cry1A class toxin protein, and that has the amino acid sequence from about position 1 through position 607 as set forth in SEQ ID NO:2, SEQ ID NO:4, SEQ ID NO 6, SEQ ID NO:8, SEQ ID NO:10, and SEQ ID NO:12, or an insecticidally active fragment thereof. The less than full length polypeptide that exhibits such insecticidal activity should exhibit at least about 100%, 99%, 98%, 97%, 96%, 95%, 94%, 94%, 92%, 91%, or 90% identity to the BCW 001 amino acid sequence as set forth in SEQ ID NO:2 from about position 1 through about position 606, or from about position 5 through about position 600. If full length or considerably larger toxin fragments are to be used, the percent identity should be less stringent and extend to percent identity from about 100, to about 95, to about 90, to about 85, or even 80% identity to the full length toxin protein sequences as set forth in SEQ ID NO:2, 4, and 6, as these toxin proteins exhibit commercially useful levels of bioactivity when tested against black cutworm larvae in diet bioassays, and when tested in planta in corn, cotton and in soybean transgenic events expressing such proteins.

The invention also provides proteins toxic to black cutworm Lepidopteran species, including proteins having the amino acid sequence as set forth in SEQ ID NO:2 from position 256 to 606 (a BCW 001 protein), and proteins having the amino acid sequence as set forth in either of SEQ ID NO:4 and SEQ ID NO:6 from amino acid position 257 to 607 (referred to respectively herein as a BCW 002 toxin protein and a BCW 003 toxin protein).

Such insecticidal proteins also are observed to exhibit activity against Lepidopteran species selected from the group consisting of *Spodoptera frugiperda, Spodoptera exigua, Spodoptera litura, Mamestra configurata, Striacosta albicosta, Trichoplusia ni, Pseudoplusia includens, Anticarsia gemmatalis, Hypena scabra, Heliothis virescens, Agrotis subterranea, Pseudaletia unipuncta, Agrotis ipsilon, Agrotis orthogonia, Ostrinia nubilalis, Amyelois transitella, Crambus caliginosellus, Herpetogramma licarsisalis, Homoeosoma electellum, Elasmopalpus lignosellus, Cydia pomonella, Endopiza viteana, Grapholita molesta, Suleima helianthana, Plutella xylostella, Pectinophora gossypiella, Lymantria dispar, Alabama argillacea, Archips argyrospila, Archips rosana, Chilo suppressalis, Cnaphalocrocis medinalis, Crambus caliginosellus, Crambus teterrellus, Diatraea grandiosella, Diatraea saccharalis, Earias insulana, Egrias vittella, Helicoverpa armigera, Helicoverpa zea, Heliothis virescens, Herpetogramma licarsisalis, Lobesia botrana, Pectinophora gossypiella, Phyllocnistis citrella, Pieris brassicae, Pieris rapae, Plutella xylostella,* and *Tuta absoluta*.

The proteins of the present invention also may exhibit bioactivity against Lepidopteran species selected from the group consisting of *Spodoptera frugiperda, Spodoptera exigua, Spodoptera litura, Mamestra configurata, Striacosta albicosta, Trichoplusia ni, Pseudoplusia includens, Anticarsia gemmatalis, Hypena scabra, Heliothis virescens, Agrotis subterranea, Pseudaletia unipuncta, Agrotis ipsilon, Agrotis orthogonia, Ostrinia nubilalis, Amyelois transitella, Crambus caliginosellus, Herpetogramma licarsisalis, Homoeosoma electellum, Elasmopalpus lignosellus, Cydia pomonella, Endopiza viteana, Grapholita molesta, Suleima* helianthana, Plutella xylostella, Pectinophora gossypiella, Lymantria dispar, Alabama argillacea, Archips argyrospila, Archips rosana, Chilo suppressalis, Cnaphalocrocis medinalis, Crambus caliginosellus, Crambus teterrellus, Diatraea grandiosella, Diatraea saccharalis, Earias insulana, Egrias vittella, Helicoverpa armigera, Helicoverpa zea, Heliothis virescens, Herpetogramma licarsisalis, Lobesia botrana, Pectinophora gossypiella, Phyllocnistis citrella, Pieris brassicae, Pieris rapae, Plutella xylostella, and Tuta absoluta.

The proteins of the present invention, and the constructs contemplated herein, may be included in any vector including plasmids, cosmids, bacmids, phage mediated vectors, and the like.

Such vectors may be used to introduce the constructs of the present invention into any number of host cells, including into bacterial cells, yeast cells, and plant cells.

Host cells that are yeast cells may be *Saccharomyces cereviseae* or *Saccharomyces pombe* and the like. Bacterial host cells may be any number of known such host cells including but not limited to *E. coli, B. thuringiensis*, and other related bacilli. Plant host cells may be obtained from any number of plant species, including but not limited to plant cells from alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plants.

Transgenic plant events may be produced, particularly corn, cotton and soybean transgenic plant varieties, by introducing the constructs of the present invention containing the appropriately modified polynucleotide sequences such as set forth in SEQ ID NO:7, SEQ ID NO:9, and SEQ ID NO:11, for example, into the genome of such plant cells and recovering a fertile transgenic maize, soy or cotton plant comprising in its genome a genetic construct for expressing at least a protein toxin of the present invention, i.e., a BCW 001, BCW 002, or a BCW 003 protein toxin. Such transgenic plants will have introduced into their plant genome, a polynucleotide construct comprising at least a heterologous promoter segment operably linked to a nucleotide sequence encoding an BCW 001, BCW 002, or BCW 003 insecticidal protein having the amino acid sequence selected from the group consisting of SEQ ID NO:8, SEQ ID NO:10, and SEQ ID NO: 12, or an insecticidal protein fragment thereof.

Seeds are also contemplated as a feature of the invention, in which seed are produced from such transgenic plants and such seed contain a detectable amount of the polynucleotide construct introduced into the plant genome. Pollen, seed, progeny plant cells, plant tissue and commodity products produced from each such transgenic plant will contain a detectable amount of the polynucleotide construct.

Any biological sample that contains at least a detectable amount of the polynucleotide construct encoding such BCW 001, BCW 002, or BCW 003 protein will be within the scope of the invention.

Compositions that provide an insecticidally effective amount of the BCW 001, 002 or 003 protein of the present invention are contemplated, and are provided for controlling Lepidopteran pest species. Such compositions may also contain a supplemental agent that is different from the BCW toxin protein. Such agent will also be toxic to the same Lepidopteran species as the BCW toxin protein. The supplemental agent is to be selected from the group of agents consisting of proteins or polypeptides that have an amino acid sequence that is different from the BCW protein, and can also be an agent that is a RNA molecule conferring toxic effects upon the target insect pest (such as a dsRNA, a miRNA, or an siRNA), and can also be an insecticidal chemical compound such as a pyrethrin, an organophosphate pesticide, and the like. Alternatively the supplemental agent can be any compatible Cry or related toxin protein such as another Cry1A, Cry1Ab, Cry1Ac, Cry1A.105, Cry1Ae, (but these are not preferable as these may not confer appropriate resistance management properties), or Cry1B, Cry1C, Cry1D, Cry1E, Cry1F, Cry1G, Cry1H, Cry1I, Cry1J, Cry1K, Cry1L, Cry2A, Cry2Ab, Cry2Ae, Cry4B, Cry6, Cry7, Cry8, Cry9, Cry15, Cry43A, Cry43B, ET35, ET66, TIC400, TIC800, TIC807, TIC834, TIC853, TIC1415, VIP3A, VIP3Ab, Axmi insecticidal proteins, DIG insecticidal proteins, eHIPs, and VIP proteins and any toxin protein known in the art to confer toxic properties upon the Black Cutworm species larvae or applicable other Lepidopteran target pest species.

Such compositions may also include additional pesticidal agents that are not necessarily toxic to the same target pest, such as additional agents selected from the group consisting of a Cry1C, a Cry3A, a Cry3B, a Cry34, a Cry35, Cry51Aa1, ET29, ET33, ET34, ET70, TIC407, TIC417, TIC431, TIC901, TIC1201, TIC3131, 5307, DIG-10, Axmi184, Axmi205 and AxmiR1.

Methods are also contemplated for producing seed which take advantage of the pesticidal properties of the proteins of the present invention. Such methods include a polynucleotide construct designed for expression of a BCW 001, BCW 002 or BCW 003 protein, or a protein exhibiting at least about 90% identity to said protein, said method comprising planting one or more seed that contain a polynucleotide expressing one or more of the BCW protein toxins of the present invention, growing plants from such seed and then harvesting a crop of such seed from plants. The harvested seed will contain the polynucleotide construct and will give rise to plants that will also be resistant to black cutworm pest infestation.

Such plants can be corn, cotton, soy or any other plants susceptible to Lepidopteran pest species that are demonstrated to be controlled by the proteins of the present invention. Such plants are contemplated to be previously produced transgenic plants that would benefit from the effects of the toxic properties of the proteins of the present invention. Corn plants that fall into this category include but are not limited to transgenic events selected from the group consisting of DKB89614-9, MON801, MON802, MON809, MON810, MON863, MON88017, MON89034, event 4114-3, event 5307, DAS59122-7, Bt10, Bt11, Bt176, CBH-351, DKB-83614-9, MIR162, MIR604, TC1507, TC6275, event 676, event 678, event 680, event 98140, DAS40278-9, DKB89790-5, MON21-9, HCEM485, MON832, MON87427, NK603, T14, T25 and VCO01981-5. Soybean plants that fall into this category of transgenic plants are selected from the group consisting of MON87751, DAS81419-2, MON87701, A2704-12, A2704-21, A5547-127, A5547-35, CV127, DAS44406-6, DAS68416-4, DP356043, FG72, MON4032, ACS-GM003-1, MON87705, MON87708, MON89788, W62, W98 and GFM Cry1A. Cotton transgenic plants that fall into this category are selected from the group consisting of DAS24236-5, DAS21023-5, event 31707, event 31803, event 31807, event 31808, event 42317, BNLA-601, COT102, COT67B, event 1, GHB119, GK12, MON15985, MLS9124, MON1076, MON531, MON757, T303-3, T304-40, SGK321, event 19-51a, GHB614, LLCotton25, MON88701, MON88702, MON1445, MON1698 and MON88913. Sugarcane transgenic plants that fall into this category include the sugarcane plant transgenic event NXI-1T. Rice plants are known in the art that would benefit from having a construct encoding such BCW protein toxins include rice plant transgenic events selected from the group consisting of LLRICE06, LLRICE601, LLRICE62, GM-A17054 and GM-A17054.

Further, processed plant products are provided that comprise a detectable amount of the disclosed recombinant polynucleotides. Such processed products include, but are not limited to: plant biomass, oil, meal, animal feed, flour, flakes, bran, lint, hulls, and processed seed.

Methods of making transgenic plants are also provided. Such methods include introducing the recombinant polynucleotide into a plant cell and selecting a transgenic plant that expresses an insect inhibitory amount of the recombinant polypeptide encoded by the recombinant polynucleotide.

Other embodiments, features, and advantages of the invention will be apparent from the following detailed description, examples, and claims.

BRIEF DESCRIPTION OF THE DRAWINGS

FIG. 1 shows a list of Lepidopteran insect pest species that were tested in bioassays with BCW 001, BCW 002, and BCW 003 toxin proteins. "+" indicates mortality relative to buffer control; "−" indicates no significant observed mortality above level of buffer control; "ND" indicates not tested using the applicable toxin protein. BCW 001 exhibited mortality against *Agrotis ipsilon* (Black Cutworm), *Striacosta albicostsa* (Western Bean Cutworm), *Helicoverpa zea* (Corn Earworm), *Ostrinia nubilalis* (European Corn Borer), *Diatraea grandiosella* (Southwestern Corn Borer), *Trichoplusia ni* (Cabbage Looper), *Pseudoplusia includens* (Soybean Looper), and did not exhibit mortality or stunting when tested against *Spodoptera frugiperda* (Fall Armyworm). *Diatraea saccharalis* (Sugarcane Borer) was not tested with BCW 001. BCW 002 exhibited mortality against *Agrotis ipsilon* (Black Cutworm), *Striacosta albicostsa* (Western Bean Cutworm), *Helicoverpa zea* (Corn Earworm), and *Ostrinia nubilalis* (European Corn Borer), and did not exhibit mortality or stunting when tested against *Spodoptera frugiperda* (Fall Armyworm). *Diatraea saccharalis* (Sugarcane Borer), *Diatraea grandiosella* (Southwestern Corn Borer), *Trichoplusia ni* (Cabbage Looper), and *Pseudoplusia includens* (Soybean Looper) were not tested with BCW 002. BCW 003 exhibited mortality against *Agrotis ipsilon* (Black Cutworm), *Striacosta albicostsa* (Western Bean Cutworm), *Helicoverpa zea* (Corn Earworm), *Ostrinia nubilalis* (European Corn Borer), *Diatraea saccharalis* (Sugarcane Borer), *Diatraea grandiosella* (Southwestern Corn Borer), *Trichoplusia ni* (Cabbage Looper), and *Pseudoplusia includens* (Soybean Looper), and did not exhibit mortality or stunting when tested against *Spodoptera frugiperda* (Fall Armyworm).

FIG. 2 shows an amino acid sequence alignment of BCW 001 (SEQ ID NO:2, top line) vs BCW 002 (SEQ ID NO:4, middle line), vs BCW 003 (SEQ ID NO:6, bottom line); asterisks below each triplet line represents differences at the applicable amino acid position in at least one of the three different sequences.

BRIEF DESCRIPTION OF THE SEQUENCES

SEQ ID NO:1 is a native *B. thuringiensis* strain EG4384 nucleotide sequence encoding BCW 001 Lepidopteran toxic protein.

SEQ ID NO:2 is the deduced amino acid sequence of BCW 001 from the open reading frame as set forth in SEQ ID NO:1.

SEQ ID NO:3 is an artificial sequence encoding a chimeric BCW 002 Lepidopteran toxic protein.

SEQ ID NO:4 is the deduced amino acid sequence of BCW 002 from the open reading frame as set forth in SEQ ID NO:3, in which such BCW 002 protein consists of domain I of a Cry1Ac operably linked to domains II and III of BCW 001 (amino acid position 258 through amino acid position 606 as set forth in SEQ ID NO:2) and operably linked to a Cry1Ac protoxin domain from amino acid position 608 through 1177 as set forth in SEQ ID NO:4 and SEQ ID NO:6. SEQ ID NO:4 (BCW 002) is different from SEQ ID NO:6 (BCW 003) only at position 259, BCW 002 containing an Isoleucine at this position, BCW 003 containing a Threonine as in BCW 001.

SEQ ID NO:5 is an artificial sequence encoding a chimeric BCW 003 Lepidopteran toxic protein.

SEQ ID NO:6 is the deduced amino acid sequence of BCW 003 from the open reading frame as set forth in SEQ ID NO:3, in which such BCW 003 protein consists of domain I of a Cry1Ac operably linked to domains II and III of BCW 001 (amino acid position 258 through amino acid position 606 as set forth in SEQ ID NO:2) and operably linked to a Cry1Ac protoxin domain from amino acid position 608 through 1177 as set forth in SEQ ID NO:4 and SEQ ID NO:6. SEQ ID NO:6 (BCW 003) is different from SEQ ID NO:4 (BCW 002) only at position 259, BCW 002 containing an Isoleucine at this position, BCW 003 containing a Threonine as in BCW 001.

SEQ ID NO:7 is an artificial sequence encoding a BCW 001 protein for expression in plants.

SEQ ID NO:8 is the deduced amino acid sequence of BCW 001 derived from SEQ ID NO:7.

SEQ ID NO:9 is an artificial sequence encoding a BCW 002 protein for expression in plants.

SEQ ID NO: 10 is the deduced amino acid sequence of BCW 002 derived from SEQ ID NO:9.

SEQ ID NO:11 is an artificial sequence encoding a BCW 003 protein for expression in plants.

SEQ ID NO:12 is the deduced amino acid sequence of BCW 003 derived from SEQ ID NO:11.

DETAILED DESCRIPTION OF THE INVENTION

An alternative to controlling agricultural pests of crop plants by spraying formulations containing insecticidal proteins onto plants/seeds is to insert the polynucleotides encoding these proteins into the plant genome for expression in the plant or plant parts. The plants transformed with these polynucleotides carry insect resistance that these expressed proteins provide as transgenic traits.

In order to avoid the development of, or circumvent insect resistance against currently used proteins, new proteins with different mode-of-action (MOA), as well as a broad spectrum and efficacy are needed for Lepidoptera control. One way to address this need is to sequence Bt genomes in hopes to discover new insecticidal proteins. Another approach is to interchange segments from various Bt proteins to create new chimeric Bt proteins having insect inhibitory properties. The likelihood of arbitrarily creating a chimeric protein with enhanced properties from the reassortment of the domain structures of numerous native insecticidal crystal proteins known in the art is remote (See, e.g. A Strategy for Shuffling Numerous *Bacillus thuringiensis* Crystal Protein Domains; J. Economic Entomology, 97 (6): 1805-1813. 2004).

Disclosed herein are nucleotide sequences that encode insecticidal proteins, identified herein as BCW proteins, which address the need for an alternative MOA, provide activity against a broader spectrum of insect pests, and work for delaying or avoiding the development of resistance, particularly for use in controlling Black Cutworm (BCW) pests.

BCW 001 was discovered as an open reading frame predicting an amino acid sequence having characteristics of a Cry1A type protein after sequencing the genome of *Bacillus thuringiensis* strain EG4384. The BCW 001 open reading frame (ORF) encoded a protein of 1180 amino acids and the protein was predicted to have many of the characteristics of Cry1 protein toxins, including an identifiable domain I, II, and III structure, and a characteristic Cry1A type protoxin domain at the carboxy terminal half of the predicted protein. The predicted Domain I amino acid sequence (residues 1 through about 258 of SEQ ID NO:2) exhibits about 67% identity to Cry1Ac protein toxin domain I. The predicted Domain II amino acid sequence (residues from about 259 through about residue 459 as set forth in SEQ ID NO:2) exhibits perfect (100%) identity to a Cry1Ai2 Domain II. The predicted Domain III amino acid sequence (residues from about 260 through about 606 as set forth in SEQ ID NO:2) exhibits about 63% identity to the corresponding Domain III residues in Cry1Ah2. The protoxin domain structure of the BCW 001 predicted protein (about residues 607 through 1180 as set forth in SEQ ID NO:2) exhibits about 96% identity to the corresponding residues in Cry1Aa9. Overall this predicted full length protein exhibits about 83% amino acid sequence identity to a Cry1Ai, and the predicted toxin region from amino acid positions 1 through about residue 607 as set forth in SEQ ID NO:2 exhibits 76% identity to a Cry1Ai1. It is difficult to assign this new toxin protein to a particular Cry1A class and so the *Bacillus thuringiensis* nomenclature committee will be provided with this sequence and will establish whether this protein merits its own separate and novel class.

The BCW 001 protein was produced from a plasmid vector in an acrystalliferous strain of *Bacillus thuringiensis* and spore crystal preps were tested against a variety of Lepidopteran pests. See FIG. 1, column 2 for the data. The evidence indicated that this protein was uncharacteristic of any of the proteins from which it derives its source of origin, i.e., the Cry1Aa, Cry1Ah, or Cry1Ai toxin proteins known in the art. None of the prior art proteins exhibit any appreciable activity when tested against Black Cutworms, however, this new protein BCW 001 was toxic in bioassays when tested against Black Cutworms, and surprisingly exhibited toxic properties when tested against a battery of other Lepidopteran pests as well as set forth in FIG. 1.

Particularly, in bioassays compared to an untreated insect diet control, BCW 001 protein exhibited activity against western bean cutworm ("WBC", *Striacosta albicosta*), corn earworm ("CEW", *Helicoverpa zea*), European corn borer ("ECB", *Ostrinia nubilalis*), southwestern corn borer ("SWC", *Diatraea grandiosella*), soybean looper ("SL", *Pseudoplusia* includes), cabbage looper ("CLW", *Trichoplusia ni*), and $1^{st}$ and $3^{rd}$ instar black cutworm ("BCW", *Agrotis ipsilon*).

As described further below, chimeric toxin proteins were produced using Domain I of Cry1Ac and Domain II and III of BCW 001 (i.e., BCW 002 and BCW 003 as set forth in SEQ ID NO:4 and SEQ ID NO:6 respectively), and these chimeric toxin proteins were introduced into corn and sugarcane plants. Both chimeric proteins exhibited activity in corn against BCW, WBC, CEW, and SWC. BCW 003 exhibited activity against SCB in sugarcane.

The phrase "BCW protein", as used herein, refers to any novel insect inhibitory protein that comprises, that consisted of, that is substantially homologous to, or that is derived from any insect inhibitory polypeptide sequence of: BCW 001 (SEQ ID NO:2), BCW 002 (SEQ ID NO:4), and BCW 003 (SEQ ID NO:6), and insect inhibitory segments thereof, or combinations thereof, that confer activity against Lepidoptera, in particular, but not limited to, BCW, WBC and/or SCB. A polynucleotide encoding BCW 001 was derived from strain EG4384. The core toxic amino acid sequence for BCW 001 corresponds to amino acids from about position 28 to about position 606 and through position 618 as set forth in SEQ ID NO:2, and the core toxic amino acid sequence for BCW 002 and 003 corresponds to amino acids from about position 29 to about position 607 and through about position 619 as set forth in SEQ ID NO:4 and SEQ ID NO:6, respectively.

In one embodiment, the proteins disclosed herein are related by a primary delta-endotoxin structure, by length (about 1176-1180 amino acids), by the length of the protein without the protoxin (from about 600 to about 619 amino acids), by the length of the toxic core (about 591 amino acids), or by the presence of at least one BCW-specific segment.

Exemplary proteins were aligned with each other using Clustal W algorithm, resulting in a pair-wise number of amino acid identities and a pair-wise percent amino acid identity for each pair using these default parameters: Weight matrix: blosum; Gap opening penalty: 10.0; Gap extension penalty: 0.05; Hydrophilic gaps: On; Hydrophilic residues: GPSNDQERK; Residue-specific gap penalties: On. The Clustal W algorithm is described in Thompson, J. D., Higgins, D. G. and Gibson, T. J. (1994) "CLUSTAL W: improving the sensitivity of progressive multiple sequence alignment through sequence weighting, positions-specific gap penalties and weight matrix choice." Nucleic Acids Research, 22:4673-4680.

Other alignment algorithms are also available in the art and provide results similar to those obtained using a Clustal W alignment.

The term "about" is used herein to describe that these segment boundaries can vary by 1, 2, 3, 4, 5, 10, 20, 25, 30, or 35 residues, depending on the sequence of the parent proteins and their alignment to each other. To further describe the variability and configuration of the various segments, Tables 2 and 3 tabulate the segment boundaries of BCW 002 and 003 and other black cutworm active chimeras.

The term "fragment" is used herein to describe consecutive amino acid or nucleic acid sequences that are shorter than the complete amino acid or nucleic acid sequence describing a BCW toxic protein.

The phrase "insect inhibitory" and "insecticidal" are used herein interchangeably and refer to a protein, protein fragment, protein segment or polynucleotide that results in any measurable inhibition of insect viability, growth, insect development, insect reproduction, insect feeding behavior, insect mating behavior and/or any measurable decrease in the adverse effects caused by an insect feeding on this protein, protein fragment, protein segment or polynucleotide.

The terms "bioactivity", "active", "activity", "effective", "efficacious" or variations thereof are used herein interchangeably to describe the effects of proteins of the present invention on target insect pests.

A crop is a volunteered or cultivated plant whose product is harvested at some point of its growth stage. Non-limiting examples of such products are a seed, a boll, a leaf, a flower, a stem, a root, or any portion thereof.

A biological sample obtained from any tissue of a plant, bacteria, virus or vector comprising a polynucleotide or expressing a protein as exemplified herein, such as, but not limited to, a seed, a boll, a leaf, a flower, a stem, a root, or any portion thereof and containing a detectable amount of the polynucleotide, protein, or both.

The phrase "detectable amount" is used herein to describe the minimal amount of a protein or polynucleotide disclosed herein that can be detected by standard analytical methods such as, but not limited to, polymerase chain reaction (PCR) and enzyme-linked immunosorbent assay (ELISA) techniques, and the like.

In one embodiment, the toxin proteins described herein are related by common function and exhibit insecticidal activity towards Lepidoptera insect species.

BCW 001 segments bestow black cutworm activity to Cry1 chimeras that contain such segments. Examples of BCW 001 segments that bestow black cutworm activity are set forth in SEQ ID NO:2 from about amino acid position 250 through about 606 and more particularly from about amino acid position 255 through about 606. Cry1 chimeras containing this segment of amino acids corresponding to Domains II and III of the BCW 001 toxin protein will often also confer upon the chimeric protein the toxic properties associated with controlling black cutworms, and this has been tested within Cry1A, Cry1B, Cry1C, Cry1D, Cry1E, and Cry1F scaffolds in which the applicable toxin construct has had its Domain II and III components substituted with this range of amino acids from BCW 001 and in many cases, the Black Cutworm activity is surprisingly maintained in the chimeric construct (data not shown).

In an aspect of the invention, the pest being controlled by the applicable BCW toxin protein is specifically an insect pest from the order Lepidoptera, including adults, pupae, larvae, and neonates.

The insects of the order Lepidoptera include, but are not limited to, armyworms, cutworms, loopers, and heliothines in the Family Noctuidae (e.g., fall armyworm (*Spodoptera frugiperda*), beet armyworm (*Spodoptera exigua*), bertha armyworm (*Mamestra* configurata), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (Hypena *scabra*), tobacco budworm (*Heliothis virescens*), granulate cutworm (*Agrotis subterranea*), western cutworm (*Agrotis orthogonia*), armyworm (Pseudaletia *unipuncta*), borers, casebearers, webworms, coneworms, cabbageworms and skeletonizers from the Family Pyralidae (e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*), leafrollers, budworms, seed worms, and fruit worms in the Family Tortricidae (e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera (e.g., diamondback moth (*Plutella xylostella*), pink bollworm (*Pectinophora gossypiella*), gypsy moth (*Lymantria dispar*). Other insect pests of order Lepidoptera include, e.g., Alabama argillacea (cotton leaf worm), Archips argyrospila (fruit tree leaf roller), *A. rosana* (European leaf roller) and other *Archips* species, *Chilo suppressalis* (Asiatic rice borer, or rice stem borer), Cnaphalocrocis medinalis (rice leaf roller), Crambus caliginosellus (corn root webworm), *C. teterrellus* (bluegrass webworm), Diatraea grandiosella (southwestern corn borer), *D. saccharalis* (surgarcane borer), Earias insulana (spiny bollworm), *E. vittella* (spotted bollworm), Helicoverpa armigera (American bollworm), *H. zea* (corn earworm or cotton bollworm), Heliothis virescens (tobacco budworm), Herpetogramma licarsisalis (sod webworm), Lobesia botrana (European grape vine moth), Pectinophora gossypiella (pink bollworm), Phyllocnistis citrella (citrus leafminer), Pieris brassicae (large white butterfly), *P. rapae* (imported cabbageworm, or small white butterfly), Plutella xylostella (diamondback moth), Spodoptera exigua (beet armyworm), *S. litura* (tobacco cutworm, cluster caterpillar), *S. frugiperda* (fall armyworm), and Tuta absoluta (tomato leafminer).

The proteins disclosed herein can also be used to produce antibodies that bind specifically to BCW specific toxin proteins and can be used to screen for and to find other members of the BCW toxin genus.

In one embodiment, exemplary polynucleotides that encode insect inhibitory BCW 001 related proteins are set forth in SEQ ID NO:1, 3, 5, 7, 9 and 11. Nucleotide sequences encoding these proteins can be used as probes and primers for screening to identify other members of the genus using thermal or isothermal amplification and/or hybridization methods and other identification methods known to those of ordinary skill in the art.

An aspect of the invention provides methods for discovering related proteins, and such methods include the sequencing of Bt genomes, assembly of sequence data, the identification and cloning of Bt genes encoding such pesticidal proteins, and the expression and testing of new Bt proteins to assay for pesticidal activity. Another aspect of the invention employs molecular methods to engineer and clone commercially useful proteins comprising chimeras of proteins from the genus of pesticidal proteins, e.g., the chimeras can be assembled from segments of the BCW toxic proteins to derive additional embodiments. The proteins disclosed can be subjected to alignment to each other and to other Bt pesticidal proteins, and segments of each such protein can be identified that are useful for substitution between the aligned proteins, resulting in the construction of chimeric proteins. Such chimeric proteins can be subjected to pest bioassay analysis and characterized for the presence of increased bioactivity and/or expanded target pest spectrum compared to the parent proteins from which each such segment in the chimera was derived. The pesticidal activity of the polypeptides can be further engineered for activity to a particular pest or to a broader spectrum of pests by swapping domains or segments with other proteins.

In one embodiment, the proteins disclosed herein include functionally equivalent fragments (N- or C-terminal deletions) of the proteins disclosed herein.

BCW toxic proteins are provided herein. In certain embodiments, the BCW 001 related toxin proteins can be isolated, can be provided in a composition, in a transgenic microorganism, or in a transgenic plant. In this embodiment, BCW 002 and particularly BCW 003 proteins confer Lepidoptera inhibitory activity, particularly inhibitory activity against black cutworm and/or sugarcane borer. Reference in this application to an "isolated protein", or an equivalent term or phrase, is intended to mean that the protein is one that is present alone or in combination with other compositions, but not within its natural environment. For example, toxin proteins of the present invention, and the like, that are naturally found within an organism are not considered to be "isolated" so long as these are within the organism in which these are naturally found. However, each of these would be "isolated" within the scope of this disclosure so long as the protein is not within the organism in which it is naturally found.

"Operably linked" as used herein refers to the joining of nucleic acid sequences or amino acid sequences such that one sequence can provide a required function or compatible or useful feature to a linked sequence.

Peptides, polypeptides, and proteins biologically functionally equivalent to BCW 001, BCW 002 and BCW 003 include, but are not limited to, amino acid sequences containing conservative amino acid substitutions in these BCW toxin protein sequences. In such amino acid sequences, one or more amino acids in the sequence is (are) substituted with another amino acid(s), resulting in a silent or conservative amino acid sequence change.

While the insect inhibitory polypeptides disclosed preferably comprises a BCW 001, BCW 002 or BCW 003 protein sequence, fragments and variants of this sequence possessing the same or similar insect inhibitory activity as that of this insect inhibitory protein are also disclosed herein. For example, contiguous sequences of at least 30, 35, 38, 40, 45, 50, 55, 60, 65, 70, 75, 100, 150, 200, 500, 550 or more amino acids in a BCW related toxin protein with insect inhibitory activity. In another embodiment, fragments of a BCW related toxin protein with insect inhibitory activity can comprise amino acid substitutions, deletions, insertions or additions in a BCW toxin protein sequence.

In one embodiment, the insect inhibitory polypeptide comprises an insect inhibitory segment from about residues 28 to about residue 618 of a BCW 001 protein sequence as set forth in SEQ ID NO:2. Non-limiting examples include any one of SEQ ID NOs:2, 4, or 6, or shorter fragments, or variants possessing the same or similar insect inhibitory activity as that of this particular BCW 001 protein on their own or in operable linkage in a chimeric protein. In another embodiment, segments having contiguous amino acid sequences of at least about 38 or more amino acids in any one of SEQ ID NOs:2, 4, or 6 with insect inhibitory activity also provide functional insecticidal protein. The insect inhibitory BCW 001 toxic fragments can also comprise segments with at least 30, 35, 38, 40, 45, 50, 100, 150, 200, 500, 550, 555, 560, 565, 570, 572, 574, 580 or 585 amino acid residues of the 591 amino acid region corresponding to about residues 28 to about 618 of the sequences of any one of SEQ ID NOs:2, 4, or 6.

In some embodiments, fragments of the mature BCW 001 protein (mature, meaning the protoxin form of the protein being 1180 amino acids, cleaved by proteolysis in the insect pest gut to release a core toxin just N terminal to residues 607 through about residue 618, releasing an active toxin segment comprising, more or less, residues 1 through residue 606 or any number of residues from about 5 through about 618, as set forth in SEQ ID NO:2, so long as the released segment exhibits toxic properties upon Black Cutworm larvae) can be truncated forms wherein one or more amino acids are deleted from the N-terminal end, C-terminal end, the middle of the protein, or combinations thereof with insect inhibitory activity. These fragments can be naturally occurring or synthetic variants of BCW 001, and retain the insect inhibitory activity of a BCW toxin protein. In certain embodiments, fragments of mature BCW 001, BCW 002, or BCW 003 proteins exhibit the pesticidal activity possessed by the starting protein molecules from which they are derived. A fragment or variant described herein may further comprise a domain identified herein which is responsible for the pesticidal activity of the protein. A truncated derivative having insect inhibitory activity is a BCW toxin protein corresponding to residues from about 28 to about 606 or through about 618 of a BCW 001 toxin protein sequence as set forth in SEQ ID NO:2 or to residues from about 29 to about 607 and through residue 619 of a BCW toxin protein as set forth in SEQ ID NO:4 or SEQ ID NO:6.

Yet in another embodiment, truncated N-terminal deletion mutations include, but are not limited to, BCW 001 toxic proteins that lack amino acid residues from either the N-terminus and/or the C-terminus of the toxin portion without protoxin, or the toxic core of BCW toxin proteins. For example, 1 to 6 N-terminal amino acid residues of the toxic core of a BCW 001 protein corresponding to residues 28 to 618 of SEQ ID NOs:2 or to residues 29 to 619 of SEQ ID NO:4 or 6 can be deleted. Truncated C-terminal deletion mutations of a BCW toxin protein corresponding to residues 28 to 618 of SEQ ID NO:2 or residues 29 to 619 of SEQ ID NO:4 or 6 include, but are not limited to, BCW toxin proteins that lack 1 to 6 C-terminal amino acid residues. In other embodiments, a BCW toxin protein with corresponding residues 28 to 618 of SEQ ID NO:2 or corresponding residues 29 to 619 of SEQ ID NO:4 or 6 can have both a N-terminal truncation of 1 to 6 amino terminal residues and a C-terminal truncation of 1 to 6 carboxy terminal residues.

In some embodiments, individual Segments 1 to 6 of a CPR24719 protein, or a combination of Segments 1 to 6, which bestow black cutworm activity to a protein different from CPR24719-1, can also exhibit the same or similar function.

The fragments and variants of a BCW toxin protein disclosed herein can possess about 62% or greater sequence identity, about 65%, 70%, 75%, 80%, 85%, 90%, 92%, 95%, 96%, 97%, 98%, or greater sequence identity, and about 99%, 99.5%, 100% amino acid sequence identity, to the corresponding segments of the mature BCW toxin protein having the corresponding amino acid sequences shown in residues 28 to 618 of SEQ ID NO:2 or to residues 29 to 619 of SEQ ID NO:4 or 6.

An embodiment of the invention includes recombinant polynucleotide compositions that encode BCW toxin proteins. For example, BCW toxin proteins can be expressed with recombinant DNA constructs in which an isolated polynucleotide molecule with the open reading frame encoding the protein is operably linked to elements such as a promoter and any other regulatory element functional for expression in the system for which the construct is intended. Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium. Non-limiting examples include plant-functional promoters operably linked to the BCW toxin protein encoding sequences for expression of the protein in plants or Bt-functional promoters operably linked to BCW toxin protein encoding sequences for expression of the protein in Bt. Other elements that can be operably linked to the BCW toxin protein encoding sequences include, but are not limited to, enhancers, introns, leaders, encoded protein immobilization tags (HIS-tag), encoded sub-cellular translocation peptides (e.g. plastid transit peptides, signal peptides), encoded polypeptide sites for post-translational modifying enzymes, ribosomal binding sites, and RNAi target sites.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, or a DNA molecule that has been incorporated into a host cell's DNA by genetic transformation or gene editing. Similarly, a "recombinant protein molecule" is a protein molecule comprising a combination of amino acids that would not naturally occur together without human intervention. For example, a recombinant protein molecule may be a protein molecule that is comprised of at least two amino acid molecules heterologous with respect to each other, a protein molecule that comprises an amino acid sequence that deviates from amino acid sequences that exist in nature, or a protein molecule that is expressed in a host cell as a result of genetic transformation of the host cell or by gene editing of the host cell genome.

Exemplary recombinant polynucleotide molecules provided herewith include, but are not limited to, SEQ ID NO:7, SEQ ID NO:9, and SEQ ID NO:11 as well as each of the nucleotide segments set forth in SEQ ID NO:3 and SEQ ID NO:5 and that encode the respective polypeptides or proteins having the amino acid sequence as set forth in SEQ ID NO:2 (BCW oo1), SEQ ID NO:4 (BCW 002), SEQ ID NO:6 (BCW 003) and SEQ ID NO:8, SEQ ID NO:10 and SEQ ID NO:12. The codons of a recombinant polynucleotide molecule encoding for proteins disclosed herein can be substituted by synonymous codons (also referred to as a silent substitution). Recombinant polynucleotides encoding any of the BCW toxin variant proteins disclosed herein are also provided.

A recombinant DNA construct comprising BCW toxin protein encoding sequences can also further comprise a region of DNA that encodes for one or more insect inhibitory agents which can be configured to concomitantly express or co-express with DNA sequence encoding a BCW toxin protein, a protein different from a BCW toxin protein, an insect inhibitory dsRNA molecule, or an insecticidal chemical compound. Non-limiting examples for insecticidal chemical compounds are organochlorides, organophosphates and carbamates, pyrethroids, neonicotinoids, and ryanoids.

A recombinant DNA construct can be assembled so that all proteins or dsRNA molecules are expressed from one promoter or each protein or dsRNA molecules is under separate promoter control or some combination thereof. The proteins disclosed herein can be expressed from a multi-gene expression system in which one or more proteins disclosed herein are expressed from a common nucleotide segment on which is also contained other open reading frames and/or promoters depending on the type of expression system selected. For example, a bacterial multi-gene expression system can utilize a single promoter to drive expression of multiply-linked/tandem open reading frames from within a single operon. In another example, a plant multi-gene expression system can utilize multiply-linked expression cassettes, each expressing a different protein or other agent such as one or more dsRNA molecules. In yet another example, a plant multi-gene expression system can utilize multiply-unlinked expression cassettes, each expressing a different protein or other agent such as one or more dsRNA molecules. A promoter for use in a recombinant nucleic acid described herein may comprise a complete promoter sequence or any variant or fragment thereof having promoter or gene-regulatory activity.

A recombinant polynucleotide or recombinant DNA construct comprising a BCW toxin protein encoding sequence can be delivered to host cells by vectors, e.g., a plasmid, baculovirus, artificial chromosome, virion, cosmid, phagemid, phage, or viral vector. Such vectors can be used to achieve stable or transient expression of a BCW toxin protein encoding sequence in a host cell, or subsequent expression to polypeptide. An exogenous recombinant polynucleotide or recombinant DNA construct that comprises a BCW toxin protein encoding sequence and that is introduced into a host cell is referred herein as a "transgene."

Also provided herein are transgenic bacteria, transgenic plant cells, transgenic plants, fungi and yeasts, and transgenic plant parts that contain any recombinant polynucleotide that expresses any one or more of the BCW toxin protein encoding sequences provided herein. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include, but is not limited to, an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by propagating, cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Also provided herein are methods of making transgenic plants that comprise insect or Lepidoptera inhibitory amounts of a BCW toxin protein. Such plants can be made by introducing a recombinant polynucleotide that encodes any of the BCW toxin proteins provided herein into a plant cell, and selecting a plant derived from said plant cell that expresses an insect or Lepidoptera inhibitory amount of the BCW toxin proteins. Plants can be derived from the plant cells by regeneration, seed, pollen, or meristem transformation techniques.

Methods for transforming plants are known in the art. For example, *Agrobacterium*-mediated transformation is described in US Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257 A1 (sugar beet), U.S. Pat. No. 5,750,871 (canola), U.S. Pat. No. 7,026,528 (wheat), and U.S. Pat. No. 6,365,807 (rice), and in Arencibia et al. (1998) Transgenic Res. 7:213-222 (sugarcane).

Also provided herein is the use of a transgenic plant that expresses an insect or Lepidoptera inhibitory amount of the BCW toxin protein to control an insect or Lepidoptera infestation. Any of the aforementioned transgenic plants can be used in methods for protecting a plant from insect or Lepidoptera infestation provided herein. Methods of obtaining transgenic plants that express Lepidopteran-active proteins such as Cry1A proteins (U.S. Pat. No. 5,880,275), Cry1B (U.S. patent application Ser. No. 10/525,318), Cry1C (U.S. Pat. No. 6,033,874), Cry1F, Cry1A/F chimeras (U.S. Pat. Nos. 7,070,982; 6,962,705, and 6,713,063), and a Cry2Ab protein (U.S. Pat. No. 7,064,249) are well characterized.

Also provided herein is the use of any of the aforementioned transgenic host cells to produce a BCW toxin protein.

Additional aspects of the invention include antibodies and methods for detecting polynucleotides that encode BCW toxin proteins or distinguishing fragments and segments thereof, methods for identifying additional insect inhibitory members of the protein genus, formulations and methods for controlling insect growth and/or infestation, and methods for providing such control to plants and other recipient hosts.

In certain embodiments, a plant product can comprise commodity or other products of commerce derived from a transgenic plant or transgenic plant part, where the commodity or other products can be tracked through commerce by detecting nucleotide segments, or expressed RNA or proteins that encode or comprise distinguishing portions of a BCW toxin protein. Such commodity or other products of commerce include, but are not limited to, plant parts, biomass, oil, meal, sugar, animal feed, flour, flakes, bran, lint, processed seed, and seed.

Also provided herewith are processed plant products wherein said processed product comprises a detectable amount of a recombinant polynucleotide encoding a BCW toxin protein, a segment thereof, an insect inhibitory fragment thereof, or any distinguishing portion thereof. In certain embodiments, the processed product is selected from the group consisting of: plant biomass, oil, meal, animal feed, flour, flakes, bran, lint, hulls, and processed seed. In certain embodiments, the processed product is non-regenerable.

Also provided herein are methods of controlling insects. In certain embodiments, Lepidoptera infestations of crop plants are controlled. Such methods can comprise growing a plant comprising an insect or Lepidoptera inhibitory amount of a BCW toxin protein. In certain embodiments, such methods can further comprise any one or more of: (i) applying any composition comprising or encoding a BCW toxin protein to the plant or a seed that gives rise to the plant; and/or (ii) transforming the plant or a plant cell that gives rise to the plant with a polynucleotide encoding a BCW toxin protein. In certain embodiments, the plant is a transiently or stably transformed transgenic plant comprising a transgene that expresses an insect or Lepidoptera inhibitory amount of a BCW toxin protein. In certain embodiments, the plant is a non-transgenic plant to which a composition comprising a BCW toxin protein has been applied. In certain embodiments of such methods, the plant is a corn or sugarcane plant. In certain embodiments, the Lepidoptera species is *Agrotis ipsilon*. In certain embodiments, the Lepidoptera species is *Diatraea saccharalis*. In certain embodiments, the Lepidoptera species is in a crop field.

Enrichment of the proteins disclosed herein either in plants or by a process can include culturing recombinant Bt cells under conditions to express/produce recombinant polypeptide/proteins. Such a process can include preparation by desiccation, lyophilization, homogenization, extraction, filtration, centrifugation, sedimentation, or concentration of a culture of recombinant Bt cells expressing/producing said recombinant polypeptide. Such a process can result in a Bt cell extract, cell suspension, cell homogenate, cell lysate, cell supernatant, cell filtrate, or cell pellet. By obtaining the recombinant polypeptides/proteins so produced, a composition that includes the recombinant polypeptides/proteins can include bacterial cells, bacterial spores, and parasporal inclusion bodies and can be formulated for various uses, including agricultural insect inhibitory spray products or as insect inhibitory formulations in diet bioassays.

In one embodiment, the insect inhibitory composition/formulation comprising the disclosed recombinant polypeptide/protein can further comprise at least one additional polypeptide that exhibits insect inhibitory activity against the same Lepidopteran insect species, but is different from the recombinant polypeptide to provide for a decreased incidence of Lepidopteran insect resistance to the BCW toxin protein or other Lepidopteran insect inhibitory composition. Such polypeptide is selected from the group consisting of: an insect inhibitory protein, an insect inhibitory dsRNA molecule, and a chemical compound. One example for the use of such ribonucleotide sequences to control insect pests is described in U.S. Patent Application Publication No. 2006/0021087. Examples of other such compositions include, but are not limited to, Cry1A (U.S. Pat. No. 5,880,275), Cry1Ab, Cry1Ac, Cry1Ae, Cry1B (U.S. patent application Ser. No. 10/525,318), Cry1C (U.S. Pat. No. 6,033, 874), Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry2A, Cry2Ab (U.S. Pat. No. 7,064,249), Cry2Ae, Cry4B, Cry6, Cry7, Cry8, Cry9, Cry15, Cry43A, Cry43B, ET35, ET66, TIC400, TIC800, TIC807, TIC834, TIC853 and TIC1415. Other non-limiting examples are Lepidoptera active proteins VIP, Axmi and DIG such as, but not limited to, Vip3A, VIP3Ab, AXMI-184, AXMI-196, DIG-3, DIG-4, DIG-5, and DIG-11, that can be combined with the proteins disclosed herein.

In other embodiments, such composition can further comprise at least one additional polypeptide that exhibits insect inhibitory activity to an insect that is not inhibited by an otherwise insect inhibitory BCW toxin protein to expand the spectrum of insect inhibition obtained. For example, for the control of Coleopteran pests, combinations of insect inhibitory BCW toxin proteins can be used with Coleopteran-active proteins such as, but not limited to, Cry1C variants, Cry3A variants, Cry3Bb (U.S. Pat. No. 6,501,009), Cry34/35, 5307, Axmi184, Axmi205, AxmiR1, TIC407, TIC417, TIC431, TIC901, TIC1201, TIC3131, DIG-10 and eHIPs (U.S. Patent Application Publication No. 2010/0017914).

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the Lepidopteran pest species to create a refuge. One particular example is described in U.S. Pat. No. 6,551,962.

Other embodiments disclosed herein comprise topically applied pesticidal chemical compounds that are designed for controlling pests that are also controlled by the proteins disclosed herein, to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in MOA with the proteins disclosed, so that the formulation pesticides act through a different MOA to control the same or similar pests that can be controlled by the proteins disclosed, or that such pesticides act to control pests within a broader host range, such as Lepidopteran or Hemipteran species or other plant pest species such as Coleopteran species that are not effectively controlled.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

The proteins disclosed herein can be combined in formulations for topical application to plant surfaces, to the soil, in formulations for seed treatments, and in formulations with other agents toxic to the target pests of Lepidopteran species. Such agents include but are not limited to: Cry1A proteins, Cry1B, Cry1C, Cry1F, Cry1A/F chimeras, and a Cry2Ab protein.

EXAMPLES

The following disclosed embodiments are merely representative of the invention, which may be embodied in various forms. Thus, specific structural and functional details disclosed herein are not to be interpreted as limiting. It should be understood that the entire disclosure of each reference cited herein is incorporated herein by reference.

Example 1

This example teaches the discovery and analysis of the toxin protein BCW 001 and construction of chimeric toxins BCW 002 and BCW 003.

Bt strain EG4384 was identified to confer Lepidopteran activity in diet bioassays using spore crystal preparations. The sequence of the genome of this strain was generated, raw sequence reads processed, contigs assembled from processed reads, open reading frames identified that showed homology to Cry1 proteins, and deduced amino acid sequences analyzed. A particular open reading frame as set forth in SEQ ID NO:1 was identified that encoded a deduced amino acid sequence of a protein (BCW 001, SEQ ID NO:2) that exhibits a novel amino acid sequence compared to most Cry1 proteins known in the art. The deduced protein from the open reading frame has all of the characteristics of a novel Cry1 type protein, as it is 1180 amino acids in length, and alignment to known Cry1 proteins indicates that this protein has a characteristic three domain structure within the approximately 600-630 amino terminal amino acids, and a Cry1A type characteristic protoxin amino acid sequence structure. The polynucleotide sequence encoding this predicted amino acid sequence contains an open reading frame that is also Cry1 characteristic, i.e., a NheI restriction site within the DNA segment encoding the C terminal region of the predicted Domain I of the toxin, and a KpnI restriction site within the DNA segment encoding the N terminal portion of the predicted protoxin domain.

A comparison of the amino acid sequence of the BCW 001 toxin to Cry1Ac reveals that the amino acid segment corresponding to Domain I (amino acids from about position 1 through about position 258) exhibits only about 67% identity to that same segment within Cry1Ac, the amino acid segment corresponding to Domain II (amino acids from about position 58 through about position 460) exhibits very low percent identity to that same segment within Cry1Ac, and the amino acid segment corresponding to Domain III (amino acids from about position 460 through about position 607) exhibits about 63% identity to a Domain III segment from Cry1Ah2.

The DNA segment encoding substantially the predicted Domains II and III, from the NheI through the KpnI restriction sites, was excised and substituted for the corresponding segment of a Cry1Ac coding sequence in an expression vector containing a DNA segment encoding Cry1Ac, resulting in an open reading frame consisting of, and linking in frame in consecutive order from five prime to three prime, a first segment encoding Domain I of a Cry1Ac, a second segment encoding Domain II and III of BCW 001, and a third segment encoding the protoxin domain of the Cry1Ac toxin protein. This chimeric construct (SEQ ID NO:3) encodes a chimeric toxin protein referred to herein as BCW 002 (SEQ ID NO:4). Shifting the breakpoint between Domain I and Domain II slightly results in an open reading frame (SEQ ID NO:5) encoding a chimeric toxin protein referred to herein as BCW 003 (SEQ ID NO:6), having an amino acid sequence differing from BCW 002 only at acid position 259. BCW 003, like BCW 001, contains a threonine (T) at position 259 while BCW 002 contains an isoleucine (I) at that position. BCW 001 differs from BCW 002 and BCW 003 principally within Domain I of the toxin, i.e. amino acids 1-202, and BCW 002 and BCW 002 are, as stated above, virtually identical except for the I/T difference at position 259.

Example 2

This example teaches the effective Lepidopteran pest control biological activity of the BCW 001, 002 and 003 proteins.

Transforming constructs expressing the BCW 001, 002 and 003 toxin proteins into E. coli or into applicable Bacillus thuringiensis or other Bacilli allowed for the testing of the expressed proteins in bioassay and comparison to proteins known in the art to be toxic to Black Cutworm, such as Cry1Fa and Cry1Ac. The resulting recombinant strains were observed to express a recombinant protein with activity against Lepidopteran pests. Bioassay activity was particularly strong when tested against Black Cutworm and Corn Earworm larvae. As specified above in the detailed description, the background and the summary of the invention, there are very few toxin proteins that have been discovered that exhibit any appreciable level of bioactivity against Black Cutworm, and so there is a need in the art for identification of such proteins for use in plants to protect such plants from Black Cutworm infestation, and to ensure that there is a sufficient supply of supplemental Black Cutworm active proteins available to overcome any development of resistance to any such Black Cutworm active proteins currently in use, such as Cry1Fa toxin proteins.

Example 3

This example teaches that Domains II and III of BCW 001 are sufficient for conveying Black Cutworm bioactivity to other Cry1 toxin proteins when such domains are substituted for the corresponding domains in such other Cry1 toxins.

Many BCW toxin chimeras with activity against Lepidoptera were identified, two chimeras in particular exhibited strong activity against BCW, WBC, and SCB.

Constructs having nucleotide sequences encoding Cry1Ab, Cry1Ac, and Cry1Ca were used to construct chimeras containing the Domain II and Domain III BCW 001 segments substituted for the applicable domains of Cry1Ab, Cry1Ac, and Cry1Ca, and the resulting native and chimeric proteins were tested in spore crystal bioassays. The activity activities against BCW, FAW and CEW in such diet bioassays were tabulated. Under the experimental conditions tested, Cry1Ac exhibited activity against FAW, BCW and CEW, Cry1Ab exhibited activity against FAW and CEW, but not against BCW, and Cry1Ca did not exhibit activity against FAW, BCW, as well as CEW. BCW 001 exhibited activity against BCW and CEW, but not FAW. Compared to BCW 003, the activity against BCW for Cry1Ac was about tenfold less for Cry1Ac. Cry1Ab, and Cry1Ac, chimeras containing Domains II and III of BCW 001 exhibited toxic properties when tested in bioassays against FAW, BCW and CEW. Cry1Ac was not toxic against CEW and Cry1Ab was not toxic against BCW. Cry1Ca/BCW 001 chimeras were constructed in which Cry Ca Domain III was substituted for the corresponding domain of BCW 001, and the resulting chimeric toxin exhibited toxic properties to FAW, BCW and CEW, whereas the Cry1Ca toxin was ineffective when tested against any of these pests.

Example 4

This example illustrates the toxic properties of BCW 001, 002 and 003 when tested in bioassay against a variety of Lepidopteran pests.

Protocols for bioassays and scoring insects for mortality and stunting are known in the art, examples of which are described in PCT Patent Application Publication No. WO 2012/139004 and in U.S. Pat. No. 7,927,598.

FIG. 1 correlates the various BCW 001, 002 and 003 toxin proteins to pesticidal activity by insect species in diet bioassays. Each of these toxin proteins demonstrated activity against Lepidopteran insects.

Example 5

This example teaches the construction of artificial sequences encoding the proteins of the present invention for use in plants, the preparation of plant vectors and constructs for use in plants, and the production of plants expressing the proteins of the present invention.

Nucleotide sequences encoding BCW 001 protein (SEQ ID NO:1), BCW 002 protein (SEQ ID NO:3), and BCW 003 protein (SEQ ID NO:5) were designed and synthesized according to methods described in U.S. Pat. No. 5,500,365. These engineered coding regions designed for plant expression are provided herein as SEQ ID NO:7 encoding BCW 001, SEQ ID NO:9 encoding BCW 002, and SEQ ID NO:11 encoding BCW 003.

A variety of plant expression cassettes were constructed with the sequences as set forth in SEQ ID NOs:7, 9, and 11. Such expression cassettes are useful for transient expression in plant protoplasts or transformation of plant cells. Typical expression cassettes were designed with respect to the eventual placement of the protein within the cell. One set of expression cassettes was designed in a manner to allow the protein to be translated and remain in the cytosol. Another set of expression cassettes was designed to have a transit peptide contiguous with the toxin protein to allow targeting to an organelle of the cell such as the chloroplast or plastid. All expression cassettes were designed to begin at the 5' end with a promoter, which can be comprised of multiple promoter elements and enhancer elements contiguously linked to boost the expression of the transgene. The promoter sequence was usually followed contiguously with one or more leader sequences 3' to the promoter. An intron sequence was provided 3' to the leader sequence to improve expression of the transgene. A coding sequence for the toxin or transit peptide and coding sequence for the toxin was located 3' of the promoter, leader and intron configuration. A sequence was provided 3' of the coding sequence to facilitate termination of transcription and provides sequences important for the polyadenylation of the resulting transcript. All of the elements described above were arranged contiguously, often with an additional sequence provided for the construction of the expression cassette such as restriction endonuclease sites or ligation independent cloning sites.

For corn plants, a set of expression cassettes was designed for cytosolic expression of BCW 001 comprising a *Mexicana* ubiquitin 1 promoter, BCW 002 comprising an *Orysza sativa* actin 15 promoter or a 35S promoter, and BCW 003 comprising a 35S promoter.

Another set of expression cassettes was designed for targeted expression in corn plants of the BCW 002 and BCW 003 insect toxin proteins in which a chloroplast peptide encoding sequence (e.g., CTP2) was fused in frame at the 5' end of the segment of DNA encoding the BCW toxin proteins, comprising a *Orysza sativa* actin 15 promoter or a 35S promoter, and a sequence comprising a 35S promoter.

Sugarcane plant expression cassettes comprising a CaMV 35S promoter or a PClSV.FLt promoter operably linked to a 35S promoter were constructed in plant transformation vectors. In some cases a cassette expressing a chloroplast targeted Cry2Ab was included.

Plants expressing the proteins of the present invention were tested against third instar BCW, WBC, CEW, SWC and SCB larvae. The cytosolic expression cassette for BCW 001 and the cytosolic and plastid targeted expression cassettes for BCW 002 and BCW 003 were cloned and were used to produce transgenic corn events expressing these proteins. The transformed cells were induced to form plants by methods known in the art. Bioassays using plant leaf disks were performed similarly as described in U.S. Pat. No. 8,344,207. The leaf damage rating (LDR) was assigned a rating score based upon the percent of the leaf disc devoured by the insect on a scale from 0 (0% eaten) to 11 (greater than 50%) eaten. Rating score steps increase incrementally by 5%. An isogenic corn line was used to derive tissue as a negative control and the results were evaluated. Both, the plastid targeted expression and cytosolic expression of the BCW 002 and BCW 003 insect toxin proteins reduced feeding damage relative to the untransformed control. The results of the leaf disc assays against these insects were consistent with the bioassay data from the examples presented above. One construct comprising a BCW 003 cassette for cytosolic expression resulted in 34 transformation events, 25 of these exhibited complete control of BCW neonates. Corn plants expressing BCW 001 and BCW 003 into the cytosol were also tested against CEW, SWC and FAW. Plants expressing BCW 003 exhibited 100% control of CEW and SWC and LDR values ranging between 1 and 2. Three transformation events expressing BCW 001 resulted in plants exhibiting efficacy against CEW and SWC and LDR values ranging between 1 and 3. This is consistent with the diet bioassay data presented in the previous examples.

Transgenic sugarcane plants expressing BCW 003 were generated and tested against SCB in bioassays. Each bioassay included leaf discs from wild type sugarcane as negative control and a positive control expressing high levels of Cry2Ab. Insect mortality and leaf damage were measured four (4) days after infestation. Leaf discs from several transgenic sugarcane events expressing BCW 003 were found to control sugarcane borer in planta and exhibited a damage rating of below 2, similar to the positive control and an average insect mortality rate of 90-100%.

Transgenic events expressing BCW 003 and Cry2Ab exhibited better SCB control compared to events that only expressed BCW 003.

What is claimed is:

1. A polynucleotide construct comprising a nucleotide sequence encoding:
   (a) an insecticidal protein having the amino acid sequence comprising SEQ ID:NO 6 or SEQ ID NO:12; or
   (b) an insecticidal polypeptide exhibiting at least 98% identity to the amino acid sequence of (a) wherein said nucleotide sequence is operably linked to a heterologous promoter sequence.

2. A protein toxic to black cutworm Lepidopteran species comprising the amino acid sequence as set forth in SEQ ID NO:6.

3. The polynucleotide construct according to claim 1, wherein said insecticidal protein exhibits activity against Lepidopteran species selected from the group consisting of *Spodoptera frugiperda, Spodoptera exigua, Spodoptera litura, Mamestra configurata, Striacosta albicosta, Trichoplusia ni, Pseudoplusia includens, Anticarsia gemmatalis, Hypena scabra, Heliothis virescens, Agrotis subterranea, Pseudaletia unipuncta, Agrotis ipsilon, Agrotis orthogonia, Ostrinia nubilalis, Amyelois transitella, Crambus caliginosellus, Herpetogramma licarsisalis, Homoeosoma electellum, Elasmopalpus lignosellus, Cydia pomonella, Endopiza viteana, Grapholita molesta, Suleima helianthana, Plutella xylostella, Pectinophora gossypiella, Lymantria dispar, Alabama argillacea, Archips argyrospila, Archips rosana, Chilo suppressalis, Cnaphalocrocis medinalis, Crambus teterrellus, Diatraea grandiosella, Diatraea saccharalis, Earias insulana, Egrias vittella, Helicoverpa armigera, Helicoverpa zea, Lobesia botrana, Pectinophora gossypiella, Phyllocnistis citrella, Pieris brassicae, Pieris rapae, Plutella xylostella*, and *Tuta absoluta*.

4. The protein according to claim 2 further comprising bioactivity against Lepidopteran species selected from the group consisting of *Spodoptera frugiperda, Spodoptera exigua, Spodoptera litura, Mamestra configurata, Striacosta albicosta, Trichoplusia ni, Pseudoplusia includens, Anticarsia gemmatalis, Hypena scabra, Heliothis virescens, Agrotis subterranea, Pseudaletia unipuncta, Agrotis ipsilon, Agrotis orthogonia, Ostrinia nubilalis, Amyelois transitella, Crambus caliginosellus, Herpetogramma licarsisalis, Homoeosoma electellum, Elasmopalpus lignosellus, Cydia pomonella, Endopiza viteana, Grapholita molesta, Suleima helianthana, Plutella xylostella, Pectinophora gossypiella, Lymantria dispar, Alabama argillacea, Archips argyrospila, Archips rosana, Chilo suppressalis, Cnaphalocrocis medinalis, Crambus teterrellus, Diatraea grandiosella, Diatraea saccharalis, Earias insulana, Egrias vittella, Helicoverpa armigera, Helicoverpa zea, Lobesia botrana, Pectinophora gossypiella, Phyllocnistis citrella, Pieris brassicae, Pieris rapae, Plutella xylostella*, and *Tuta absoluta*.

5. A vector comprising the polynucleotide construct of claim 1.

6. A host cell comprising the polynucleotide construct of claim 1, wherein the host cell is selected from the group consisting of a bacterial cell, a yeast cell, and a plant cell.

7. The host cell of claim 6, wherein said plant cell is selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

8. A plant comprising the polynucleotide construct of claim 1.

9. A seed produced from the plant of claim 8, wherein said seed comprises a detectable amount of said polynucleotide construct.

10. The plant of claim 8, wherein seed, pollen, progeny, plant cells, plant tissue and commodity products produced from said plant comprise a detectable amount of said polynucleotide construct.

11. A biological sample comprising a detectable amount of the polynucleotide construct of claim 1.

12. A composition providing an insecticidally effective amount of the protein of claim 2 for controlling a Lepidopteran pest species, and an agent different from said protein and also toxic to the same Lepidopteran species, wherein said agent is selected from the group consisting of: a polypeptide having an amino acid sequence different from said protein, an RNA molecule, and a chemical compound.

13. A method of producing seed comprising the nucleotide sequence of claim 1, said method comprising:
   a. planting one or more seed comprising said nucleotide sequence;
   b. growing plants from said seed; and
   c. harvesting a crop of seed from said plants, wherein said crop of seed comprises said nucleotide sequence.

14. A Lepidopteran toxic protein comprising in operable linkage:
   a. a first peptide segment comprising a Cry1A Domain I amino acid sequence;
   b. a second peptide segment comprising residues 258-606 of SEQ ID NO:6;
wherein said Lepidopteran toxic protein exhibits toxic bioactivity when tested against a Lepidopteran pest selected from the group consisting of a Black Cutworm (*A. ipsilon*), a Corn Earworm (*H. zea*), a Western Bean Cutworm (*S. albicosta*), a European Corn Borer (*O. nubilalis*), a Southwestern Corn Borer (*D. grandiosella*), a Cabbage Looper (*T. ni*), a Soybean Looper (*P. includens*), a Fall Armyworm (*S. frugiperda*), and a Sugarcane Borer (*D. saccharalis*).

\* \* \* \* \*

SEQUENCE LISTING

```
<160> NUMBER OF SEQ ID NOS: 12

<210> SEQ ID NO 1
<211> LENGTH: 3543
<212> TYPE: DNA
<213> ORGANISM: Bacillus thuringiensis
<220> FEATURE:
<221> NAME/KEY: CDS
<222> LOCATION: (1)..(3540)

<400> SEQUENCE: 1 atg gag gaa aat aat cag aat caa tgc gtc cct tat aat tgt ttg aat        48
Met Glu Glu Asn Asn Gln Asn Gln Cys Val Pro Tyr Asn Cys Leu Asn
1               5                   10                  15 aat cct gca atc gaa ata tta gaa gga gac aga ata tca gtt ggt aac        96
Asn Pro Ala Ile Glu Ile Leu Glu Gly Asp Arg Ile Ser Val Gly Asn
                20                  25                  30 act cca atc gat att tct cta tca ctt gtg gaa ctt ctt att agt gaa       144
Thr Pro Ile Asp Ile Ser Leu Ser Leu Val Glu Leu Leu Ile Ser Glu
            35                  40                  45 ttt gtc cca ggc ggt gga ata ata aca gga ttg ttg aac ata gta tgg       192
Phe Val Pro Gly Gly Gly Ile Ile Thr Gly Leu Leu Asn Ile Val Trp
        50                  55                  60 gga ttt gta ggg cct tcc caa tgg gac gca ttt ctt gct caa gtg gaa       240
Gly Phe Val Gly Pro Ser Gln Trp Asp Ala Phe Leu Ala Gln Val Glu
65                  70                  75                  80 cag tta att aac caa agg ata tca gaa gct gta aga aat aca gca att       288
Gln Leu Ile Asn Gln Arg Ile Ser Glu Ala Val Arg Asn Thr Ala Ile
                85                  90                  95 cag gaa tta gag gga atg gcg cgg gtt tat aga acc tat gct act gct       336
Gln Glu Leu Glu Gly Met Ala Arg Val Tyr Arg Thr Tyr Ala Thr Ala
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 100 |     |     |     |     | 105 |     |     |     |     | 110 |     |     |      |
| ttt | gct | gag | tgg | gaa | aga | gat | cct | aat | aac | aca | gat | cta | aga | gaa | gca | 384  |
| Phe | Ala | Glu | Trp | Glu | Arg | Asp | Pro | Asn | Asn | Thr | Asp | Leu | Arg | Glu | Ala |      |
|     |     | 115 |     |     |     |     | 120 |     |     |     |     | 125 |     |     |     |      |
| gta | cgg | aca | cag | ttt | aca | gca | act | gag | act | tat | atc | agt | gga | aga | ata | 432  |
| Val | Arg | Thr | Gln | Phe | Thr | Ala | Thr | Glu | Thr | Tyr | Ile | Ser | Gly | Arg | Ile |      |
|     | 130 |     |     |     |     | 135 |     |     |     |     | 140 |     |     |     |     |      |
| tct | gtt | tta | aaa | att | caa | aat | ttt | gaa | gtg | cag | ctg | tta | tcg | gtg | ttt | 480  |
| Ser | Val | Leu | Lys | Ile | Gln | Asn | Phe | Glu | Val | Gln | Leu | Leu | Ser | Val | Phe |      |
| 145 |     |     |     |     | 150 |     |     |     |     | 155 |     |     |     |     | 160 |      |
| gcc | caa | gct | gcc | aat | tta | cat | tta | tct | tta | tta | aga | gac | gtt | gtg | ttt | 528  |
| Ala | Gln | Ala | Ala | Asn | Leu | His | Leu | Ser | Leu | Leu | Arg | Asp | Val | Val | Phe |      |
|     |     |     |     | 165 |     |     |     |     | 170 |     |     |     |     | 175 |     |      |
| ttt | ggg | caa | aga | tgg | ggg | ttt | tca | acg | aca | acc | gta | aat | aat | tac | tac | 576  |
| Phe | Gly | Gln | Arg | Trp | Gly | Phe | Ser | Thr | Thr | Thr | Val | Asn | Asn | Tyr | Tyr |      |
|     |     |     | 180 |     |     |     |     | 185 |     |     |     |     | 190 |     |     |      |
| aat | gat | tta | aca | gaa | gag | att | agt | acc | tat | aca | gat | tat | gca | gta | cgc | 624  |
| Asn | Asp | Leu | Thr | Glu | Glu | Ile | Ser | Thr | Tyr | Thr | Asp | Tyr | Ala | Val | Arg |      |
|     |     | 195 |     |     |     |     | 200 |     |     |     |     | 205 |     |     |     |      |
| tgg | tac | aat | acg | gga | tta | gag | cgt | gta | tgg | gga | ccg | gat | tct | aga | gat | 672  |
| Trp | Tyr | Asn | Thr | Gly | Leu | Glu | Arg | Val | Trp | Gly | Pro | Asp | Ser | Arg | Asp |      |
|     | 210 |     |     |     |     | 215 |     |     |     |     | 220 |     |     |     |     |      |
| tgg | gta | agg | tat | aat | caa | ttt | aga | aga | gag | cta | aca | ctt | act | gta | tta | 720  |
| Trp | Val | Arg | Tyr | Asn | Gln | Phe | Arg | Arg | Glu | Leu | Thr | Leu | Thr | Val | Leu |      |
| 225 |     |     |     |     | 230 |     |     |     |     | 235 |     |     |     |     | 240 |      |
| gat | atc | gtt | gct | cta | ttc | cca | aat | tat | gat | agt | cga | agg | tat | cca | att | 768  |
| Asp | Ile | Val | Ala | Leu | Phe | Pro | Asn | Tyr | Asp | Ser | Arg | Arg | Tyr | Pro | Ile |      |
|     |     |     |     | 245 |     |     |     |     | 250 |     |     |     |     | 255 |     |      |
| cga | aca | gtt | tcc | caa | tta | aca | aga | gaa | att | tat | acg | aac | cca | gta | tta | 816  |
| Arg | Thr | Val | Ser | Gln | Leu | Thr | Arg | Glu | Ile | Tyr | Thr | Asn | Pro | Val | Leu |      |
|     |     |     | 260 |     |     |     |     | 265 |     |     |     |     | 270 |     |     |      |
| gaa | aat | ttt | gat | ggt | agt | ttt | cgt | gga | atg | gct | cag | aga | ata | gaa | cag | 864  |
| Glu | Asn | Phe | Asp | Gly | Ser | Phe | Arg | Gly | Met | Ala | Gln | Arg | Ile | Glu | Gln |      |
|     |     | 275 |     |     |     |     | 280 |     |     |     |     | 285 |     |     |     |      |
| aat | att | agg | caa | cca | cat | ctt | atg | gat | atc | ctt | aat | agt | ata | acc | att | 912  |
| Asn | Ile | Arg | Gln | Pro | His | Leu | Met | Asp | Ile | Leu | Asn | Ser | Ile | Thr | Ile |      |
|     | 290 |     |     |     |     | 295 |     |     |     |     | 300 |     |     |     |     |      |
| tat | act | gat | gtg | cat | aga | ggc | ttt | aat | tat | tgg | tca | ggg | cat | caa | ata | 960  |
| Tyr | Thr | Asp | Val | His | Arg | Gly | Phe | Asn | Tyr | Trp | Ser | Gly | His | Gln | Ile |      |
| 305 |     |     |     |     | 310 |     |     |     |     | 315 |     |     |     |     | 320 |      |
| aca | gct | tct | cct | gta | ggg | ttt | tca | gga | cca | gaa | ttc | gca | ttc | cct | tta | 1008 |
| Thr | Ala | Ser | Pro | Val | Gly | Phe | Ser | Gly | Pro | Glu | Phe | Ala | Phe | Pro | Leu |      |
|     |     |     |     | 325 |     |     |     |     | 330 |     |     |     |     | 335 |     |      |
| ttt | ggg | aat | gcg | gga | aat | gca | gct | cca | ccc | gta | ctt | gtc | tca | tta | act | 1056 |
| Phe | Gly | Asn | Ala | Gly | Asn | Ala | Ala | Pro | Pro | Val | Leu | Val | Ser | Leu | Thr |      |
|     |     |     | 340 |     |     |     |     | 345 |     |     |     |     | 350 |     |     |      |
| ggt | ttg | ggg | att | ttt | aga | aca | tta | tct | tca | cct | tta | tat | aga | aga | att | 1104 |
| Gly | Leu | Gly | Ile | Phe | Arg | Thr | Leu | Ser | Ser | Pro | Leu | Tyr | Arg | Arg | Ile |      |
|     |     | 355 |     |     |     |     | 360 |     |     |     |     | 365 |     |     |     |      |
| ata | ctt | ggt | tca | ggc | cca | aat | aat | cag | gaa | ctg | ttt | gtc | ctt | gat | gga | 1152 |
| Ile | Leu | Gly | Ser | Gly | Pro | Asn | Asn | Gln | Glu | Leu | Phe | Val | Leu | Asp | Gly |      |
|     | 370 |     |     |     |     | 375 |     |     |     |     | 380 |     |     |     |     |      |
| acg | gag | ttt | tct | ttt | gcc | tcc | cta | acg | acc | aac | ttg | cct | tcc | act | ata | 1200 |
| Thr | Glu | Phe | Ser | Phe | Ala | Ser | Leu | Thr | Thr | Asn | Leu | Pro | Ser | Thr | Ile |      |
| 385 |     |     |     |     | 390 |     |     |     |     | 395 |     |     |     |     | 400 |      |
| tat | aga | caa | agg | ggt | aca | gtc | gat | tca | cta | gat | gta | ata | ccg | cca | cag | 1248 |
| Tyr | Arg | Gln | Arg | Gly | Thr | Val | Asp | Ser | Leu | Asp | Val | Ile | Pro | Pro | Gln |      |
|     |     |     |     | 405 |     |     |     |     | 410 |     |     |     |     | 415 |     |      |
| gat | aat | agt | gta | cca | cct | cgt | gcg | gga | ttt | agc | cat | cga | ttg | agt | cat | 1296 |

```
                                                                                   -continued Asp Asn Ser Val Pro Pro Arg Ala Gly Phe Ser His Arg Leu Ser His
            420             425                 430 gtt aca atg ctg agc caa gca gct gga gca gtt tac acc ttg aga gct        1344
Val Thr Met Leu Ser Gln Ala Ala Gly Ala Val Tyr Thr Leu Arg Ala
        435                 440                 445 cca acg ttt tct tgg cag cat cgc agt gct acg aca act aat ata att        1392
Pro Thr Phe Ser Trp Gln His Arg Ser Ala Thr Thr Asn Ile Ile
    450                 455                 460 gca gcg gat agt att act caa att cct gct gtt aaa gga cgt tct att        1440
Ala Ala Asp Ser Ile Thr Gln Ile Pro Ala Val Lys Gly Arg Ser Ile
465                 470                 475                 480 att aat aat ggc acg gta att tca gga cca ggg ttt acc gga ggc gat        1488
Ile Asn Asn Gly Thr Val Ile Ser Gly Pro Gly Phe Thr Gly Gly Asp
                485                 490                 495 ttg gtt aga tta tac aat gct gat ttt aat att aat aat aga gca tac        1536
Leu Val Arg Leu Tyr Asn Ala Asp Phe Asn Ile Asn Asn Arg Ala Tyr
            500                 505                 510 ctt gaa gtt ccg ata ttc ttc caa tca ccc tct aca aat tat cgt gtt        1584
Leu Glu Val Pro Ile Phe Phe Gln Ser Pro Ser Thr Asn Tyr Arg Val
        515                 520                 525 cgt gtt cgt tat gct tct aca tct tca ctc cct gta gat gta gtt ttc        1632
Arg Val Arg Tyr Ala Ser Thr Ser Ser Leu Pro Val Asp Val Val Phe
    530                 535                 540 gga aat att agt cat cct act aca ttc cca gcc act gcc aga tca tta        1680
Gly Asn Ile Ser His Pro Thr Thr Phe Pro Ala Thr Ala Arg Ser Leu
545                 550                 555                 560 gat aat cta caa tcc aat gat ttt gga tat att gat att gct gga act        1728
Asp Asn Leu Gln Ser Asn Asp Phe Gly Tyr Ile Asp Ile Ala Gly Thr
                565                 570                 575 ttc tta cct tca cta ggg cct agt ata ggt atc aga cct atg tta tct        1776
Phe Leu Pro Ser Leu Gly Pro Ser Ile Gly Ile Arg Pro Met Leu Ser
            580                 585                 590 act att aat ttg ata gta gat aga ttt gaa ttt att cca gta act gca        1824
Thr Ile Asn Leu Ile Val Asp Arg Phe Glu Phe Ile Pro Val Thr Ala
        595                 600                 605 acc ttt gaa gca gaa tcg gat tta gaa aga gca caa aag gcg gtg aat        1872
Thr Phe Glu Ala Glu Ser Asp Leu Glu Arg Ala Gln Lys Ala Val Asn
    610                 615                 620 gcg ctg ttt act tct aca aac caa cta ggg ata aaa aca gat gtg acg        1920
Ala Leu Phe Thr Ser Thr Asn Gln Leu Gly Ile Lys Thr Asp Val Thr
625                 630                 635                 640 gat tat cat att gat caa gtg tcc aat tta gtg gag tgt tta tcg gat        1968
Asp Tyr His Ile Asp Gln Val Ser Asn Leu Val Glu Cys Leu Ser Asp
                645                 650                 655 gaa ttt tat ctg gat gaa aag cga gaa ttg tcc gag aaa gtc aaa cat        2016
Glu Phe Tyr Leu Asp Glu Lys Arg Glu Leu Ser Glu Lys Val Lys His
            660                 665                 670 gcg aag cga ctc agt gat gag cga aat tta ctt caa gat cca aac ttc        2064
Ala Lys Arg Leu Ser Asp Glu Arg Asn Leu Leu Gln Asp Pro Asn Phe
        675                 680                 685 agg ggc atc aat aga caa cca gat cgt ggc tgg aga gga agt acg gat        2112
Arg Gly Ile Asn Arg Gln Pro Asp Arg Gly Trp Arg Gly Ser Thr Asp
    690                 695                 700 att acc atc caa gga gga gat gac gta ttc aaa gag aat tac gtc aca        2160
Ile Thr Ile Gln Gly Gly Asp Asp Val Phe Lys Glu Asn Tyr Val Thr
705                 710                 715                 720 cta cca ggt acc ttt gat gag tgc tat cca acg tat tta tat caa aaa        2208
Leu Pro Gly Thr Phe Asp Glu Cys Tyr Pro Thr Tyr Leu Tyr Gln Lys
                725                 730                 735
```

-continued

| | |
|---|---|
| ata gat gag tcg aaa tta aaa gcc tat acc cgt tat caa tta aga ggg<br>Ile Asp Glu Ser Lys Leu Lys Ala Tyr Thr Arg Tyr Gln Leu Arg Gly<br>        740                        745                        750 | 2256 |
| tat atc gag gat agt caa gac tta gaa atc tat tta att cgc tac aat<br>Tyr Ile Glu Asp Ser Gln Asp Leu Glu Ile Tyr Leu Ile Arg Tyr Asn<br>        755                        760                        765 | 2304 |
| gca aaa cat gaa aca gta aat gtg cca ggt acg ggt tcc tta tgg ccg<br>Ala Lys His Glu Thr Val Asn Val Pro Gly Thr Gly Ser Leu Trp Pro<br>        770                        775                        780 | 2352 |
| ctt tca gcc caa agt cca atc gga aag tgt gga gag ccg aat cga tgc<br>Leu Ser Ala Gln Ser Pro Ile Gly Lys Cys Gly Glu Pro Asn Arg Cys<br>785                        790                        795                        800 | 2400 |
| gcg cca cac ctt gaa tgg aat cct gat tta cac tgt tcc tgc aga gac<br>Ala Pro His Leu Glu Trp Asn Pro Asp Leu His Cys Ser Cys Arg Asp<br>                        805                        810                        815 | 2448 |
| ggg gaa aaa tgt gct cat cat tct cat cat ttc tcc ttg gac att gat<br>Gly Glu Lys Cys Ala His His Ser His His Phe Ser Leu Asp Ile Asp<br>        820                        825                        830 | 2496 |
| gtt gga tgt aca gac tta aat gag gat tta ggt gta tgg gta ata ttc<br>Val Gly Cys Thr Asp Leu Asn Glu Asp Leu Gly Val Trp Val Ile Phe<br>                        835                        840                        845 | 2544 |
| aag att aag acg caa gat ggc cat gca aga cta gga aat cta gag ttt<br>Lys Ile Lys Thr Gln Asp Gly His Ala Arg Leu Gly Asn Leu Glu Phe<br>850                        855                        860 | 2592 |
| ctc gaa gag aaa cca tta gta ggg gaa gca cta gct cgt gtg aaa aga<br>Leu Glu Glu Lys Pro Leu Val Gly Glu Ala Leu Ala Arg Val Lys Arg<br>865                        870                        875                        880 | 2640 |
| gcg gag aaa aaa tgg aga gac aaa cgc gaa aaa tta caa ttg gaa aca<br>Ala Glu Lys Lys Trp Arg Asp Lys Arg Glu Lys Leu Gln Leu Glu Thr<br>                        885                        890                        895 | 2688 |
| aat atc gtt tat aaa gag gca aaa gaa tct gta gat gct tta ttt gta<br>Asn Ile Val Tyr Lys Glu Ala Lys Glu Ser Val Asp Ala Leu Phe Val<br>        900                        905                        910 | 2736 |
| aac tct caa tat gat caa tta caa gcg gat acg aac atc gcg atg att<br>Asn Ser Gln Tyr Asp Gln Leu Gln Ala Asp Thr Asn Ile Ala Met Ile<br>                        915                        920                        925 | 2784 |
| cat gcg gca gat aaa cgt gtt cat aga atc cga gaa gcg tac ctt cca<br>His Ala Ala Asp Lys Arg Val His Arg Ile Arg Glu Ala Tyr Leu Pro<br>930                        935                        940 | 2832 |
| gag tta tct gtg att ccg ggt gta aat gca gac att tcc gaa gaa tta<br>Glu Leu Ser Val Ile Pro Gly Val Asn Ala Asp Ile Ser Glu Glu Leu<br>945                        950                        955                        960 | 2880 |
| gaa ggg cgt att ttc act gca ttc tct cta tat gat gcg aga aat gtc<br>Glu Gly Arg Ile Phe Thr Ala Phe Ser Leu Tyr Asp Ala Arg Asn Val<br>                        965                        970                        975 | 2928 |
| att aaa aat ggc gat ttc aat aat ggc tta tta tgc tgg aac gtg aaa<br>Ile Lys Asn Gly Asp Phe Asn Asn Gly Leu Leu Cys Trp Asn Val Lys<br>        980                        985                        990 | 2976 |
| ggg cat gta gat gta gaa gaa caa  aat aac cac cgt tcg  gtc ctt gtt<br>Gly His Val Asp Val Glu Glu Gln Asn Asn His Arg Ser  Val Leu Val<br>                        995                        1000                   1005 | 3024 |
| gtt ccg  gaa tgg gaa gca gaa  gtg tca caa gag gtt  cgt gtc tgt<br>Val Pro Glu Trp Glu Ala Glu Val Ser Gln Glu Val Arg Val Cys<br>        1010                        1015                        1020 | 3069 |
| ccg ggg  cgt ggc tat atc ctt  cgt gtc aca gcg tac  aag gag gga<br>Pro Gly Arg Gly Tyr Ile Leu Arg Val Thr Ala Tyr Lys Glu Gly<br>     1025                        1030                        1035 | 3114 |
| tat gga  gaa ggt tgc gta acc  att cat gag atc gag  aac aat aca<br>Tyr Gly Glu Gly Cys Val Thr Ile His Glu Ile Glu Asn Asn Thr<br>        1040                        1045                        1050 | 3159 |

-continued

```
gac gaa ctg aag ttt agc aac tgt gta gaa gag gaa gtc tat cca    3204
Asp Glu Leu Lys Phe Ser Asn Cys Val Glu Glu Glu Val Tyr Pro
    1055                1060                1065 aac aac acg gta acg tgt aat gat tat act gca aat caa gaa gaa    3249
Asn Asn Thr Val Thr Cys Asn Asp Tyr Thr Ala Asn Gln Glu Glu
            1070                1075                1080 tat gag ggt acg tac act tct cgt aat cga gga tat gac gaa gcc    3294
Tyr Glu Gly Thr Tyr Thr Ser Arg Asn Arg Gly Tyr Asp Glu Ala
1085                1090                1095 tat gaa agc aat tct tct gta cca gct gag tat gcg tca gtc tat    3339
Tyr Glu Ser Asn Ser Ser Val Pro Ala Glu Tyr Ala Ser Val Tyr
    1100                1105                1110 gaa gaa aaa gtg tat aca gat gga cga aga ggg aat cct tgt gaa    3384
Glu Glu Lys Val Tyr Thr Asp Gly Arg Arg Gly Asn Pro Cys Glu
            1115                1120                1125 tct aac aga gga tat ggg gat tac aca cca cta cca gct ggc tat    3429
Ser Asn Arg Gly Tyr Gly Asp Tyr Thr Pro Leu Pro Ala Gly Tyr
1130                1135                1140 gtg aca aaa gaa tta gag tac ttc cca gaa acc gat aag gta tgg    3474
Val Thr Lys Glu Leu Glu Tyr Phe Pro Glu Thr Asp Lys Val Trp
    1145                1150                1155 att gag att gga gaa aca gaa gga aca ttc att gtg gat agt gtg    3519
Ile Glu Ile Gly Glu Thr Glu Gly Thr Phe Ile Val Asp Ser Val
            1160                1165                1170 gaa tta ctc ctt atg gag gaa taa                                3543
Glu Leu Leu Leu Met Glu Glu
1175                1180

<210> SEQ ID NO 2
<211> LENGTH: 1180
<212> TYPE: PRT
<213> ORGANISM: Bacillus thuringiensis

<400> SEQUENCE: 2

Met Glu Glu Asn Asn Gln Asn Gln Cys Val Pro Tyr Asn Cys Leu Asn
1               5                   10                  15

Asn Pro Ala Ile Glu Ile Leu Glu Gly Asp Arg Ile Ser Val Gly Asn
            20                  25                  30

Thr Pro Ile Asp Ile Ser Leu Ser Leu Val Glu Leu Leu Ile Ser Glu
        35                  40                  45

Phe Val Pro Gly Gly Gly Ile Ile Thr Gly Leu Leu Asn Ile Val Trp
    50                  55                  60

Gly Phe Val Gly Pro Ser Gln Trp Asp Ala Phe Leu Ala Gln Val Glu
65                  70                  75                  80

Gln Leu Ile Asn Gln Arg Ile Ser Glu Ala Val Arg Asn Thr Ala Ile
                85                  90                  95

Gln Glu Leu Glu Gly Met Ala Arg Val Tyr Arg Thr Tyr Ala Thr Ala
            100                 105                 110

Phe Ala Glu Trp Glu Arg Asp Pro Asn Asn Thr Asp Leu Arg Glu Ala
        115                 120                 125

Val Arg Thr Gln Phe Thr Ala Thr Glu Thr Tyr Ile Ser Gly Arg Ile
    130                 135                 140

Ser Val Leu Lys Ile Gln Asn Phe Glu Val Gln Leu Leu Ser Val Phe
145                 150                 155                 160

Ala Gln Ala Ala Asn Leu His Leu Ser Leu Leu Arg Asp Val Val Phe
                165                 170                 175

Phe Gly Gln Arg Trp Gly Phe Ser Thr Thr Thr Val Asn Asn Tyr Tyr
```

```
            180                 185                 190
Asn Asp Leu Thr Glu Glu Ile Ser Thr Tyr Thr Asp Tyr Ala Val Arg
        195                 200                 205

Trp Tyr Asn Thr Gly Leu Glu Arg Val Trp Gly Pro Asp Ser Arg Asp
    210                 215                 220

Trp Val Arg Tyr Asn Gln Phe Arg Arg Glu Leu Thr Leu Thr Val Leu
225                 230                 235                 240

Asp Ile Val Ala Leu Phe Pro Asn Tyr Asp Ser Arg Arg Tyr Pro Ile
            245                 250                 255

Arg Thr Val Ser Gln Leu Thr Arg Glu Ile Tyr Thr Asn Pro Val Leu
        260                 265                 270

Glu Asn Phe Asp Gly Ser Phe Arg Gly Met Ala Gln Arg Ile Glu Gln
    275                 280                 285

Asn Ile Arg Gln Pro His Leu Met Asp Ile Leu Asn Ser Ile Thr Ile
        290                 295                 300

Tyr Thr Asp Val His Arg Gly Phe Asn Tyr Trp Ser Gly His Gln Ile
305                 310                 315                 320

Thr Ala Ser Pro Val Gly Phe Ser Gly Pro Glu Phe Ala Phe Pro Leu
            325                 330                 335

Phe Gly Asn Ala Gly Asn Ala Ala Pro Val Leu Val Ser Leu Thr
        340                 345                 350

Gly Leu Gly Ile Phe Arg Thr Leu Ser Ser Pro Leu Tyr Arg Arg Ile
    355                 360                 365

Ile Leu Gly Ser Gly Pro Asn Asn Gln Glu Leu Phe Val Leu Asp Gly
        370                 375                 380

Thr Glu Phe Ser Phe Ala Ser Leu Thr Thr Asn Leu Pro Ser Thr Ile
385                 390                 395                 400

Tyr Arg Gln Arg Gly Thr Val Asp Ser Leu Asp Val Ile Pro Pro Gln
            405                 410                 415

Asp Asn Ser Val Pro Pro Arg Ala Gly Phe Ser His Arg Leu Ser His
        420                 425                 430

Val Thr Met Leu Ser Gln Ala Ala Gly Ala Val Tyr Thr Leu Arg Ala
    435                 440                 445

Pro Thr Phe Ser Trp Gln His Arg Ser Ala Thr Thr Asn Ile Ile
        450                 455                 460

Ala Ala Asp Ser Ile Thr Gln Ile Pro Ala Val Lys Gly Arg Ser Ile
465                 470                 475                 480

Ile Asn Asn Gly Thr Val Ile Ser Gly Pro Gly Phe Thr Gly Gly Asp
            485                 490                 495

Leu Val Arg Leu Tyr Asn Ala Asp Phe Asn Ile Asn Asn Arg Ala Tyr
        500                 505                 510

Leu Glu Val Pro Ile Phe Phe Gln Ser Pro Ser Thr Asn Tyr Arg Val
    515                 520                 525

Arg Val Arg Tyr Ala Ser Thr Ser Ser Leu Pro Val Asp Val Val Phe
        530                 535                 540

Gly Asn Ile Ser His Pro Thr Thr Phe Pro Ala Thr Ala Arg Ser Leu
545                 550                 555                 560

Asp Asn Leu Gln Ser Asn Asp Phe Gly Tyr Ile Asp Ile Ala Gly Thr
            565                 570                 575

Phe Leu Pro Ser Leu Gly Pro Ser Ile Gly Ile Arg Pro Met Leu Ser
        580                 585                 590

Thr Ile Asn Leu Ile Val Asp Arg Phe Glu Phe Ile Pro Val Thr Ala
    595                 600                 605
```

```
Thr Phe Glu Ala Glu Ser Asp Leu Glu Arg Ala Gln Lys Ala Val Asn
    610                 615                 620
Ala Leu Phe Thr Ser Thr Asn Gln Leu Gly Ile Lys Thr Asp Val Thr
625                 630                 635                 640
Asp Tyr His Ile Asp Gln Val Ser Asn Leu Val Glu Cys Leu Ser Asp
                645                 650                 655
Glu Phe Tyr Leu Asp Glu Lys Arg Glu Leu Ser Glu Lys Val Lys His
            660                 665                 670
Ala Lys Arg Leu Ser Asp Glu Arg Asn Leu Leu Gln Asp Pro Asn Phe
        675                 680                 685
Arg Gly Ile Asn Arg Gln Pro Asp Arg Gly Trp Arg Gly Ser Thr Asp
690                 695                 700
Ile Thr Ile Gln Gly Gly Asp Asp Val Phe Lys Glu Asn Tyr Val Thr
705                 710                 715                 720
Leu Pro Gly Thr Phe Asp Glu Cys Tyr Pro Thr Tyr Leu Tyr Gln Lys
                725                 730                 735
Ile Asp Glu Ser Lys Leu Lys Ala Tyr Thr Arg Tyr Gln Leu Arg Gly
            740                 745                 750
Tyr Ile Glu Asp Ser Gln Asp Leu Glu Ile Tyr Leu Ile Arg Tyr Asn
        755                 760                 765
Ala Lys His Glu Thr Val Asn Val Pro Gly Thr Gly Ser Leu Trp Pro
770                 775                 780
Leu Ser Ala Gln Ser Pro Ile Gly Lys Cys Gly Glu Pro Asn Arg Cys
785                 790                 795                 800
Ala Pro His Leu Glu Trp Asn Pro Asp Leu His Cys Ser Cys Arg Asp
                805                 810                 815
Gly Glu Lys Cys Ala His His Ser His His Phe Ser Leu Asp Ile Asp
            820                 825                 830
Val Gly Cys Thr Asp Leu Asn Glu Asp Leu Gly Val Trp Val Ile Phe
        835                 840                 845
Lys Ile Lys Thr Gln Asp Gly His Ala Arg Leu Gly Asn Leu Glu Phe
850                 855                 860
Leu Glu Glu Lys Pro Leu Val Gly Glu Ala Leu Ala Arg Val Lys Arg
865                 870                 875                 880
Ala Glu Lys Lys Trp Arg Asp Lys Arg Glu Lys Leu Gln Leu Glu Thr
                885                 890                 895
Asn Ile Val Tyr Lys Glu Ala Lys Glu Ser Val Asp Ala Leu Phe Val
            900                 905                 910
Asn Ser Gln Tyr Asp Gln Leu Gln Ala Asp Thr Asn Ile Ala Met Ile
        915                 920                 925
His Ala Ala Asp Lys Arg Val His Arg Ile Arg Glu Ala Tyr Leu Pro
930                 935                 940
Glu Leu Ser Val Ile Pro Gly Val Asn Ala Asp Ile Ser Glu Glu Leu
945                 950                 955                 960
Glu Gly Arg Ile Phe Thr Ala Phe Ser Leu Tyr Asp Ala Arg Asn Val
                965                 970                 975
Ile Lys Asn Gly Asp Phe Asn Asn Gly Leu Leu Cys Trp Asn Val Lys
            980                 985                 990
Gly His Val Asp Val Glu Glu Gln Asn Asn His Arg Ser Val Leu Val
        995                 1000                1005
Val Pro Glu Trp Glu Ala Glu Val Ser Gln Glu Val Arg Val Cys
    1010                1015                1020
```

```
Pro Gly  Arg Gly Tyr Ile Leu  Arg Val Thr Ala Tyr  Lys Glu Gly
    1025                 1030                 1035

Tyr Gly  Glu Gly Cys Val Thr  Ile His Glu Ile Glu  Asn Asn Thr
    1040                 1045                 1050

Asp Glu  Leu Lys Phe Ser Asn  Cys Val Glu Glu Glu  Val Tyr Pro
    1055                 1060                 1065

Asn Asn  Thr Val Thr Cys Asn  Asp Tyr Thr Ala Asn  Gln Glu Glu
    1070                 1075                 1080

Tyr Glu  Gly Thr Tyr Thr Ser  Arg Asn Arg Gly Tyr  Asp Glu Ala
    1085                 1090                 1095

Tyr Glu  Ser Asn Ser Ser Val  Pro Ala Glu Tyr Ala  Ser Val Tyr
    1100                 1105                 1110

Glu Glu  Lys Val Tyr Thr Asp  Gly Arg Arg Gly Asn  Pro Cys Glu
    1115                 1120                 1125

Ser Asn  Arg Gly Tyr Gly Asp  Tyr Thr Pro Leu Pro  Ala Gly Tyr
    1130                 1135                 1140

Val Thr  Lys Glu Leu Glu Tyr  Phe Pro Glu Thr Asp  Lys Val Trp
    1145                 1150                 1155

Ile Glu  Ile Gly Glu Thr Glu  Gly Thr Phe Ile Val  Asp Ser Val
    1160                 1165                 1170

Glu Leu  Leu Leu Met Glu Glu
    1175                 1180

<210> SEQ ID NO 3
<211> LENGTH: 3534
<212> TYPE: DNA
<213> ORGANISM: Artificial Sequence
<220> FEATURE:
<223> OTHER INFORMATION: Fully synthetic DNA encoding BCW 002
<220> FEATURE:
<221> NAME/KEY: CDS
<222> LOCATION: (1)..(3531)

<400> SEQUENCE: 3 atg gat aac aat ccg aac atc aat gaa tgc att cct tat aat tgt tta       48
Met Asp Asn Asn Pro Asn Ile Asn Glu Cys Ile Pro Tyr Asn Cys Leu
1               5                   10                  15 agt aac cct gaa gta gaa gta tta ggt gga gaa aga ata gaa act ggt       96
Ser Asn Pro Glu Val Glu Val Leu Gly Gly Glu Arg Ile Glu Thr Gly
            20                  25                  30 tac acc cca atc gat att tcc ttg tcg cta acg caa ttt ctt ttg agt      144
Tyr Thr Pro Ile Asp Ile Ser Leu Ser Leu Thr Gln Phe Leu Leu Ser
        35                  40                  45 gaa ttt gtt ccc ggt gct gga ttt gtg tta gga cta gtt gat ata ata      192
Glu Phe Val Pro Gly Ala Gly Phe Val Leu Gly Leu Val Asp Ile Ile
    50                  55                  60 tgg gga att ttt ggt ccc tct caa tgg gac gca ttt ctt gta caa att      240
Trp Gly Ile Phe Gly Pro Ser Gln Trp Asp Ala Phe Leu Val Gln Ile
65                  70                  75                  80 gaa cag tta att aac caa aga ata gaa gaa ttc gct agg aac caa gcc      288
Glu Gln Leu Ile Asn Gln Arg Ile Glu Glu Phe Ala Arg Asn Gln Ala
                85                  90                  95 att tct aga tta gaa gga cta agc aat ctt tat caa att tac gca gaa      336
Ile Ser Arg Leu Glu Gly Leu Ser Asn Leu Tyr Gln Ile Tyr Ala Glu
            100                 105                 110 tct ttt aga gag tgg gaa gca gat cct act aat cca gca tta aga gaa      384
Ser Phe Arg Glu Trp Glu Ala Asp Pro Thr Asn Pro Ala Leu Arg Glu
        115                 120                 125 gag atg cgt att caa ttc aat gac atg aac agt gcc ctt aca acc gct      432
```

-continued

|     |     |     |     |     |     |     |     |     |     |     |     |     |     |     |
| --- | --- | --- | --- | --- | --- | --- | --- | --- | --- | --- | --- | --- | --- | --- |
| Glu | Met | Arg | Ile | Gln | Phe | Asn | Asp | Met | Asn | Ser | Ala | Leu | Thr | Thr | Ala |
|     | 130 |     |     |     | 135 |     |     |     | 140 |     |     |     |     |     |

```
att cct ctt ttg gca gtt caa aat tat caa gtt cct ctt tta tca gta     480
Ile Pro Leu Leu Ala Val Gln Asn Tyr Gln Val Pro Leu Leu Ser Val
145                 150                 155                 160 tat gtt caa gct gca aat tta cat tta tca gtt ttg aga gat gtt tca     528
Tyr Val Gln Ala Ala Asn Leu His Leu Ser Val Leu Arg Asp Val Ser
            165                 170                 175 gtg ttt gga caa agg tgg gga ttt gat gcc gcg act atc aat agt cgt     576
Val Phe Gly Gln Arg Trp Gly Phe Asp Ala Ala Thr Ile Asn Ser Arg
        180                 185                 190 tat aat gat tta act agg ctt att ggc aac tat aca gat tat gct gta     624
Tyr Asn Asp Leu Thr Arg Leu Ile Gly Asn Tyr Thr Asp Tyr Ala Val
    195                 200                 205 cgc tgg tac aat acg gga tta gaa cgt gta tgg gga ccg gat tct aga     672
Arg Trp Tyr Asn Thr Gly Leu Glu Arg Val Trp Gly Pro Asp Ser Arg
210                 215                 220 gat tgg gta agg tat aat caa ttt aga aga gaa tta aca cta act gta     720
Asp Trp Val Arg Tyr Asn Gln Phe Arg Arg Glu Leu Thr Leu Thr Val
225                 230                 235                 240 tta gat atc gtt gct ctg ttc ccg aat tat gat agt aga aga tat cca     768
Leu Asp Ile Val Ala Leu Phe Pro Asn Tyr Asp Ser Arg Arg Tyr Pro
                245                 250                 255 att cga ata gtt tcc caa tta aca aga gaa att tat acg aac cca gta     816
Ile Arg Ile Val Ser Gln Leu Thr Arg Glu Ile Tyr Thr Asn Pro Val
            260                 265                 270 tta gaa aat ttt gat ggt agt ttt cgt gga atg gct cag aga ata gaa     864
Leu Glu Asn Phe Asp Gly Ser Phe Arg Gly Met Ala Gln Arg Ile Glu
        275                 280                 285 cag aat att agg caa cca cat ctt atg gat atc ctt aat agt ata acc     912
Gln Asn Ile Arg Gln Pro His Leu Met Asp Ile Leu Asn Ser Ile Thr
    290                 295                 300 att tat act gat gtg cat aga ggc ttt aat tat tgg tca ggg cat caa     960
Ile Tyr Thr Asp Val His Arg Gly Phe Asn Tyr Trp Ser Gly His Gln
305                 310                 315                 320 ata aca gct tct cct gta ggg ttt tca gga cca gaa ttc gca ttc cct     1008
Ile Thr Ala Ser Pro Val Gly Phe Ser Gly Pro Glu Phe Ala Phe Pro
                325                 330                 335 tta ttt ggg aat gcg gga aat gca gct cca ccc gta ctt gtc tca tta     1056
Leu Phe Gly Asn Ala Gly Asn Ala Ala Pro Pro Val Leu Val Ser Leu
        340                 345                 350 act ggt ttg ggg att ttt aga aca tta tct tca cct tta tat aga aga     1104
Thr Gly Leu Gly Ile Phe Arg Thr Leu Ser Ser Pro Leu Tyr Arg Arg
    355                 360                 365 att ata ctt ggt tca ggc cca aat aat cag gaa ctg ttt gtc ctt gat     1152
Ile Ile Leu Gly Ser Gly Pro Asn Asn Gln Glu Leu Phe Val Leu Asp
370                 375                 380 gga acg gag ttt tct ttt gcc tcc cta acg acc aac ttg cct tcc act     1200
Gly Thr Glu Phe Ser Phe Ala Ser Leu Thr Thr Asn Leu Pro Ser Thr
385                 390                 395                 400 ata tat aga caa agg ggt aca gtc gat tca cta gat gta ata ccg cca     1248
Ile Tyr Arg Gln Arg Gly Thr Val Asp Ser Leu Asp Val Ile Pro Pro
                405                 410                 415 cag gat aat agt gta cca cct cgt gcg gga ttt agc cat cga ttg agt     1296
Gln Asp Asn Ser Val Pro Pro Arg Ala Gly Phe Ser His Arg Leu Ser
        420                 425                 430 cat gtt aca atg ctg agc caa gca gct gga gca gtt tac acc ttg aga     1344
His Val Thr Met Leu Ser Gln Ala Ala Gly Ala Val Tyr Thr Leu Arg
    435                 440                 445
```

```
gct cca acg ttt tct tgg cag cat cgc agt gct acg aca act aat ata    1392
Ala Pro Thr Phe Ser Trp Gln His Arg Ser Ala Thr Thr Asn Ile
450             455                 460 att gca gcg gat agt att act caa att cct gct gtt aaa gga cgt tct    1440
Ile Ala Ala Asp Ser Ile Thr Gln Ile Pro Ala Val Lys Gly Arg Ser
465             470                 475                 480 att att aat aat ggc acg gta att tca gga cca ggg ttt acc gga ggc    1488
Ile Ile Asn Asn Gly Thr Val Ile Ser Gly Pro Gly Phe Thr Gly Gly
                485                 490                 495 gat ttg gtt aga tta tac aat gct gat ttt aat att aat aat aga gca    1536
Asp Leu Val Arg Leu Tyr Asn Ala Asp Phe Asn Ile Asn Asn Arg Ala
            500                 505                 510 tac ctt gaa gtt ccg ata ttc ttc caa tca ccc tct aca aat tat cgt    1584
Tyr Leu Glu Val Pro Ile Phe Phe Gln Ser Pro Ser Thr Asn Tyr Arg
        515                 520                 525 gtt cgt gtt cgt tat gct tct aca tct tca ctc cct gta gat gta gtt    1632
Val Arg Val Arg Tyr Ala Ser Thr Ser Ser Leu Pro Val Asp Val Val
    530                 535                 540 ttc gga aat att agt cat cct act aca ttc cca gcc act gcc aga tca    1680
Phe Gly Asn Ile Ser His Pro Thr Thr Phe Pro Ala Thr Ala Arg Ser
545                 550                 555                 560 tta gat aat cta caa tcc aat gat ttt gga tat att gat att gct gga    1728
Leu Asp Asn Leu Gln Ser Asn Asp Phe Gly Tyr Ile Asp Ile Ala Gly
                565                 570                 575 act ttc tta cct tca cta ggg cct agt ata ggt atc aga cct atg tta    1776
Thr Phe Leu Pro Ser Leu Gly Pro Ser Ile Gly Ile Arg Pro Met Leu
            580                 585                 590 tct act att aat ttg ata gta gat aga ttt gaa ttt att cca gta act    1824
Ser Thr Ile Asn Leu Ile Val Asp Arg Phe Glu Phe Ile Pro Val Thr
        595                 600                 605 gca acc ttt gaa gca gaa tcg gat tta gaa aga gca caa aag gcg gtg    1872
Ala Thr Phe Glu Ala Glu Ser Asp Leu Glu Arg Ala Gln Lys Ala Val
    610                 615                 620 aat gcg ctg ttt act tct aca aac caa cta ggg ata aaa aca gat gtg    1920
Asn Ala Leu Phe Thr Ser Thr Asn Gln Leu Gly Ile Lys Thr Asp Val
625                 630                 635                 640 acg gat tat cat att gat caa gtg tcc aat tta gtg gag tgt tta tcg    1968
Thr Asp Tyr His Ile Asp Gln Val Ser Asn Leu Val Glu Cys Leu Ser
                645                 650                 655 gat gaa ttt tat ctg gat gaa aag cga gaa ttg tcc gag aaa gtc aaa    2016
Asp Glu Phe Tyr Leu Asp Glu Lys Arg Glu Leu Ser Glu Lys Val Lys
            660                 665                 670 cat gcg aag cga ctc agt gat gag cga aat tta ctt caa gat cca aac    2064
His Ala Lys Arg Leu Ser Asp Glu Arg Asn Leu Leu Gln Asp Pro Asn
        675                 680                 685 ttc agg ggc atc aat aga caa cca gat cgt ggc tgg aga gga agt acg    2112
Phe Arg Gly Ile Asn Arg Gln Pro Asp Arg Gly Trp Arg Gly Ser Thr
    690                 695                 700 gat att acc atc caa gga gga gat gac gta ttc aaa gag aat tac gtc    2160
Asp Ile Thr Ile Gln Gly Gly Asp Asp Val Phe Lys Glu Asn Tyr Val
705                 710                 715                 720 aca cta cca ggt acc ttt gat gag tgc tat cca aca tat ttg tat caa    2208
Thr Leu Pro Gly Thr Phe Asp Glu Cys Tyr Pro Thr Tyr Leu Tyr Gln
                725                 730                 735 aaa atc gat gaa tca aaa tta aaa gcc ttt acc cgt tat caa tta aga    2256
Lys Ile Asp Glu Ser Lys Leu Lys Ala Phe Thr Arg Tyr Gln Leu Arg
            740                 745                 750 ggg tat atc gaa gat agt caa gac tta gaa atc tat tta att cgc tac    2304
Gly Tyr Ile Glu Asp Ser Gln Asp Leu Glu Ile Tyr Leu Ile Arg Tyr
        755                 760                 765
```

```
aat gca aaa cat gaa aca gta aat gtg cca ggt acg ggt tcc tta tgg    2352
Asn Ala Lys His Glu Thr Val Asn Val Pro Gly Thr Gly Ser Leu Trp
    770             775                 780 ccg ctt tca gcc caa agt cca atc gga aag tgt gga gag ccg aat cga    2400
Pro Leu Ser Ala Gln Ser Pro Ile Gly Lys Cys Gly Glu Pro Asn Arg
785             790                 795                 800 tgc gcg cca cac ctt gaa tgg aat cct gac tta gat tgt tcg tgt agg    2448
Cys Ala Pro His Leu Glu Trp Asn Pro Asp Leu Asp Cys Ser Cys Arg
                805                 810                 815 gat gga gaa aag tgt gcc cat cat tcg cat cat ttc tcc tta gac att    2496
Asp Gly Glu Lys Cys Ala His His Ser His His Phe Ser Leu Asp Ile
            820                 825                 830 gat gta gga tgt aca gac tta aat gag gac cta ggt gta tgg gtg atc    2544
Asp Val Gly Cys Thr Asp Leu Asn Glu Asp Leu Gly Val Trp Val Ile
        835                 840                 845 ttt aag att aag acg caa gat ggg cac gca aga cta ggg aat cta gag    2592
Phe Lys Ile Lys Thr Gln Asp Gly His Ala Arg Leu Gly Asn Leu Glu
    850             855                 860 ttt ctc gaa gag aaa cca tta gta gga gaa gca cta gct cgt gtg aaa    2640
Phe Leu Glu Glu Lys Pro Leu Val Gly Glu Ala Leu Ala Arg Val Lys
865             870                 875                 880 aga gcg gag aaa aaa tgg aga gac aaa cgt gaa aaa ttg gaa tgg gaa    2688
Arg Ala Glu Lys Lys Trp Arg Asp Lys Arg Glu Lys Leu Glu Trp Glu
                885                 890                 895 aca aat atc gtt tat aaa gag gca aaa gaa tct gta gat gct tta ttt    2736
Thr Asn Ile Val Tyr Lys Glu Ala Lys Glu Ser Val Asp Ala Leu Phe
            900                 905                 910 gta aac tct caa tat gat caa tta caa gcg gat acg aat att gcc atg    2784
Val Asn Ser Gln Tyr Asp Gln Leu Gln Ala Asp Thr Asn Ile Ala Met
        915                 920                 925 att cat gcg gca gat aaa cgt gtt cat agc att cga gaa gct tat ctg    2832
Ile His Ala Ala Asp Lys Arg Val His Ser Ile Arg Glu Ala Tyr Leu
    930             935                 940 cct gag ctg tct gtg att ccg ggt gtc aat gcg gct att ttt gaa gaa    2880
Pro Glu Leu Ser Val Ile Pro Gly Val Asn Ala Ala Ile Phe Glu Glu
945             950                 955                 960 tta gaa ggg cgt att ttc act gca ttc tcc cta tat gat gcg aga aat    2928
Leu Glu Gly Arg Ile Phe Thr Ala Phe Ser Leu Tyr Asp Ala Arg Asn
                965                 970                 975 gtc att aaa aat ggt gat ttt aat aat ggc tta tcc tgc tgg aac gtg    2976
Val Ile Lys Asn Gly Asp Phe Asn Asn Gly Leu Ser Cys Trp Asn Val
            980                 985                 990 aaa ggg cat gta gat gta gaa gaa caa aac aac caa cgt tcg gtc ctt    3024
Lys Gly His Val Asp Val Glu Glu Gln Asn Asn Gln Arg Ser Val Leu
        995                 1000                1005 gtt gtt ccg gaa tgg gaa gca gaa gtg tca caa gaa gtt cgt gtc       3069
Val Val Pro Glu Trp Glu Ala Glu Val Ser Gln Glu Val Arg Val
    1010            1015                1020 tgt ccg ggt cgt ggc tat atc ctt cgt gtc aca gcg tac aag gag       3114
Cys Pro Gly Arg Gly Tyr Ile Leu Arg Val Thr Ala Tyr Lys Glu
1025            1030                1035 gga tat gga gaa ggt tgc gta acc att cat gag atc gag aac aat       3159
Gly Tyr Gly Glu Gly Cys Val Thr Ile His Glu Ile Glu Asn Asn
    1040            1045                1050 aca gac gaa ctg aag ttt agc aac tgc gta gaa gag gaa atc tat       3204
Thr Asp Glu Leu Lys Phe Ser Asn Cys Val Glu Glu Glu Ile Tyr
    1055            1060                1065 cca aat aac acg gta acg tgt aat gat tat act gta aat caa gaa       3249
Pro Asn Asn Thr Val Thr Cys Asn Asp Tyr Thr Val Asn Gln Glu
```

```
                1070                1075                1080
gaa  tac  gga  ggt  gcg  tac  act  tct  cgt  aat  cga  gga  tat  aac  gaa         3294
Glu  Tyr  Gly  Gly  Ala  Tyr  Thr  Ser  Arg  Asn  Arg  Gly  Tyr  Asn  Glu
     1085                1090                1095 gct  cct  tcc  gta  cca  gct  gat  tat  gcg  tca  gtc  tat  gaa  gaa  aaa         3339
Ala  Pro  Ser  Val  Pro  Ala  Asp  Tyr  Ala  Ser  Val  Tyr  Glu  Glu  Lys
     1100                1105                1110 tcg  tat  aca  gat  gga  cga  aga  gag  aat  cct  tgt  gaa  ttt  aac  aga         3384
Ser  Tyr  Thr  Asp  Gly  Arg  Arg  Glu  Asn  Pro  Cys  Glu  Phe  Asn  Arg
     1115                1120                1125 ggg  tat  agg  gat  tac  acg  cca  cta  cca  gtt  ggt  tat  gtg  aca  aaa         3429
Gly  Tyr  Arg  Asp  Tyr  Thr  Pro  Leu  Pro  Val  Gly  Tyr  Val  Thr  Lys
     1130                1135                1140 gaa  tta  gaa  tac  ttc  cca  gaa  acc  gat  aag  gta  tgg  att  gag  att         3474
Glu  Leu  Glu  Tyr  Phe  Pro  Glu  Thr  Asp  Lys  Val  Trp  Ile  Glu  Ile
     1145                1150                1155 gga  gaa  acg  gaa  gga  aca  ttt  atc  gtg  gac  agc  gtg  gaa  tta  ctc         3519
Gly  Glu  Thr  Glu  Gly  Thr  Phe  Ile  Val  Asp  Ser  Val  Glu  Leu  Leu
     1160                1165                1170 ctt  atg  gag  gaa  tag                                                           3534
Leu  Met  Glu  Glu
     1175

<210> SEQ ID NO 4
<211> LENGTH: 1177
<212> TYPE: PRT
<213> ORGANISM: Artificial Sequence
<220> FEATURE:
<223> OTHER INFORMATION: Synthetic Construct

<400> SEQUENCE: 4

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205
```

-continued

```
Arg Trp Tyr Asn Thr Gly Leu Glu Arg Val Trp Gly Pro Asp Ser Arg
    210                 215                 220
Asp Trp Val Arg Tyr Asn Gln Phe Arg Arg Glu Leu Thr Leu Thr Val
225                 230                 235                 240
Leu Asp Ile Val Ala Leu Phe Pro Asn Tyr Asp Ser Arg Arg Tyr Pro
                245                 250                 255
Ile Arg Ile Val Ser Gln Leu Thr Arg Glu Ile Tyr Thr Asn Pro Val
            260                 265                 270
Leu Glu Asn Phe Asp Gly Ser Phe Arg Gly Met Ala Gln Arg Ile Glu
            275                 280                 285
Gln Asn Ile Arg Gln Pro His Leu Met Asp Ile Leu Asn Ser Ile Thr
290                 295                 300
Ile Tyr Thr Asp Val His Arg Gly Phe Asn Tyr Trp Ser Gly His Gln
305                 310                 315                 320
Ile Thr Ala Ser Pro Val Gly Phe Ser Gly Pro Glu Phe Ala Phe Pro
                325                 330                 335
Leu Phe Gly Asn Ala Gly Asn Ala Ala Pro Pro Val Leu Val Ser Leu
            340                 345                 350
Thr Gly Leu Gly Ile Phe Arg Thr Leu Ser Ser Pro Leu Tyr Arg Arg
            355                 360                 365
Ile Ile Leu Gly Ser Gly Pro Asn Asn Gln Glu Leu Phe Val Leu Asp
            370                 375                 380
Gly Thr Glu Phe Ser Phe Ala Ser Leu Thr Thr Asn Leu Pro Ser Thr
385                 390                 395                 400
Ile Tyr Arg Gln Arg Gly Thr Val Asp Ser Leu Asp Val Ile Pro Pro
                405                 410                 415
Gln Asp Asn Ser Val Pro Pro Arg Ala Gly Phe Ser His Arg Leu Ser
            420                 425                 430
His Val Thr Met Leu Ser Gln Ala Ala Gly Ala Val Tyr Thr Leu Arg
            435                 440                 445
Ala Pro Thr Phe Ser Trp Gln His Arg Ser Ala Thr Thr Thr Asn Ile
            450                 455                 460
Ile Ala Ala Asp Ser Ile Thr Gln Ile Pro Ala Val Lys Gly Arg Ser
465                 470                 475                 480
Ile Ile Asn Asn Gly Thr Val Ile Ser Gly Pro Gly Phe Thr Gly Gly
                485                 490                 495
Asp Leu Val Arg Leu Tyr Asn Ala Asp Phe Asn Ile Asn Asn Arg Ala
            500                 505                 510
Tyr Leu Glu Val Pro Ile Phe Phe Gln Ser Pro Ser Thr Asn Tyr Arg
            515                 520                 525
Val Arg Val Arg Tyr Ala Ser Thr Ser Ser Leu Pro Val Asp Val Val
            530                 535                 540
Phe Gly Asn Ile Ser His Pro Thr Thr Phe Pro Ala Thr Ala Arg Ser
545                 550                 555                 560
Leu Asp Asn Leu Gln Ser Asn Asp Phe Gly Tyr Ile Asp Ile Ala Gly
                565                 570                 575
Thr Phe Leu Pro Ser Leu Gly Pro Ser Ile Gly Ile Arg Pro Met Leu
            580                 585                 590
Ser Thr Ile Asn Leu Ile Val Asp Arg Phe Glu Phe Ile Pro Val Thr
            595                 600                 605
Ala Thr Phe Glu Ala Glu Ser Asp Leu Glu Arg Ala Gln Lys Ala Val
            610                 615                 620
Asn Ala Leu Phe Thr Ser Thr Asn Gln Leu Gly Ile Lys Thr Asp Val
```

-continued

```
            625                 630                 635                 640
    Thr Asp Tyr His Ile Asp Gln Val Ser Asn Leu Val Glu Cys Leu Ser
                        645                 650                 655

Asp Glu Phe Tyr Leu Asp Glu Lys Arg Glu Leu Ser Glu Lys Val Lys
                        660                 665                 670

His Ala Lys Arg Leu Ser Asp Glu Arg Asn Leu Leu Gln Asp Pro Asn
                        675                 680                 685

Phe Arg Gly Ile Asn Arg Gln Pro Asp Arg Gly Trp Arg Gly Ser Thr
                        690                 695                 700

Asp Ile Thr Ile Gln Gly Gly Asp Val Phe Lys Glu Asn Tyr Val
    705                 710                 715                 720

Thr Leu Pro Gly Thr Phe Asp Glu Cys Tyr Pro Thr Tyr Leu Tyr Gln
                        725                 730                 735

Lys Ile Asp Glu Ser Lys Leu Lys Ala Phe Thr Arg Tyr Gln Leu Arg
                        740                 745                 750

Gly Tyr Ile Glu Asp Ser Gln Asp Leu Glu Ile Tyr Leu Ile Arg Tyr
                        755                 760                 765

Asn Ala Lys His Glu Thr Val Asn Val Pro Gly Thr Gly Ser Leu Trp
    770                 775                 780

Pro Leu Ser Ala Gln Ser Pro Ile Gly Lys Cys Gly Glu Pro Asn Arg
    785                 790                 795                 800

Cys Ala Pro His Leu Glu Trp Asn Pro Asp Leu Asp Cys Ser Cys Arg
                        805                 810                 815

Asp Gly Glu Lys Cys Ala His His Ser His His Phe Ser Leu Asp Ile
                        820                 825                 830

Asp Val Gly Cys Thr Asp Leu Asn Glu Asp Leu Gly Val Trp Val Ile
                        835                 840                 845

Phe Lys Ile Lys Thr Gln Asp Gly His Ala Arg Leu Gly Asn Leu Glu
                        850                 855                 860

Phe Leu Glu Glu Lys Pro Leu Val Gly Glu Ala Leu Ala Arg Val Lys
    865                 870                 875                 880

Arg Ala Glu Lys Lys Trp Arg Asp Lys Arg Glu Lys Leu Glu Trp Glu
                        885                 890                 895

Thr Asn Ile Val Tyr Lys Glu Ala Lys Glu Ser Val Asp Ala Leu Phe
                        900                 905                 910

Val Asn Ser Gln Tyr Asp Gln Leu Gln Ala Asp Thr Asn Ile Ala Met
                        915                 920                 925

Ile His Ala Ala Asp Lys Arg Val His Ser Ile Arg Glu Ala Tyr Leu
                        930                 935                 940

Pro Glu Leu Ser Val Ile Pro Gly Val Asn Ala Ala Ile Phe Glu Glu
    945                 950                 955                 960

Leu Glu Gly Arg Ile Phe Thr Ala Phe Ser Leu Tyr Asp Ala Arg Asn
                        965                 970                 975

Val Ile Lys Asn Gly Asp Phe Asn Asn Gly Leu Ser Cys Trp Asn Val
                        980                 985                 990

Lys Gly His Val Asp Val Glu Glu  Gln Asn Asn Gln Arg Ser Val Leu
                        995                 1000                1005

Val Val  Pro Glu Trp Glu Ala  Glu Val Ser Gln Glu  Val Arg Val
    1010                1015                1020

Cys Pro  Gly Arg Gly Tyr Ile  Leu Arg Val Thr Ala  Tyr Lys Glu
    1025                1030                1035

Gly Tyr  Gly Glu Gly Cys Val  Thr Ile His Glu Ile  Glu Asn Asn
    1040                1045                1050
```

```
Thr Asp Glu Leu Lys Phe Ser Asn Cys Val Glu  Glu Ile Tyr
    1055                1060                 1065

Pro Asn Asn Thr Val Thr Cys Asn Asp Tyr Thr Val  Asn Gln Glu
    1070                1075                1080

Glu Tyr Gly Gly Ala Tyr Thr Ser Arg Asn Arg Gly  Tyr Asn Glu
    1085                1090                1095

Ala Pro Ser Val Pro Ala Asp Tyr Ala Ser Val Tyr  Glu Glu Lys
    1100                1105                1110

Ser Tyr Thr Asp Gly Arg Arg Glu Asn Pro Cys Glu  Phe Asn Arg
    1115                1120                1125

Gly Tyr Arg Asp Tyr Thr Pro Leu Pro Val Gly Tyr  Val Thr Lys
    1130                1135                1140

Glu Leu Glu Tyr Phe Pro Glu Thr Asp Lys Val Trp  Ile Glu Ile
    1145                1150                1155

Gly Glu Thr Glu Gly Thr Phe Ile Val Asp Ser Val  Glu Leu Leu
    1160                1165                1170

Leu Met Glu Glu
    1175

<210> SEQ ID NO 5
<211> LENGTH: 3534
<212> TYPE: DNA
<213> ORGANISM: Artificial Sequence
<220> FEATURE:
<223> OTHER INFORMATION: Fully synthetic sequence encoding BCW 003
<220> FEATURE:
<221> NAME/KEY: CDS
<222> LOCATION: (1)..(3531)

<400> SEQUENCE: 5 atg gat aac aat ccg aac atc aat gaa tgc att cct tat aat tgt tta         48
Met Asp Asn Asn Pro Asn Ile Asn Glu Cys Ile Pro Tyr Asn Cys Leu
1               5                   10                  15 agt aac cct gaa gta gaa gta tta ggt gga gaa aga

```
              145                 150                 155                 160
         tat gtt caa gct gca aat tta cat tta tca gtt ttg aga gat gtt tca     528
         Tyr Val Gln Ala Ala Asn Leu His Leu Ser Val Leu Arg Asp Val Ser
                         165                 170                 175 gtg ttt gga caa agg tgg gga ttt gat gcc gcg act atc aat agt cgt     576
         Val Phe Gly Gln Arg Trp Gly Phe Asp Ala Ala Thr Ile Asn Ser Arg
                 180                 185                 190 tat aat gat tta act agg ctt att ggc aac tat aca gat tat gct gta     624
         Tyr Asn Asp Leu Thr Arg Leu Ile Gly Asn Tyr Thr Asp Tyr Ala Val
                     195                 200                 205 cgc tgg tac aat acg gga tta gaa cgt gta tgg gga ccg gat tct aga     672
         Arg Trp Tyr Asn Thr Gly Leu Glu Arg Val Trp Gly Pro Asp Ser Arg
             210                 215                 220 gat tgg gta agg tat aat caa ttt aga aga gaa tta aca cta act gta     720
         Asp Trp Val Arg Tyr Asn Gln Phe Arg Arg Glu Leu Thr Leu Thr Val
         225                 230                 235                 240 tta gat atc gtt gct ctg ttc ccg aat tat gat agt aga aga tat cca     768
         Leu Asp Ile Val Ala Leu Phe Pro Asn Tyr Asp Ser Arg Arg Tyr Pro
                         245                 250                 255 att cga aca gtt tcc caa tta aca aga gaa att tat acg aac cca gta     816
         Ile Arg Thr Val Ser Gln Leu Thr Arg Glu Ile Tyr Thr Asn Pro Val
                 260                 265                 270 tta gaa aat ttt gat ggt agt ttt cgt gga atg gct cag aga ata gaa     864
         Leu Glu Asn Phe Asp Gly Ser Phe Arg Gly Met Ala Gln Arg Ile Glu
                     275                 280                 285 cag aat att agg caa cca cat ctt atg gat atc ctt aat agt ata acc     912
         Gln Asn Ile Arg Gln Pro His Leu Met Asp Ile Leu Asn Ser Ile Thr
             290                 295                 300 att tat act gat gtg cat aga ggc ttt aat tat tgg tca ggg cat caa     960
         Ile Tyr Thr Asp Val His Arg Gly Phe Asn Tyr Trp Ser Gly His Gln
         305                 310                 315                 320 ata aca gct tct cct gta ggg ttt tca gga cca gaa ttc gca ttc cct    1008
         Ile Thr Ala Ser Pro Val Gly Phe Ser Gly Pro Glu Phe Ala Phe Pro
                         325                 330                 335 tta ttt ggg aat gcg gga aat gca gct cca ccc gta ctt gtc tca tta    1056
         Leu Phe Gly Asn Ala Gly Asn Ala Ala Pro Pro Val Leu Val Ser Leu
                 340                 345                 350 act ggt ttg ggg att ttt aga aca tta tct tca cct tta tat aga aga    1104
         Thr Gly Leu Gly Ile Phe Arg Thr Leu Ser Ser Pro Leu Tyr Arg Arg
                     355                 360                 365 att ata ctt ggt tca ggc cca aat aat cag gaa ctg ttt gtc ctt gat    1152
         Ile Ile Leu Gly Ser Gly Pro Asn Asn Gln Glu Leu Phe Val Leu Asp
             370                 375                 380 gga acg gag ttt tct ttt gcc tcc cta acg acc aac ttg cct tcc act    1200
         Gly Thr Glu Phe Ser Phe Ala Ser Leu Thr Thr Asn Leu Pro Ser Thr
         385                 390                 395                 400 ata tat aga caa agg ggt aca gtc gat tca cta gat gta ata ccg cca    1248
         Ile Tyr Arg Gln Arg Gly Thr Val Asp Ser Leu Asp Val Ile Pro Pro
                         405                 410                 415 cag gat aat agt gta cca cct cgt gcg gga ttt agc cat cga ttg agt    1296
         Gln Asp Asn Ser Val Pro Pro Arg Ala Gly Phe Ser His Arg Leu Ser
                 420                 425                 430 cat gtt aca atg ctg agc caa gca gct gga gca gtt tac acc ttg aga    1344
         His Val Thr Met Leu Ser Gln Ala Ala Gly Ala Val Tyr Thr Leu Arg
                     435                 440                 445 gct cca acg ttt tct tgg cag cat cgc agt gct acg aca act aat ata    1392
         Ala Pro Thr Phe Ser Trp Gln His Arg Ser Ala Thr Thr Thr Asn Ile
             450                 455                 460 att gca gcg gat agt att act caa att cct gct gtt aaa gga cgt tct    1440
```

```
Ile Ala Ala Asp Ser Ile Thr Gln Ile Pro Ala Val Lys Gly Arg Ser
465                 470                 475                 480 att att aat aat ggc acg gta att tca gga cca ggg ttt acc gga ggc      1488
Ile Ile Asn Asn Gly Thr Val Ile Ser Gly Pro Gly Phe Thr Gly Gly
                    485                 490                 495 gat ttg gtt aga tta tac aat gct gat ttt aat att aat aat aga gca      1536
Asp Leu Val Arg Leu Tyr Asn Ala Asp Phe Asn Ile Asn Asn Arg Ala
                500                 505                 510 tac ctt gaa gtt ccg ata ttc ttc caa tca ccc tct aca aat tat cgt      1584
Tyr Leu Glu Val Pro Ile Phe Phe Gln Ser Pro Ser Thr Asn Tyr Arg
            515                 520                 525 gtt cgt gtt cgt tat gct tct aca tct tca ctc cct gta gat gta gtt      1632
Val Arg Val Arg Tyr Ala Ser Thr Ser Ser Leu Pro Val Asp Val Val
            530                 535                 540 ttc gga aat att agt cat cct act aca ttc cca gcc act gcc aga tca      1680
Phe Gly Asn Ile Ser His Pro Thr Thr Phe Pro Ala Thr Ala Arg Ser
545                 550                 555                 560 tta gat aat cta caa tcc aat gat ttt gga tat att gat att gct gga      1728
Leu Asp Asn Leu Gln Ser Asn Asp Phe Gly Tyr Ile Asp Ile Ala Gly
                565                 570                 575 act ttc tta cct tca cta ggg cct agt ata ggt atc aga cct atg tta      1776
Thr Phe Leu Pro Ser Leu Gly Pro Ser Ile Gly Ile Arg Pro Met Leu
            580                 585                 590 tct act att aat ttg ata gta gat aga ttt gaa ttt att cca gta act      1824
Ser Thr Ile Asn Leu Ile Val Asp Arg Phe Glu Phe Ile Pro Val Thr
            595                 600                 605 gca acc ttt gaa gca gaa tcg gat tta gaa aga gca caa aag gcg gtg      1872
Ala Thr Phe Glu Ala Glu Ser Asp Leu Glu Arg Ala Gln Lys Ala Val
610                 615                 620 aat gcg ctg ttt act tct aca aac caa cta ggg ata aaa aca gat gtg      1920
Asn Ala Leu Phe Thr Ser Thr Asn Gln Leu Gly Ile Lys Thr Asp Val
625                 630                 635                 640 acg gat tat cat att gat caa gtg tcc aat tta gtg gag tgt tta tcg      1968
Thr Asp Tyr His Ile Asp Gln Val Ser Asn Leu Val Glu Cys Leu Ser
                645                 650                 655 gat gaa ttt tat ctg gat gaa aag cga gaa ttg tcc gag aaa gtc aaa      2016
Asp Glu Phe Tyr Leu Asp Glu Lys Arg Glu Leu Ser Glu Lys Val Lys
            660                 665                 670 cat gcg aag cga ctc agt gat gag cga aat tta ctt caa gat cca aac      2064
His Ala Lys Arg Leu Ser Asp Glu Arg Asn Leu Leu Gln Asp Pro Asn
            675                 680                 685 ttc agg ggc atc aat aga caa cca gat cgt ggc tgg aga gga agt acg      2112
Phe Arg Gly Ile Asn Arg Gln Pro Asp Arg Gly Trp Arg Gly Ser Thr
690                 695                 700 gat att acc atc caa gga gga gat gac gta ttc aaa gag aat tac gtc      2160
Asp Ile Thr Ile Gln Gly Gly Asp Asp Val Phe Lys Glu Asn Tyr Val
705                 710                 715                 720 aca cta cca ggt acc ttt gat gag tgc tat cca aca tat ttg tat caa      2208
Thr Leu Pro Gly Thr Phe Asp Glu Cys Tyr Pro Thr Tyr Leu Tyr Gln
                725                 730                 735 aaa atc gat gaa tca aaa tta aaa gcc ttt acc cgt tat caa tta aga      2256
Lys Ile Asp Glu Ser Lys Leu Lys Ala Phe Thr Arg Tyr Gln Leu Arg
            740                 745                 750 ggg tat atc gaa gat agt caa gac tta gaa atc tat tta att cgc tac      2304
Gly Tyr Ile Glu Asp Ser Gln Asp Leu Glu Ile Tyr Leu Ile Arg Tyr
            755                 760                 765 aat gca aaa cat gaa aca gta aat gtg cca ggt acg ggt tcc tta tgg      2352
Asn Ala Lys His Glu Thr Val Asn Val Pro Gly Thr Gly Ser Leu Trp
770                 775                 780
```

-continued

| | |
|---|---|
| ccg ctt tca gcc caa agt cca atc gga aag tgt gga gag ccg aat cga<br>Pro Leu Ser Ala Gln Ser Pro Ile Gly Lys Cys Gly Glu Pro Asn Arg<br>785                      790                  795                  800 | 2400 |
| tgc gcg cca cac ctt gaa tgg aat cct gac tta gat tgt tcg tgt agg<br>Cys Ala Pro His Leu Glu Trp Asn Pro Asp Leu Asp Cys Ser Cys Arg<br>                805                  810                  815 | 2448 |
| gat gga gaa aag tgt gcc cat cat tcg cat cat ttc tcc tta gac att<br>Asp Gly Glu Lys Cys Ala His His Ser His His Phe Ser Leu Asp Ile<br>        820                  825                  830 | 2496 |
| gat gta gga tgt aca gac tta aat gag gac cta ggt gta tgg gtg atc<br>Asp Val Gly Cys Thr Asp Leu Asn Glu Asp Leu Gly Val Trp Val Ile<br>835                      840                  845 | 2544 |
| ttt aag att aag acg caa gat ggg cac gca aga cta ggg aat cta gag<br>Phe Lys Ile Lys Thr Gln Asp Gly His Ala Arg Leu Gly Asn Leu Glu<br>850                      855                  860 | 2592 |
| ttt ctc gaa gag aaa cca tta gta gga gaa gca cta gct cgt gtg aaa<br>Phe Leu Glu Glu Lys Pro Leu Val Gly Glu Ala Leu Ala Arg Val Lys<br>865                      870                  875                  880 | 2640 |
| aga gcg gag aaa aaa tgg aga gac aaa cgt gaa aaa ttg gaa tgg gaa<br>Arg Ala Glu Lys Lys Trp Arg Asp Lys Arg Glu Lys Leu Glu Trp Glu<br>                885                  890                  895 | 2688 |
| aca aat atc gtt tat aaa gag gca aaa gaa tct gta gat gct tta ttt<br>Thr Asn Ile Val Tyr Lys Glu Ala Lys Glu Ser Val Asp Ala Leu Phe<br>        900                  905                  910 | 2736 |
| gta aac tct caa tat gat caa tta caa gcg gat acg aat att gcc atg<br>Val Asn Ser Gln Tyr Asp Gln Leu Gln Ala Asp Thr Asn Ile Ala Met<br>915                      920                  925 | 2784 |
| att cat gcg gca gat aaa cgt gtt cat agc att cga gaa gct tat ctg<br>Ile His Ala Ala Asp Lys Arg Val His Ser Ile Arg Glu Ala Tyr Leu<br>930                      935                  940 | 2832 |
| cct gag ctg tct gtg att ccg ggt gtc aat gcg gct att ttt gaa gaa<br>Pro Glu Leu Ser Val Ile Pro Gly Val Asn Ala Ala Ile Phe Glu Glu<br>945                      950                  955                  960 | 2880 |
| tta gaa ggg cgt att ttc act gca ttc tcc cta tat gat gcg aga aat<br>Leu Glu Gly Arg Ile Phe Thr Ala Phe Ser Leu Tyr Asp Ala Arg Asn<br>                965                  970                  975 | 2928 |
| gtc att aaa aat ggt gat ttt aat aat ggc tta tcc tgc tgg aac gtg<br>Val Ile Lys Asn Gly Asp Phe Asn Asn Gly Leu Ser Cys Trp Asn Val<br>        980                  985                  990 | 2976 |
| aaa ggg cat gta gat gta gaa gaa  caa aac aac caa cgt  tcg gtc ctt<br>Lys Gly His Val Asp Val Glu Glu  Gln Asn Asn Gln Arg  Ser Val Leu<br>995                      1000                    1005 | 3024 |
| gtt gtt  ccg gaa tgg gaa gca  gaa gtg tca caa gaa  gtt cgt gtc<br>Val Val  Pro Glu Trp Glu Ala  Glu Val Ser Gln Glu  Val Arg Val<br>1010                    1015                  1020 | 3069 |
| tgt ccg  ggt cgt ggc tat atc  ctt cgt gtc aca gcg  tac aag gag<br>Cys Pro  Gly Arg Gly Tyr Ile  Leu Arg Val Thr Ala  Tyr Lys Glu<br>1025                    1030                  1035 | 3114 |
| gga tat  gga gaa ggt tgc gta  acc att cat gag atc  gag aac aat<br>Gly Tyr  Gly Glu Gly Cys Val  Thr Ile His Glu Ile  Glu Asn Asn<br>1040                    1045                  1050 | 3159 |
| aca gac  gaa ctg aag ttt agc  aac tgc gta gaa gag  gaa atc tat<br>Thr Asp  Glu Leu Lys Phe Ser  Asn Cys Val Glu Glu  Glu Ile Tyr<br>1055                    1060                  1065 | 3204 |
| cca aat  aac acg gta acg tgt  aat gat tat act gta  aat caa gaa<br>Pro Asn  Asn Thr Val Thr Cys  Asn Asp Tyr Thr Val  Asn Gln Glu<br>1070                    1075                  1080 | 3249 |
| gaa tac  gga ggt gcg tac act  tct cgt aat cga gga  tat aac gaa<br>Glu Tyr  Gly Gly Ala Tyr Thr  Ser Arg Asn Arg Gly  Tyr Asn Glu<br>1085                    1090                  1095 | 3294 |

```
gct cct tcc gta cca gct gat tat gcg tca gtc tat gaa gaa aaa       3339
Ala Pro Ser Val Pro Ala Asp Tyr Ala Ser Val Tyr Glu Glu Lys
    1100                1105                1110 tcg tat aca gat gga cga aga gag aat cct tgt gaa ttt aac aga       3384
Ser Tyr Thr Asp Gly Arg Arg Glu Asn Pro Cys Glu Phe Asn Arg
1115                1120                1125 ggg tat agg gat tac acg cca cta cca gtt ggt tat gtg aca aaa       3429
Gly Tyr Arg Asp Tyr Thr Pro Leu Pro Val Gly Tyr Val Thr Lys
    1130                1135                1140 gaa tta gaa tac ttc cca gaa acc gat aag gta tgg att gag att       3474
Glu Leu Glu Tyr Phe Pro Glu Thr Asp Lys Val Trp Ile Glu Ile
1145                1150                1155 gga gaa acg gaa gga aca ttt atc gtg gac agc gtg gaa tta ctc       3519
Gly Glu Thr Glu Gly Thr Phe Ile Val Asp Ser Val Glu Leu Leu
    1160                1165                1170 ctt atg gag gaa tag                                               3534
Leu Met Glu Glu
1175
```

<210> SEQ ID NO 6
<211> LENGTH: 1177
<212> TYPE: PRT
<213> ORGANISM: Artificial Sequence
<220> FEATURE:
<223> OTHER INFORMATION: Synthetic Construct

<400> SEQUENCE: 6

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240
```

```
Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Met Ala Gln Arg Ile Glu
                275                 280                 285

Gln Asn Ile Arg Gln Pro His Leu Met Asp Ile Leu Asn Ser Ile Thr
            290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Val Leu Val Ser Leu
                340                 345                 350

Thr Gly Leu Gly Ile Phe Arg Thr Leu Ser Ser Pro Leu Tyr Arg Arg
                355                 360                 365

Ile Ile Leu Gly Ser Gly Pro Asn Asn Gln Glu Leu Phe Val Leu Asp
            370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
                420                 425                 430

His Val Thr Met Leu Ser Gln Ala Ala Gly Ala Val Tyr Thr Leu Arg
                435                 440                 445

Ala Pro Thr Phe Ser Trp Gln His Arg Ser Ala Thr Thr Thr Asn Ile
450                 455                 460

Ile Ala Ala Asp Ser Ile Thr Gln Ile Pro Ala Val Lys Gly Arg Ser
465                 470                 475                 480

Ile Ile Asn Asn Gly Thr Val Ile Ser Gly Pro Gly Phe Thr Gly Gly
                485                 490                 495

Asp Leu Val Arg Leu Tyr Asn Ala Asp Phe Asn Ile Asn Asn Arg Ala
                500                 505                 510

Tyr Leu Glu Val Pro Ile Phe Phe Gln Ser Pro Ser Thr Asn Tyr Arg
            515                 520                 525

Val Arg Val Arg Tyr Ala Ser Thr Ser Ser Leu Pro Val Asp Val Val
530                 535                 540

Phe Gly Asn Ile Ser His Pro Thr Thr Phe Pro Ala Thr Ala Arg Ser
545                 550                 555                 560

Leu Asp Asn Leu Gln Ser Asn Asp Phe Gly Tyr Ile Asp Ile Ala Gly
                565                 570                 575

Thr Phe Leu Pro Ser Leu Gly Pro Ser Ile Gly Ile Arg Pro Met Leu
                580                 585                 590

Ser Thr Ile Asn Leu Ile Val Asp Arg Phe Glu Phe Ile Pro Val Thr
            595                 600                 605

Ala Thr Phe Glu Ala Glu Ser Asp Leu Glu Arg Ala Gln Lys Ala Val
610                 615                 620

Asn Ala Leu Phe Thr Ser Thr Asn Gln Leu Gly Ile Lys Thr Asp Val
625                 630                 635                 640

Thr Asp Tyr His Ile Asp Gln Val Ser Asn Leu Val Glu Cys Leu Ser
                645                 650                 655
```

-continued

```
Asp Glu Phe Tyr Leu Asp Glu Lys Arg Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Pro Asp Arg Gly Trp Arg Gly Ser Thr
    690                 695                 700

Asp Ile Thr Ile Gln Gly Gly Asp Val Phe Lys Glu Asn Tyr Val
705                 710                 715                 720

Thr Leu Pro Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
    850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Gln Leu Gln Ala Asp Thr Asn Ile Ala Met
        915                 920                 925

Ile His Ala Ala Asp Lys Arg Val His Ser Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn Gln Arg Ser Val Leu
        995                 1000                1005

Val Val Pro Glu Trp Glu Ala Glu Val Ser Gln Glu Val Arg Val
    1010                1015                1020

Cys Pro Gly Arg Gly Tyr Ile Leu Arg Val Thr Ala Tyr Lys Glu
    1025                1030                1035

Gly Tyr Gly Glu Gly Cys Val Thr Ile His Glu Ile Glu Asn Asn
    1040                1045                1050

Thr Asp Glu Leu Lys Phe Ser Asn Cys Val Glu Glu Glu Ile Tyr
    1055                1060                1065

Pro Asn Asn Thr Val Thr Cys Asn Asp Tyr Thr Val Asn Gln Glu
```

```
    1070                1075                1080

Glu Tyr  Gly Gly Ala Tyr Thr  Ser Arg Asn Arg Gly  Tyr Asn Glu
    1085                1090                1095

Ala Pro  Ser Val Pro Ala Asp  Tyr Ala Ser Val Tyr  Glu Glu Lys
    1100                1105                1110

Ser Tyr  Thr Asp Gly Arg Arg  Glu Asn Pro Cys Glu  Phe Asn Arg
    1115                1120                1125

Gly Tyr  Arg Asp Tyr Thr Pro  Leu Pro Val Gly Tyr  Val Thr Lys
    1130                1135                1140

Glu Leu  Glu Tyr Phe Pro Glu  Thr Asp Lys Val Trp  Ile Glu Ile
    1145                1150                1155

Gly Glu  Thr Glu Gly Thr Phe  Ile Val Asp Ser Val  Glu Leu Leu
    1160                1165                1170

Leu Met  Glu Glu
    1175

<210> SEQ ID NO 7
<211> LENGTH: 3543
<212> TYPE: DNA
<213> ORGANISM: Artificial Sequence
<220> FEATURE:
<223> OTHER INFORMATION: Fully Synthetic Sequence For Use In Plants
      Encoding BCW 001
<220> FEATURE:
<221> NAME/KEY: CDS
<222> LOCATION: (1)..(3540)
<223> OTHER INFORMATION: BCW 001

<400> SEQUENCE: 7 atg gag gag aac aac cag aac cag tgt gtc cca tac aac tgc ctc aac      48
Met Glu Glu Asn Asn Gln Asn Gln Cys Val Pro Tyr Asn Cys Leu Asn
1               5                   10                  15 aac cca gcc atc gaa atc ctt gag ggc gac cga att tca gtc ggc aac      96
Asn Pro Ala Ile Glu Ile Leu Glu Gly Asp Arg Ile Ser Val Gly Asn
            20                  25                  30 acg ccc atc gac atc tcc ctg agt ctt gtg gaa ctc ctc atc tcg gag     144
Thr Pro Ile Asp Ile Ser Leu Ser Leu Val Glu Leu Leu Ile Ser Glu
        35                  40                  45 ttc gtc cct ggc ggc ggc ata atc acc ggt ctg ctc aac atc gtg tgg     192
Phe Val Pro Gly Gly Gly Ile Ile Thr Gly Leu Leu Asn Ile Val Trp
    50                  55                  60 gga ttc gtg ggc cca tcc cag tgg gat gcg ttc ctg gcc caa gtg gag     240
Gly Phe Val Gly Pro Ser Gln Trp Asp Ala Phe Leu Ala Gln Val Glu
65                  70                  75                  80 cag ctc atc aac cag agg atc tcc gag gcc gtc cgc aat acc gcg atc     288
Gln Leu Ile Asn Gln Arg Ile Ser Glu Ala Val Arg Asn Thr Ala Ile
                85                  90                  95 caa gag ctg gag ggc atg gcc cgc gtg tac cgc acc tac gcc acc gcc     336
Gln Glu Leu Glu Gly Met Ala Arg Val Tyr Arg Thr Tyr Ala Thr Ala
            100                 105                 110 ttt gct gaa tgg gag cgc gac ccg aac aac act gac ctg cgc gag gcc     384
Phe Ala Glu Trp Glu Arg Asp Pro Asn Asn Thr Asp Leu Arg Glu Ala
        115                 120                 125 gtc cga aca cag ttc acg gcg acc gag acc tac atc agc ggc cgg atc     432
Val Arg Thr Gln Phe Thr Ala Thr Glu Thr Tyr Ile Ser Gly Arg Ile
    130                 135                 140 tca gtg ctc aag atc cag aac ttc gag gtg cag ctc cta tcg gtc ttc     480
Ser Val Leu Lys Ile Gln Asn Phe Glu Val Gln Leu Leu Ser Val Phe
145                 150                 155                 160 gcc cag gcc gcc aac ttg cac ctg agc ctc ctg cgg gac gtt gtg ttc     528
```

|   |   |   |   |   |   |   |   |   |   |   |   |   |   |   |   |   |
|---|---|---|---|---|---|---|---|---|---|---|---|---|---|---|---|---|
| Ala | Gln | Ala | Ala | Asn<br>165 | Leu | His | Leu | Ser | Leu<br>170 | Leu | Arg | Asp | Val | Val<br>175 | Phe |   |

| ttc | ggc | cag | cgg | tgg | ggc | ttc | tct | act | acg | acc | gtg | aac | aac | tac | tac | 576 |
|---|---|---|---|---|---|---|---|---|---|---|---|---|---|---|---|---|
| Phe | Gly | Gln | Arg | Trp<br>180 | Gly | Phe | Ser | Thr | Thr<br>185 | Thr | Val | Asn | Asn<br>190 | Tyr | Tyr |   |

| aac | gac | ctg | acg | gag | gaa | atc | agc | acc | tac | aca | gat | tac | gca | gtt | cgt | 624 |
|---|---|---|---|---|---|---|---|---|---|---|---|---|---|---|---|---|
| Asn | Asp | Leu | Thr<br>195 | Glu | Glu | Ile | Ser | Thr<br>200 | Tyr | Thr | Asp | Tyr<br>205 | Ala | Val | Arg |   |

| tgg | tac | aac | acc | ggc | ctt | gag | cgc | gtg | tgg | ggc | ccg | gac | tcc | cgc | gat | 672 |
|---|---|---|---|---|---|---|---|---|---|---|---|---|---|---|---|---|
| Trp | Tyr | Asn<br>210 | Thr | Gly | Leu | Glu | Arg<br>215 | Val | Trp | Gly | Pro | Asp<br>220 | Ser | Arg | Asp |   |

| tgg | gtc | cgc | tac | aac | cag | ttc | cgc | cgc | gag | ctg | acg | ctt | aca | gtg | ctg | 720 |
|---|---|---|---|---|---|---|---|---|---|---|---|---|---|---|---|---|
| Trp<br>225 | Val | Arg | Tyr | Asn | Gln<br>230 | Phe | Arg | Arg | Glu | Leu<br>235 | Thr | Leu | Thr | Val | Leu<br>240 |   |

| gac | atc | gtc | gca | ctc | ttt | cct | aac | tac | gac | tcc | agg | cgc | tat | ccc | atc | 768 |
|---|---|---|---|---|---|---|---|---|---|---|---|---|---|---|---|---|
| Asp | Ile | Val | Ala | Leu<br>245 | Phe | Pro | Asn | Tyr | Asp<br>250 | Ser | Arg | Arg | Tyr | Pro<br>255 | Ile |   |

| agg | aca | gtg | tca | cag | ctc | acc | cgc | gag | atc | tac | aca | aac | ccg | gtg | ctt | 816 |
|---|---|---|---|---|---|---|---|---|---|---|---|---|---|---|---|---|
| Arg | Thr | Val | Ser<br>260 | Gln | Leu | Thr | Arg | Glu<br>265 | Ile | Tyr | Thr | Asn | Pro<br>270 | Val | Leu |   |

| gag | aac | ttc | gac | ggc | agc | ttc | cgt | ggc | atg | gcg | cag | cgc | att | gaa | cag | 864 |
|---|---|---|---|---|---|---|---|---|---|---|---|---|---|---|---|---|
| Glu | Asn | Phe | Asp<br>275 | Gly | Ser | Phe | Arg | Gly<br>280 | Met | Ala | Gln | Arg | Ile<br>285 | Glu | Gln |   |

| aac | atc | cgc | cag | ccg | cac | ctt | atg | gac | atc | ttg | aac | agt | atc | act | atc | 912 |
|---|---|---|---|---|---|---|---|---|---|---|---|---|---|---|---|---|
| Asn | Ile | Arg | Gln<br>290 | Pro | His | Leu | Met | Asp<br>295 | Ile | Leu | Asn | Ser | Ile<br>300 | Thr | Ile |   |

| tac | acc | gac | gtc | cac | aga | ggc | ttc | aac | tac | tgg | agc | gga | cac | cag | atc | 960 |
|---|---|---|---|---|---|---|---|---|---|---|---|---|---|---|---|---|
| Tyr<br>305 | Thr | Asp | Val | His | Arg<br>310 | Gly | Phe | Asn | Tyr | Trp<br>315 | Ser | Gly | His | Gln | Ile<br>320 |   |

| aca | gcc | agc | ccg | gta | ggc | ttc | tcg | ggt | cca | gag | ttc | gcc | ttc | ccg | ctg | 1008 |
|---|---|---|---|---|---|---|---|---|---|---|---|---|---|---|---|---|
| Thr | Ala | Ser | Pro | Val<br>325 | Gly | Phe | Ser | Gly | Pro<br>330 | Glu | Phe | Ala | Phe | Pro<br>335 | Leu |   |

| ttt | ggg | aac | gct | ggc | aat | gcc | gcg | ccg | ccc | gtg | ctg | gtc | agc | ctc | act | 1056 |
|---|---|---|---|---|---|---|---|---|---|---|---|---|---|---|---|---|
| Phe | Gly | Asn | Ala<br>340 | Gly | Asn | Ala | Ala | Pro<br>345 | Pro | Val | Leu | Val | Ser<br>350 | Leu | Thr |   |

| ggt | ctc | ggc | atc | ttc | cgc | aca | ctt | tcc | tcg | ccg | ctg | tac | agg | agg | atc | 1104 |
|---|---|---|---|---|---|---|---|---|---|---|---|---|---|---|---|---|
| Gly | Leu | Gly | Ile<br>355 | Phe | Arg | Thr | Leu | Ser<br>360 | Ser | Pro | Leu | Tyr | Arg<br>365 | Arg | Ile |   |

| atc | ctc | ggg | tcc | ggt | ccg | aac | aac | cag | gag | ctg | ttc | gtg | ctc | gac | ggg | 1152 |
|---|---|---|---|---|---|---|---|---|---|---|---|---|---|---|---|---|
| Ile | Leu | Gly<br>370 | Ser | Gly | Pro | Asn | Asn<br>375 | Gln | Glu | Leu | Phe | Val<br>380 | Leu | Asp | Gly |   |

| acc | gag | ttc | agt | ttc | gcc | agc | ctc | acg | acg | aac | ctc | ccg | tcc | acc | atc | 1200 |
|---|---|---|---|---|---|---|---|---|---|---|---|---|---|---|---|---|
| Thr<br>385 | Glu | Phe | Ser | Phe | Ala<br>390 | Ser | Leu | Thr | Thr | Asn<br>395 | Leu | Pro | Ser | Thr | Ile<br>400 |   |

| tat | cgc | cag | cgc | gga | acg | gtc | gat | tcc | ctg | gat | gtt | atc | cca | ccg | caa | 1248 |
|---|---|---|---|---|---|---|---|---|---|---|---|---|---|---|---|---|
| Tyr | Arg | Gln | Arg | Gly<br>405 | Thr | Val | Asp | Ser | Leu<br>410 | Asp | Val | Ile | Pro | Pro<br>415 | Gln |   |

| gac | aat | tct | gtg | ccg | ccg | agg | gcc | ggg | ttc | tcc | cac | cgg | ctg | tct | cac | 1296 |
|---|---|---|---|---|---|---|---|---|---|---|---|---|---|---|---|---|
| Asp | Asn | Ser | Val<br>420 | Pro | Pro | Arg | Ala | Gly<br>425 | Phe | Ser | His | Arg | Leu<br>430 | Ser | His |   |

| gtg | act | atg | ctt | tca | cag | gcc | gcc | gga | gcc | gtg | tac | acg | ctc | cgt | gcg | 1344 |
|---|---|---|---|---|---|---|---|---|---|---|---|---|---|---|---|---|
| Val | Thr | Met<br>435 | Leu | Ser | Gln | Ala | Ala<br>440 | Gly | Ala | Val | Tyr | Thr<br>445 | Leu | Arg | Ala |   |

| cct | act | ttc | tcc | tgg | cag | cac | cgc | agc | gcg | acc | acg | acc | aac | atc | atc | 1392 |
|---|---|---|---|---|---|---|---|---|---|---|---|---|---|---|---|---|
| Pro | Thr | Phe | Ser<br>450 | Trp | Gln | His | Arg | Ser<br>455 | Ala | Thr | Thr | Thr | Asn<br>460 | Ile | Ile |   |

| gca | gca | gac | tcc | atc | acc | cag | atc | ccg | gcc | gtt | aag | ggc | cgc | agc | atc | 1440 |
|---|---|---|---|---|---|---|---|---|---|---|---|---|---|---|---|---|
| Ala<br>465 | Ala | Asp | Ser | Ile | Thr<br>470 | Gln | Ile | Pro | Ala | Val<br>475 | Lys | Gly | Arg | Ser | Ile<br>480 |   |

```
atc aac aac gga act gtc atc agc ggt ccg ggc ttc acg ggc ggc gac       1488
Ile Asn Asn Gly Thr Val Ile Ser Gly Pro Gly Phe Thr Gly Gly Asp
                485                 490                 495 ctg gtc cgg ctc tac aac gca gac ttc aac atc aat aac cgc gct tat       1536
Leu Val Arg Leu Tyr Asn Ala Asp Phe Asn Ile Asn Asn Arg Ala Tyr
            500                 505                 510 ctt gaa gta cct atc ttc ttc cag agc ccg agc act aac tac cgg gtt       1584
Leu Glu Val Pro Ile Phe Phe Gln Ser Pro Ser Thr Asn Tyr Arg Val
        515                 520                 525 cgc gtc cgc tac gcc agc acc tcc agc ctc cct gtg gat gtc gtg ttc       1632
Arg Val Arg Tyr Ala Ser Thr Ser Ser Leu Pro Val Asp Val Val Phe
    530                 535                 540 gga aac ata agc cat ccg acc acg ttc cca gcc acg gct agg agc ctg       1680
Gly Asn Ile Ser His Pro Thr Thr Phe Pro Ala Thr Ala Arg Ser Leu
545                 550                 555                 560 gac aac cta cag agc aac gac ttc ggc tac atc gac atc gcg ggc acc       1728
Asp Asn Leu Gln Ser Asn Asp Phe Gly Tyr Ile Asp Ile Ala Gly Thr
                565                 570                 575 ttt ctg cca agc ctg ggt ccg tct atc ggc atc cgc ccg atg ctg agc       1776
Phe Leu Pro Ser Leu Gly Pro Ser Ile Gly Ile Arg Pro Met Leu Ser
            580                 585                 590 act atc aac cta att gtg gac cgg ttc gag ttt atc ccg gtg acg gca       1824
Thr Ile Asn Leu Ile Val Asp Arg Phe Glu Phe Ile Pro Val Thr Ala
        595                 600                 605 acg ttc gag gcg gag tct gac ctc gaa agg gca cag aag gcc gtg aac       1872
Thr Phe Glu Ala Glu Ser Asp Leu Glu Arg Ala Gln Lys Ala Val Asn
    610                 615                 620 gcc ctg ttc acg agc acc aac cag ctt ggc att aag act gat gtc acc       1920
Ala Leu Phe Thr Ser Thr Asn Gln Leu Gly Ile Lys Thr Asp Val Thr
625                 630                 635                 640 gac tac cac att gac caa gtc agc aac ctg gtg gag tgc ctc tcg gac       1968
Asp Tyr His Ile Asp Gln Val Ser Asn Leu Val Glu Cys Leu Ser Asp
                645                 650                 655 gag ttc tat ctt gat gag aaa cgg gaa cta agc gag aag gtg aag cac       2016
Glu Phe Tyr Leu Asp Glu Lys Arg Glu Leu Ser Glu Lys Val Lys His
            660                 665                 670 gca aag cgc ttg agc gac gag cgg aac tta ctc cag gac cct aac ttc       2064
Ala Lys Arg Leu Ser Asp Glu Arg Asn Leu Leu Gln Asp Pro Asn Phe
        675                 680                 685 cgt ggg att aac cgc cag ccg gat cgc ggg tgg cgc ggc tca acg gac       2112
Arg Gly Ile Asn Arg Gln Pro Asp Arg Gly Trp Arg Gly Ser Thr Asp
    690                 695                 700 atc acc atc cag ggc ggc gat gac gtc ttc aag gag aac tac gtg acc       2160
Ile Thr Ile Gln Gly Gly Asp Asp Val Phe Lys Glu Asn Tyr Val Thr
705                 710                 715                 720 ctc cct ggc acg ttc gac gag tgc tac ccg acg tac ctt tat cag aag       2208
Leu Pro Gly Thr Phe Asp Glu Cys Tyr Pro Thr Tyr Leu Tyr Gln Lys
                725                 730                 735 att gac gaa agc aag ctg aaa gcc tac acc cgc tac cag ttg cgc ggc       2256
Ile Asp Glu Ser Lys Leu Lys Ala Tyr Thr Arg Tyr Gln Leu Arg Gly
            740                 745                 750 tac atc gag gac tct caa gac ctg gag atc tac ttg att cga tac aac       2304
Tyr Ile Glu Asp Ser Gln Asp Leu Glu Ile Tyr Leu Ile Arg Tyr Asn
        755                 760                 765 gcg aaa cac gag acc gtc aac gtg ccg ggc act ggg agc ctg tgg ccg       2352
Ala Lys His Glu Thr Val Asn Val Pro Gly Thr Gly Ser Leu Trp Pro
    770                 775                 780 ttg tct gca caa agt ccg atc ggc aag tgc ggc gag cca aac cgg tgc       2400
Leu Ser Ala Gln Ser Pro Ile Gly Lys Cys Gly Glu Pro Asn Arg Cys
785                 790                 795                 800
```

| | | |
|---|---|---|
| gct ccg cac ctg gag tgg aac cca gac ctt cat tgc tcc tgt agg gat<br>Ala Pro His Leu Glu Trp Asn Pro Asp Leu His Cys Ser Cys Arg Asp<br>805 810 815 | | 2448 |
| ggc gag aag tgc gct cac cac agc cat cac ttc agc ctc gac att gac<br>Gly Glu Lys Cys Ala His His Ser His His Phe Ser Leu Asp Ile Asp<br>820 825 830 | | 2496 |
| gtc ggc tgt acc gac ctt aat gag gat ctg ggt gtg tgg gtg atc ttc<br>Val Gly Cys Thr Asp Leu Asn Glu Asp Leu Gly Val Trp Val Ile Phe<br>835 840 845 | | 2544 |
| aag atc aag acc cag gac ggt cac gcc cgg ttg ggc aat ctg gag ttc<br>Lys Ile Lys Thr Gln Asp Gly His Ala Arg Leu Gly Asn Leu Glu Phe<br>850 855 860 | | 2592 |
| ctg gag gag aag ccg ctg gtt ggc gag gct ctc gcg cgg gtc aag cgg<br>Leu Glu Glu Lys Pro Leu Val Gly Glu Ala Leu Ala Arg Val Lys Arg<br>865 870 875 880 | | 2640 |
| gcg gag aag aag tgg cgg gac aaa cgc gag aag ctc cag tta gag acg<br>Ala Glu Lys Lys Trp Arg Asp Lys Arg Glu Lys Leu Gln Leu Glu Thr<br>885 890 895 | | 2688 |
| aac atc gtg tac aag gag gcg aag gaa tcc gtg gac gca cta ttc gtg<br>Asn Ile Val Tyr Lys Glu Ala Lys Glu Ser Val Asp Ala Leu Phe Val<br>900 905 910 | | 2736 |
| aac agc cag tac gac caa ctc cag gcc gac acc aac atc gcc atg att<br>Asn Ser Gln Tyr Asp Gln Leu Gln Ala Asp Thr Asn Ile Ala Met Ile<br>915 920 925 | | 2784 |
| cac gca gcc gac aag agg gtg cac cgc atc cgc gaa gcc tac ctt ccc<br>His Ala Ala Asp Lys Arg Val His Arg Ile Arg Glu Ala Tyr Leu Pro<br>930 935 940 | | 2832 |
| gaa ctt tcg gtc atc cca ggc gtc aac gct gac atc tcg gag gaa ttg<br>Glu Leu Ser Val Ile Pro Gly Val Asn Ala Asp Ile Ser Glu Glu Leu<br>945 950 955 960 | | 2880 |
| gag ggc aga atc ttc acg gcc ttc tct ttg tac gat gcc agg aac gtc<br>Glu Gly Arg Ile Phe Thr Ala Phe Ser Leu Tyr Asp Ala Arg Asn Val<br>965 970 975 | | 2928 |
| atc aag aac ggc gac ttc aac aac ggc ctg ctg tgc tgg aac gtg aag<br>Ile Lys Asn Gly Asp Phe Asn Asn Gly Leu Leu Cys Trp Asn Val Lys<br>980 985 990 | | 2976 |
| ggc cac gtg gac gtc gag gag cag aac aac cac aga tca gtc ctg gtg<br>Gly His Val Asp Val Glu Glu Gln Asn Asn His Arg Ser Val Leu Val<br>995 1000 1005 | | 3024 |
| gtg ccc gag tgg gaa gcc gaa gtc tca caa gaa gtc cgg gtg tgc<br>Val Pro Glu Trp Glu Ala Glu Val Ser Gln Glu Val Arg Val Cys<br>1010 1015 1020 | | 3069 |
| cct gga cgc ggg tac att ctc cgc gtg acc gcc tac aag gag ggc<br>Pro Gly Arg Gly Tyr Ile Leu Arg Val Thr Ala Tyr Lys Glu Gly<br>1025 1030 1035 | | 3114 |
| tac ggt gag ggc tgc gtg acc atc cac gag atc gag aac aac acc<br>Tyr Gly Glu Gly Cys Val Thr Ile His Glu Ile Glu Asn Asn Thr<br>1040 1045 1050 | | 3159 |
| gac gag ctg aaa ttc agt aac tgt gtt gag gag gag gtg tac ccg<br>Asp Glu Leu Lys Phe Ser Asn Cys Val Glu Glu Glu Val Tyr Pro<br>1055 1060 1065 | | 3204 |
| aac aac acc gtc acc tgc aac gac tac act gcg aac cag gag gaa<br>Asn Asn Thr Val Thr Cys Asn Asp Tyr Thr Ala Asn Gln Glu Glu<br>1070 1075 1080 | | 3249 |
| tac gag ggc acg tac acg agc cgc aat cgc ggg tac gac gag gcg<br>Tyr Glu Gly Thr Tyr Thr Ser Arg Asn Arg Gly Tyr Asp Glu Ala<br>1085 1090 1095 | | 3294 |
| tac gag agc aac tcc agc gtc ccg gcc gag tac gcc tcc gtg tac<br>Tyr Glu Ser Asn Ser Ser Val Pro Ala Glu Tyr Ala Ser Val Tyr | | 3339 |

```
                    1100              1105              1110
gag gag aag gtt tac acc gac ggg agg cgt ggc aac ccg tgc gag    3384
Glu Glu Lys Val Tyr Thr Asp Gly Arg Arg Gly Asn Pro Cys Glu
        1115              1120              1125 agc aac aga ggc tac ggc gat tac act ccg ctt ccc gct ggc tac    3429
Ser Asn Arg Gly Tyr Gly Asp Tyr Thr Pro Leu Pro Ala Gly Tyr
    1130              1135              1140 gtg acg aaa gag ctg gag tac ttc cca gag acc gac aag gtg tgg    3474
Val Thr Lys Glu Leu Glu Tyr Phe Pro Glu Thr Asp Lys Val Trp
        1145              1150              1155 atc gag atc gga gaa acg gag ggc acg ttc ata gtg gac tcc gtt    3519
Ile Glu Ile Gly Glu Thr Glu Gly Thr Phe Ile Val Asp Ser Val
    1160              1165              1170 gag ctg ctg ctc atg gag gag tag                                3543
Glu Leu Leu Leu Met Glu Glu
        1175              1180

<210> SEQ ID NO 8
<211> LENGTH: 1180
<212> TYPE: PRT
<213> ORGANISM: Artificial Sequence
<220> FEATURE:
<223> OTHER INFORMATION: Synthetic Construct

<400> SEQUENCE: 8

Met Glu Glu Asn Asn Gln Asn Gln Cys Val Pro Tyr Asn Cys Leu Asn
1               5                   10                  15

Asn Pro Ala Ile Glu Ile Leu Glu Gly Asp Arg Ile Ser Val Gly Asn
            20                  25                  30

Thr Pro Ile Asp Ile Ser Leu Ser Leu Val Glu Leu Leu Ile Ser Glu
        35                  40                  45

Phe Val Pro Gly Gly Gly Ile Ile Thr Gly Leu Leu Asn Ile Val Trp
    50                  55                  60

Gly Phe Val Gly Pro Ser Gln Trp Asp Ala Phe Leu Ala Gln Val Glu
65                  70                  75                  80

Gln Leu Ile Asn Gln Arg Ile Ser Glu Ala Val Arg Asn Thr Ala Ile
                85                  90                  95

Gln Glu Leu Glu Gly Met Ala Arg Val Tyr Arg Thr Tyr Ala Thr Ala
            100                 105                 110

Phe Ala Glu Trp Glu Arg Asp Pro Asn Asn Thr Asp Leu Arg Glu Ala
        115                 120                 125

Val Arg Thr Gln Phe Thr Ala Thr Glu Thr Tyr Ile Ser Gly Arg Ile
    130                 135                 140

Ser Val Leu Lys Ile Gln Asn Phe Glu Val Gln Leu Leu Ser Val Phe
145                 150                 155                 160

Ala Gln Ala Ala Asn Leu His Leu Ser Leu Leu Arg Asp Val Val Phe
                165                 170                 175

Phe Gly Gln Arg Trp Gly Phe Ser Thr Thr Thr Val Asn Asn Tyr Tyr
            180                 185                 190

Asn Asp Leu Thr Glu Glu Ile Ser Thr Tyr Thr Asp Tyr Ala Val Arg
        195                 200                 205

Trp Tyr Asn Thr Gly Leu Glu Arg Val Trp Gly Pro Asp Ser Arg Asp
    210                 215                 220

Trp Val Arg Tyr Asn Gln Phe Arg Arg Glu Leu Thr Leu Thr Val Leu
225                 230                 235                 240

Asp Ile Val Ala Leu Phe Pro Asn Tyr Asp Ser Arg Arg Tyr Pro Ile
                245                 250                 255
```

-continued

```
Arg Thr Val Ser Gln Leu Thr Arg Glu Ile Tyr Thr Asn Pro Val Leu
            260                 265                 270

Glu Asn Phe Asp Gly Ser Phe Arg Gly Met Ala Gln Arg Ile Glu Gln
            275                 280                 285

Asn Ile Arg Gln Pro His Leu Met Asp Ile Leu Asn Ser Ile Thr Ile
            290                 295                 300

Tyr Thr Asp Val His Arg Gly Phe Asn Tyr Trp Ser Gly His Gln Ile
305                 310                 315                 320

Thr Ala Ser Pro Val Gly Phe Ser Gly Pro Glu Phe Ala Phe Pro Leu
                325                 330                 335

Phe Gly Asn Ala Gly Asn Ala Ala Pro Val Leu Val Ser Leu Thr
            340                 345                 350

Gly Leu Gly Ile Phe Arg Thr Leu Ser Ser Pro Leu Tyr Arg Arg Ile
            355                 360                 365

Ile Leu Gly Ser Gly Pro Asn Asn Gln Glu Leu Phe Val Leu Asp Gly
            370                 375                 380

Thr Glu Phe Ser Phe Ala Ser Leu Thr Thr Asn Leu Pro Ser Thr Ile
385                 390                 395                 400

Tyr Arg Gln Arg Gly Thr Val Asp Ser Leu Asp Val Ile Pro Pro Gln
                405                 410                 415

Asp Asn Ser Val Pro Pro Arg Ala Gly Phe Ser His Arg Leu Ser His
            420                 425                 430

Val Thr Met Leu Ser Gln Ala Ala Gly Ala Val Tyr Thr Leu Arg Ala
            435                 440                 445

Pro Thr Phe Ser Trp Gln His Arg Ser Ala Thr Thr Thr Asn Ile Ile
            450                 455                 460

Ala Ala Asp Ser Ile Thr Gln Ile Pro Ala Val Lys Gly Arg Ser Ile
465                 470                 475                 480

Ile Asn Asn Gly Thr Val Ile Ser Gly Pro Gly Phe Thr Gly Gly Asp
                485                 490                 495

Leu Val Arg Leu Tyr Asn Ala Asp Phe Asn Ile Asn Asn Arg Ala Tyr
            500                 505                 510

Leu Glu Val Pro Ile Phe Phe Gln Ser Pro Ser Thr Asn Tyr Arg Val
            515                 520                 525

Arg Val Arg Tyr Ala Ser Thr Ser Ser Leu Pro Val Asp Val Val Phe
            530                 535                 540

Gly Asn Ile Ser His Pro Thr Thr Phe Pro Ala Thr Ala Arg Ser Leu
545                 550                 555                 560

Asp Asn Leu Gln Ser Asn Asp Phe Gly Tyr Ile Asp Ile Ala Gly Thr
                565                 570                 575

Phe Leu Pro Ser Leu Gly Pro Ser Ile Gly Ile Arg Pro Met Leu Ser
            580                 585                 590

Thr Ile Asn Leu Ile Val Asp Arg Phe Glu Phe Ile Pro Val Thr Ala
            595                 600                 605

Thr Phe Glu Ala Glu Ser Asp Leu Glu Arg Ala Gln Lys Ala Val Asn
            610                 615                 620

Ala Leu Phe Thr Ser Thr Asn Gln Leu Gly Ile Lys Thr Asp Val Thr
625                 630                 635                 640

Asp Tyr His Ile Asp Gln Val Ser Asn Leu Val Glu Cys Leu Ser Asp
                645                 650                 655

Glu Phe Tyr Leu Asp Glu Lys Arg Glu Leu Ser Glu Lys Val Lys His
            660                 665                 670
```

```
Ala Lys Arg Leu Ser Asp Glu Arg Asn Leu Leu Gln Asp Pro Asn Phe
        675                 680                 685

Arg Gly Ile Asn Arg Gln Pro Asp Arg Gly Trp Arg Gly Ser Thr Asp
        690                 695                 700

Ile Thr Ile Gln Gly Gly Asp Val Phe Lys Glu Asn Tyr Val Thr
705                 710                 715                 720

Leu Pro Gly Thr Phe Asp Glu Cys Tyr Pro Thr Tyr Leu Tyr Gln Lys
                725                 730                 735

Ile Asp Glu Ser Lys Leu Lys Ala Tyr Thr Arg Tyr Gln Leu Arg Gly
                740                 745                 750

Tyr Ile Glu Asp Ser Gln Asp Leu Glu Ile Tyr Leu Ile Arg Tyr Asn
                755                 760                 765

Ala Lys His Glu Thr Val Asn Val Pro Gly Thr Gly Ser Leu Trp Pro
        770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu His Cys Ser Cys Arg Asp
                805                 810                 815

Gly Glu Lys Cys Ala His His Ser His His Phe Ser Leu Asp Ile Asp
                820                 825                 830

Val Gly Cys Thr Asp Leu Asn Glu Asp Leu Gly Val Trp Val Ile Phe
        835                 840                 845

Lys Ile Lys Thr Gln Asp Gly His Ala Arg Leu Gly Asn Leu Glu Phe
        850                 855                 860

Leu Glu Glu Lys Pro Leu Val Gly Glu Ala Leu Ala Arg Val Lys Arg
865                 870                 875                 880

Ala Glu Lys Lys Trp Arg Asp Lys Arg Glu Lys Leu Gln Leu Glu Thr
                885                 890                 895

Asn Ile Val Tyr Lys Glu Ala Lys Glu Ser Val Asp Ala Leu Phe Val
                900                 905                 910

Asn Ser Gln Tyr Asp Gln Leu Gln Ala Asp Thr Asn Ile Ala Met Ile
                915                 920                 925

His Ala Ala Asp Lys Arg Val His Arg Ile Arg Glu Ala Tyr Leu Pro
        930                 935                 940

Glu Leu Ser Val Ile Pro Gly Val Asn Ala Asp Ile Ser Glu Glu Leu
945                 950                 955                 960

Glu Gly Arg Ile Phe Thr Ala Phe Ser Leu Tyr Asp Ala Arg Asn Val
                965                 970                 975

Ile Lys Asn Gly Asp Phe Asn Asn Gly Leu Leu Cys Trp Asn Val Lys
                980                 985                 990

Gly His Val Asp Val Glu Glu Gln Asn Asn His Arg Ser Val Leu Val
                995                 1000                1005

Val Pro Glu Trp Glu Ala Glu Val Ser Gln Glu Val Arg Val Cys
        1010                1015                1020

Pro Gly Arg Gly Tyr Ile Leu Arg Val Thr Ala Tyr Lys Glu Gly
        1025                1030                1035

Tyr Gly Glu Gly Cys Val Thr Ile His Glu Ile Glu Asn Asn Thr
        1040                1045                1050

Asp Glu Leu Lys Phe Ser Asn Cys Val Glu Glu Val Tyr Pro
        1055                1060                1065

Asn Asn Thr Val Thr Cys Asn Asp Tyr Thr Ala Asn Gln Glu Glu
        1070                1075                1080

Tyr Glu Gly Thr Tyr Thr Ser Arg Asn Arg Gly Tyr Asp Glu Ala
```

-continued

```
          1085                1090                1095
Tyr Glu Ser Asn Ser Ser Val Pro Ala Glu Tyr Ala Ser Val Tyr
        1100                1105                1110

Glu Glu Lys Val Tyr Thr Asp Gly Arg Arg Gly Asn Pro Cys Glu
        1115                1120                1125

Ser Asn Arg Gly Tyr Gly Asp Tyr Thr Pro Leu Pro Ala Gly Tyr
        1130                1135                1140

Val Thr Lys Glu Leu Glu Tyr Phe Pro Glu Thr Asp Lys Val Trp
        1145                1150                1155

Ile Glu Ile Gly Glu Thr Glu Gly Thr Phe Ile Val Asp Ser Val
        1160                1165                1170

Glu Leu Leu Leu Met Glu Glu
        1175                1180

<210> SEQ ID NO 9
<211> LENGTH: 3534
<212> TYPE: DNA
<213> ORGANISM: Artificial Sequence
<220> FEATURE:
<223> OTHER INFORMATION: Fully Synthetic Sequence Encoding CW 002 For
      Use In Plants
<220> FEATURE:
<221> NAME/KEY: CDS
<222> LOCATION: (1)..(3531)
<223> OTHER INFORMATION: BCW 002

<400> SEQUENCE: 9 atg gac aac aac ccg aac atc aac gag tgc atc ccc tac aac tgc ctc      48
Met Asp Asn Asn Pro Asn Ile Asn Glu Cys Ile Pro Tyr Asn Cys Leu
1               5                   10                  15 tcc aac ccg gag gtc gag gtg ctg ggc ggc gaa agg atc gag acc ggc      96
Ser Asn Pro Glu Val Glu Val Leu Gly Gly Glu Arg Ile Glu Thr Gly
            20                  25                  30 tac act ccc atc gac atc agc ctc agc ctg acc cag ttc ctg ctc tct     144
Tyr Thr Pro Ile Asp Ile Ser Leu Ser Leu Thr Gln Phe Leu Leu Ser
        35                  40                  45 gag ttc gtg ccc ggc gcg ggg ttc gtt ctc ggc ctg gtc gac atc atc     192
Glu Phe Val Pro Gly Ala Gly Phe Val Leu Gly Leu Val Asp Ile Ile
    50                  55                  60 tgg ggc atc ttc ggt ccg agc cag tgg gac gcc ttt ctc gtt cag att     240
Trp Gly Ile Phe Gly Pro Ser Gln Trp Asp Ala Phe Leu Val Gln Ile
65                  70                  75                  80 gag cag ctg atc aac cag cgc atc gag gag ttc gcc cgc aac cag gcg     288
Glu Gln Leu Ile Asn Gln Arg Ile Glu Glu Phe Ala Arg Asn Gln Ala
                85                  90                  95 atc tcc cgg ctg gag ggc ctc tcc aac ctg tac caa atc tac gcc gag     336
Ile Ser Arg Leu Glu Gly Leu Ser Asn Leu Tyr Gln Ile Tyr Ala Glu
            100                 105                 110 agc ttc cgg gag tgg gaa gcc gat ccg acc aac ccc gct ctc agg gag     384
Ser Phe Arg Glu Trp Glu Ala Asp Pro Thr Asn Pro Ala Leu Arg Glu
        115                 120                 125 gag atg cgg att cag ttc aac gac atg aac tcc gct ctc acg act gcc     432
Glu Met Arg Ile Gln Phe Asn Asp Met Asn Ser Ala Leu Thr Thr Ala
    130                 135                 140 atc cca ctc ctc gct gtg cag aac tac caa gtg ccg ctc ctg tcc gtg     480
Ile Pro Leu Leu Ala Val Gln Asn Tyr Gln Val Pro Leu Leu Ser Val
145                 150                 155                 160 tac gtg cag gcc gcc aat ctg cac ctc tcc gtc ctc cgg gac gtt agc     528
Tyr Val Gln Ala Ala Asn Leu His Leu Ser Val Leu Arg Asp Val Ser
                165                 170                 175
```

```
                                      -continued gtg ttc ggg cag cgc tgg ggc ttc gac gcc gct acc atc aac tcc cgt    576
Val Phe Gly Gln Arg Trp Gly Phe Asp Ala Ala Thr Ile Asn Ser Arg
            180                 185                 190 tac aac gat ctc act cgc ctc atc ggc aac tac acc gac tat gcc gtg    624
Tyr Asn Asp Leu Thr Arg Leu Ile Gly Asn Tyr Thr Asp Tyr Ala Val
        195                 200                 205 cgc tgg tac aac act ggt ctt gag aga gtc tgg ggc ccg gac agc cgc    672
Arg Trp Tyr Asn Thr Gly Leu Glu Arg Val Trp Gly Pro Asp Ser Arg
    210                 215                 220 gac tgg gtg cgc tac aac cag ttc cgg cgc gag ctg acc ctc acc gtg    720
Asp Trp Val Arg Tyr Asn Gln Phe Arg Arg Glu Leu Thr Leu Thr Val
225                 230                 235                 240 ctc gac atc gta gcc ctc ttt ccc aac tac gac tcc cgg cgc tac ccg    768
Leu Asp Ile Val Ala Leu Phe Pro Asn Tyr Asp Ser Arg Arg Tyr Pro
                245                 250                 255 att cgc atc gtc agc cag ctc acc agg gag atc tac acc aac cct gtg    816
Ile Arg Ile Val Ser Gln Leu Thr Arg Glu Ile Tyr Thr Asn Pro Val
            260                 265                 270 ctg gag aac ttc gac ggc tcc ttt cgc ggg atg gcc caa cgc ata gag    864
Leu Glu Asn Phe Asp Gly Ser Phe Arg Gly Met Ala Gln Arg Ile Glu
        275                 280                 285 cag aac atc cgc caa cct cat ctg atg gac atc ctt aat tct atc acc    912
Gln Asn Ile Arg Gln Pro His Leu Met Asp Ile Leu Asn Ser Ile Thr
    290                 295                 300 atc tac act gac gtt cat cgc ggg ttt aac tac tgg tcg ggc cac caa    960
Ile Tyr Thr Asp Val His Arg Gly Phe Asn Tyr Trp Ser Gly His Gln
305                 310                 315                 320 atc act gcg tcg ccc gtt ggt ttc tcc ggc ccg gag ttc gcg ttc cct   1008
Ile Thr Ala Ser Pro Val Gly Phe Ser Gly Pro Glu Phe Ala Phe Pro
                325                 330                 335 ctg ttc gga aac gcg ggc aat gcc gct cca ccc gta ttg gtg agc ctg   1056
Leu Phe Gly Asn Ala Gly Asn Ala Ala Pro Pro Val Leu Val Ser Leu
            340                 345                 350 acc ggc ctc ggc atc ttc cgt aca ctg tct agc cct ctg tac aga agg   1104
Thr Gly Leu Gly Ile Phe Arg Thr Leu Ser Ser Pro Leu Tyr Arg Arg
        355                 360                 365 atc att ctt ggc agc ggt ccc aat aac cag gaa ctc ttc gtg ttg gac   1152
Ile Ile Leu Gly Ser Gly Pro Asn Asn Gln Glu Leu Phe Val Leu Asp
    370                 375                 380 ggc acc gag ttc agc ttc gcc agt ctt acg acc aat ttg ccc tcc aca   1200
Gly Thr Glu Phe Ser Phe Ala Ser Leu Thr Thr Asn Leu Pro Ser Thr
385                 390                 395                 400 atc tat cgc cag cgc ggt act gtg gac tcc ctt gat gtg ata cca cct   1248
Ile Tyr Arg Gln Arg Gly Thr Val Asp Ser Leu Asp Val Ile Pro Pro
                405                 410                 415 cag gac aac tct gtc cca cct cgc gcc ggt ttc tcc cac cgc ctc agc   1296
Gln Asp Asn Ser Val Pro Pro Arg Ala Gly Phe Ser His Arg Leu Ser
            420                 425                 430 cac gtc act atg ctg agt cag gct gcg gga gcc gtg tac acc ctt cgg   1344
His Val Thr Met Leu Ser Gln Ala Ala Gly Ala Val Tyr Thr Leu Arg
        435                 440                 445 gct ccg acg ttt agc tgg cag cac agg agc gcg act acc acg aac atc   1392
Ala Pro Thr Phe Ser Trp Gln His Arg Ser Ala Thr Thr Thr Asn Ile
    450                 455                 460 att gcg gct gac tcc atc act caa atc cct gcc gtt aag ggt cgc tcc   1440
Ile Ala Ala Asp Ser Ile Thr Gln Ile Pro Ala Val Lys Gly Arg Ser
465                 470                 475                 480 atc atc aac aat ggg aca gtg atc tcg gga ccg ggc ttc acc ggc ggt   1488
Ile Ile Asn Asn Gly Thr Val Ile Ser Gly Pro Gly Phe Thr Gly Gly
                485                 490                 495
```

-continued

| | |
|---|---|
| gac ctg gtg agg ctg tac aac gcg gac ttc aac atc aac aac agg gcg<br>Asp Leu Val Arg Leu Tyr Asn Ala Asp Phe Asn Ile Asn Asn Arg Ala<br>500             505             510 | 1536 |
| tac ctc gaa gtc ccg atc ttc ttc cag tcg ccc agc acg aac tat cgt<br>Tyr Leu Glu Val Pro Ile Phe Phe Gln Ser Pro Ser Thr Asn Tyr Arg<br>    515             520             525 | 1584 |
| gtc agg gtc cgg tac gcc tca acc tca tcc ctc ccg gtc gat gtg gtc<br>Val Arg Val Arg Tyr Ala Ser Thr Ser Ser Leu Pro Val Asp Val Val<br>530             535             540 | 1632 |
| ttc ggc aac atc agc cac ccg acc acg ttt ccg gct acc gcc cga tcc<br>Phe Gly Asn Ile Ser His Pro Thr Thr Phe Pro Ala Thr Ala Arg Ser<br>545             550             555             560 | 1680 |
| ctg gac aat ctg caa agc aac gat ttc ggc tac att gac att gcc ggg<br>Leu Asp Asn Leu Gln Ser Asn Asp Phe Gly Tyr Ile Asp Ile Ala Gly<br>            565             570             575 | 1728 |
| acg ttc ctc ccg agc ctc ggc cca tcc atc ggc atc cgg ccc atg ctc<br>Thr Phe Leu Pro Ser Leu Gly Pro Ser Ile Gly Ile Arg Pro Met Leu<br>        580             585             590 | 1776 |
| tcc acc atc aac ctg atc gtg gat cgg ttt gag ttc atc cca gtg aca<br>Ser Thr Ile Asn Leu Ile Val Asp Arg Phe Glu Phe Ile Pro Val Thr<br>    595             600             605 | 1824 |
| gcc act ttc gag gct gag tcc gac cta gag cgt gct cag aag gca gtc<br>Ala Thr Phe Glu Ala Glu Ser Asp Leu Glu Arg Ala Gln Lys Ala Val<br>610             615             620 | 1872 |
| aat gct ctg ttt acc tcc acc aat cag ctc ggc att aag acc gat gtg<br>Asn Ala Leu Phe Thr Ser Thr Asn Gln Leu Gly Ile Lys Thr Asp Val<br>625             630             635             640 | 1920 |
| acc gat tac cac att gac caa gtc tca aac ctc gtt gag tgc ctc tcg<br>Thr Asp Tyr His Ile Asp Gln Val Ser Asn Leu Val Glu Cys Leu Ser<br>            645             650             655 | 1968 |
| gat gag ttc tac ctt gat gag aag agg gag ctt tca gag aaa gtt aag<br>Asp Glu Phe Tyr Leu Asp Glu Lys Arg Glu Leu Ser Glu Lys Val Lys<br>        660             665             670 | 2016 |
| cac gct aag aga ctc tcg gac gaa cgc aat ctg ttg caa gat ccc aac<br>His Ala Lys Arg Leu Ser Asp Glu Arg Asn Leu Leu Gln Asp Pro Asn<br>    675             680             685 | 2064 |
| ttc aga ggg atc aac cgt cag cca gac cgg gga tgg cgc ggg tcc acg<br>Phe Arg Gly Ile Asn Arg Gln Pro Asp Arg Gly Trp Arg Gly Ser Thr<br>690             695             700 | 2112 |
| gac atc act atc cag ggc ggt gat gac gtc ttc aag gag aac tac gtg<br>Asp Ile Thr Ile Gln Gly Gly Asp Asp Val Phe Lys Glu Asn Tyr Val<br>705             710             715             720 | 2160 |
| acc ctg ccg ggc acc ttt gac gaa tgc tac ccc act tac ctc tac cag<br>Thr Leu Pro Gly Thr Phe Asp Glu Cys Tyr Pro Thr Tyr Leu Tyr Gln<br>            725             730             735 | 2208 |
| aag att gac gag tcc aag ctc aag gcg ttc aca cgc tac cag ctc agg<br>Lys Ile Asp Glu Ser Lys Leu Lys Ala Phe Thr Arg Tyr Gln Leu Arg<br>        740             745             750 | 2256 |
| ggt tac atc gag gac tcc caa gac ctg gaa atc tac ctg atc cgc tac<br>Gly Tyr Ile Glu Asp Ser Gln Asp Leu Glu Ile Tyr Leu Ile Arg Tyr<br>    755             760             765 | 2304 |
| aac gct aag cac gag act gtc aac gtg ccc ggc acc ggc agc ctg tgg<br>Asn Ala Lys His Glu Thr Val Asn Val Pro Gly Thr Gly Ser Leu Trp<br>770             775             780 | 2352 |
| ccc ttg tcc gct cag agc cca atc ggc aag tgc ggc gag ccc aac cgc<br>Pro Leu Ser Ala Gln Ser Pro Ile Gly Lys Cys Gly Glu Pro Asn Arg<br>785             790             795             800 | 2400 |
| tgc gcg ccc cac ctg gaa tgg aac ccc gac ctc gac tgt agc tgc cgc<br>Cys Ala Pro His Leu Glu Trp Asn Pro Asp Leu Asp Cys Ser Cys Arg | 2448 |

-continued

|   |   |   |   |   |   |   |   |   |   |   |   |   |   |   |   |   |
|---|---|---|---|---|---|---|---|---|---|---|---|---|---|---|---|---|
|   |   | 805 |   |   |   |   | 810 |   |   |   |   |   | 815 |   |   |   |
| gac | gga | gag | aag | tgc | gcg | cat | cac | tcc | cac | cac | ttc | agc | ctc | gac | atc | 2496 |
| Asp | Gly | Glu | Lys | Cys | Ala | His | His | Ser | His | His | Phe | Ser | Leu | Asp | Ile |   |
|   |   |   | 820 |   |   |   |   | 825 |   |   |   |   | 830 |   |   |   |
| gac | gtc | ggt | tgc | acc | gac | ctt | aac | gag | gat | ctg | ggc | gtt | tgg | gtg | atc | 2544 |
| Asp | Val | Gly | Cys | Thr | Asp | Leu | Asn | Glu | Asp | Leu | Gly | Val | Trp | Val | Ile |   |
|   |   | 835 |   |   |   |   | 840 |   |   |   |   | 845 |   |   |   |   |
| ttc | aag | atc | aag | act | cag | gac | ggc | cac | gcc | cgc | ctg | gga | aac | ctg | gag | 2592 |
| Phe | Lys | Ile | Lys | Thr | Gln | Asp | Gly | His | Ala | Arg | Leu | Gly | Asn | Leu | Glu |   |
| 850 |   |   |   |   | 855 |   |   |   |   | 860 |   |   |   |   |   |   |
| ttc | ctg | gag | gag | aag | ccc | ctc | gtt | ggc | gag | gcc | ctg | gcc | cgc | gtc | aag | 2640 |
| Phe | Leu | Glu | Glu | Lys | Pro | Leu | Val | Gly | Glu | Ala | Leu | Ala | Arg | Val | Lys |   |
| 865 |   |   |   | 870 |   |   |   |   | 875 |   |   |   |   | 880 |   |   |
| agg | gcc | gag | aag | aaa | tgg | cgc | gac | aag | cgc | gag | aag | ctg | gag | tgg | gag | 2688 |
| Arg | Ala | Glu | Lys | Lys | Trp | Arg | Asp | Lys | Arg | Glu | Lys | Leu | Glu | Trp | Glu |   |
|   |   |   |   | 885 |   |   |   |   | 890 |   |   |   |   | 895 |   |   |
| acc | aac | atc | gtg | tac | aag | gaa | gcg | aag | gag | tca | gtt | gac | gcc | ctg | ttc | 2736 |
| Thr | Asn | Ile | Val | Tyr | Lys | Glu | Ala | Lys | Glu | Ser | Val | Asp | Ala | Leu | Phe |   |
|   |   |   | 900 |   |   |   |   | 905 |   |   |   |   | 910 |   |   |   |
| gtc | aac | agc | cag | tac | gac | cag | ctc | cag | gca | gac | aca | aac | atc | gct | atg | 2784 |
| Val | Asn | Ser | Gln | Tyr | Asp | Gln | Leu | Gln | Ala | Asp | Thr | Asn | Ile | Ala | Met |   |
|   |   | 915 |   |   |   |   | 920 |   |   |   |   | 925 |   |   |   |   |
| atc | cat | gcg | gcc | gac | aag | cgc | gtc | cac | tcc | atc | cgc | gag | gcg | tac | ctg | 2832 |
| Ile | His | Ala | Ala | Asp | Lys | Arg | Val | His | Ser | Ile | Arg | Glu | Ala | Tyr | Leu |   |
| 930 |   |   |   |   | 935 |   |   |   |   | 940 |   |   |   |   |   |   |
| ccc | gag | ctg | tcc | gtc | atc | ccc | ggc | gtc | aac | gcc | gcg | atc | ttt | gag | gag | 2880 |
| Pro | Glu | Leu | Ser | Val | Ile | Pro | Gly | Val | Asn | Ala | Ala | Ile | Phe | Glu | Glu |   |
| 945 |   |   |   | 950 |   |   |   |   | 955 |   |   |   |   | 960 |   |   |
| ctg | gag | ggc | cgc | atc | ttc | acc | gcc | ttc | tcc | ctc | tac | gac | gca | cgc | aac | 2928 |
| Leu | Glu | Gly | Arg | Ile | Phe | Thr | Ala | Phe | Ser | Leu | Tyr | Asp | Ala | Arg | Asn |   |
|   |   |   |   | 965 |   |   |   |   | 970 |   |   |   |   | 975 |   |   |
| gtt | atc | aag | aat | ggc | gac | ttc | aac | aac | ggg | ctg | tcc | tgc | tgg | aat | gtc | 2976 |
| Val | Ile | Lys | Asn | Gly | Asp | Phe | Asn | Asn | Gly | Leu | Ser | Cys | Trp | Asn | Val |   |
|   |   |   | 980 |   |   |   |   | 985 |   |   |   |   | 990 |   |   |   |
| aag | ggc | cac | gtg | gac | gtc | gag | gag | cag | aac | aac | cag | cgc | tca | gtc | ctg | 3024 |
| Lys | Gly | His | Val | Asp | Val | Glu | Glu | Gln | Asn | Asn | Gln | Arg | Ser | Val | Leu |   |
|   |   | 995 |   |   |   |   | 1000 |   |   |   |   | 1005 |   |   |   |   |
| gtc | gtc | ccg | gag | tgg | gag | gcc | gaa | gtc | agc | cag | gaa | gtc | cgc | gtc |   | 3069 |
| Val | Val | Pro | Glu | Trp | Glu | Ala | Glu | Val | Ser | Gln | Glu | Val | Arg | Val |   |   |
|   | 1010 |   |   |   | 1015 |   |   |   |   | 1020 |   |   |   |   |   |   |
| tgc | cct | gga | cgc | ggg | tac | atc | ctg | cgc | gtc | act | gcc | tac | aag | gaa |   | 3114 |
| Cys | Pro | Gly | Arg | Gly | Tyr | Ile | Leu | Arg | Val | Thr | Ala | Tyr | Lys | Glu |   |   |
|   | 1025 |   |   |   | 1030 |   |   |   |   | 1035 |   |   |   |   |   |   |
| ggc | tac | gga | gag | ggc | tgc | gtc | acc | atc | cat | gag | atc | gaa | aac | aac |   | 3159 |
| Gly | Tyr | Gly | Glu | Gly | Cys | Val | Thr | Ile | His | Glu | Ile | Glu | Asn | Asn |   |   |
|   | 1040 |   |   |   | 1045 |   |   |   |   | 1050 |   |   |   |   |   |   |
| acg | gat | gag | ctt | aag | ttc | agc | aac | tgt | gtt | gaa | gag | gaa | atc | tac |   | 3204 |
| Thr | Asp | Glu | Leu | Lys | Phe | Ser | Asn | Cys | Val | Glu | Glu | Glu | Ile | Tyr |   |   |
|   | 1055 |   |   |   | 1060 |   |   |   |   | 1065 |   |   |   |   |   |   |
| ccg | aac | aac | acg | gtc | acc | tgc | aat | gat | tac | acc | gtc | aac | cag | gag |   | 3249 |
| Pro | Asn | Asn | Thr | Val | Thr | Cys | Asn | Asp | Tyr | Thr | Val | Asn | Gln | Glu |   |   |
|   | 1070 |   |   |   | 1075 |   |   |   |   | 1080 |   |   |   |   |   |   |
| gaa | tac | ggt | gga | gct | tac | acc | tcc | cgc | aac | agg | ggc | tac | aac | gag |   | 3294 |
| Glu | Tyr | Gly | Gly | Ala | Tyr | Thr | Ser | Arg | Asn | Arg | Gly | Tyr | Asn | Glu |   |   |
|   | 1085 |   |   |   | 1090 |   |   |   |   | 1095 |   |   |   |   |   |   |
| gca | ccc | tct | gtc | ccg | gcc | gac | tac | gct | tca | gtc | tac | gaa | gag | aag |   | 3339 |
| Ala | Pro | Ser | Val | Pro | Ala | Asp | Tyr | Ala | Ser | Val | Tyr | Glu | Glu | Lys |   |   |
|   | 1100 |   |   |   | 1105 |   |   |   |   | 1110 |   |   |   |   |   |   |
| tcg | tac | acc | gac | gga | cgc | aga | gag | aac | ccg | tgt | gag | ttc | aac | cgc |   | 3384 |

```
Ser Tyr Thr Asp Gly Arg Arg Glu Asn Pro Cys Glu Phe Asn Arg
    1115                1120                1125 ggc tac cgc gat tac acc ccg ctg cct gtc ggg tac gtc acc aaa      3429
Gly Tyr Arg Asp Tyr Thr Pro Leu Pro Val Gly Tyr Val Thr Lys
    1130                1135                1140 gag ctg gaa tac ttc cca gag acc gac aaa gtc tgg att gag atc      3474
Glu Leu Glu Tyr Phe Pro Glu Thr Asp Lys Val Trp Ile Glu Ile
    1145                1150                1155 ggc gag acc gag ggc acg ttc atc gtg gac tcc gtc gaa ctc ctt      3519
Gly Glu Thr Glu Gly Thr Phe Ile Val Asp Ser Val Glu Leu Leu
    1160                1165                1170 ctg atg gaa gag tga                                              3534
Leu Met Glu Glu
    1175

<210> SEQ ID NO 10
<211> LENGTH: 1177
<212> TYPE: PRT
<213> ORGANISM: Artificial Sequence
<220> FEATURE:
<223> OTHER INFORMATION: Synthetic Construct

<400> SEQUENCE: 10

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Ile Val Ser Gln Leu Thr Arg Glu Ile Tyr Thr Asn Pro Val
            260                 265                 270
```

```
Leu Glu Asn Phe Asp Gly Ser Phe Arg Gly Met Ala Gln Arg Ile Glu
            275                 280                 285

Gln Asn Ile Arg Gln Pro His Leu Met Asp Ile Leu Asn Ser Ile Thr
290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
                340                 345                 350

Thr Gly Leu Gly Ile Phe Arg Thr Leu Ser Ser Pro Leu Tyr Arg Arg
            355                 360                 365

Ile Ile Leu Gly Ser Gly Pro Asn Asn Gln Glu Leu Phe Val Leu Asp
370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
                420                 425                 430

His Val Thr Met Leu Ser Gln Ala Ala Gly Ala Val Tyr Thr Leu Arg
            435                 440                 445

Ala Pro Thr Phe Ser Trp Gln His Arg Ser Ala Thr Thr Thr Asn Ile
450                 455                 460

Ile Ala Ala Asp Ser Ile Thr Gln Ile Pro Ala Val Lys Gly Arg Ser
465                 470                 475                 480

Ile Ile Asn Asn Gly Thr Val Ile Ser Gly Pro Gly Phe Thr Gly Gly
                485                 490                 495

Asp Leu Val Arg Leu Tyr Asn Ala Asp Phe Asn Ile Asn Asn Arg Ala
                500                 505                 510

Tyr Leu Glu Val Pro Ile Phe Phe Gln Ser Pro Ser Thr Asn Tyr Arg
            515                 520                 525

Val Arg Val Arg Tyr Ala Ser Thr Ser Ser Leu Pro Val Asp Val Val
530                 535                 540

Phe Gly Asn Ile Ser His Pro Thr Thr Phe Pro Ala Thr Ala Arg Ser
545                 550                 555                 560

Leu Asp Asn Leu Gln Ser Asn Asp Phe Gly Tyr Ile Asp Ile Ala Gly
                565                 570                 575

Thr Phe Leu Pro Ser Leu Gly Pro Ser Ile Gly Ile Arg Pro Met Leu
                580                 585                 590

Ser Thr Ile Asn Leu Ile Val Asp Arg Phe Glu Phe Ile Pro Val Thr
            595                 600                 605

Ala Thr Phe Glu Ala Glu Ser Asp Leu Glu Arg Ala Gln Lys Ala Val
610                 615                 620

Asn Ala Leu Phe Thr Ser Thr Asn Gln Leu Gly Ile Lys Thr Asp Val
625                 630                 635                 640

Thr Asp Tyr His Ile Asp Gln Val Ser Asn Leu Val Glu Cys Leu Ser
                645                 650                 655

Asp Glu Phe Tyr Leu Asp Glu Lys Arg Glu Leu Ser Glu Lys Val Lys
                660                 665                 670

His Ala Lys Arg Leu Ser Asp Glu Arg Asn Leu Leu Gln Asp Pro Asn
            675                 680                 685
```

-continued

```
Phe Arg Gly Ile Asn Arg Gln Pro Asp Arg Gly Trp Arg Gly Ser Thr
690                 695                 700
Asp Ile Thr Ile Gln Gly Gly Asp Val Phe Lys Glu Asn Tyr Val
705                 710                 715                 720
Thr Leu Pro Gly Thr Phe Asp Glu Cys Tyr Pro Thr Tyr Leu Tyr Gln
                725                 730                 735
Lys Ile Asp Glu Ser Lys Leu Lys Ala Phe Thr Arg Tyr Gln Leu Arg
                740                 745                 750
Gly Tyr Ile Glu Asp Ser Gln Asp Leu Glu Ile Tyr Leu Ile Arg Tyr
                755                 760                 765
Asn Ala Lys His Glu Thr Val Asn Val Pro Gly Thr Gly Ser Leu Trp
770                 775                 780
Pro Leu Ser Ala Gln Ser Pro Ile Gly Lys Cys Gly Glu Pro Asn Arg
785                 790                 795                 800
Cys Ala Pro His Leu Glu Trp Asn Pro Asp Leu Asp Cys Ser Cys Arg
                805                 810                 815
Asp Gly Glu Lys Cys Ala His His Ser His Phe Ser Leu Asp Ile
                820                 825                 830
Asp Val Gly Cys Thr Asp Leu Asn Glu Asp Leu Gly Val Trp Val Ile
                835                 840                 845
Phe Lys Ile Lys Thr Gln Asp Gly His Ala Arg Leu Gly Asn Leu Glu
850                 855                 860
Phe Leu Glu Glu Lys Pro Leu Val Gly Glu Ala Leu Ala Arg Val Lys
865                 870                 875                 880
Arg Ala Glu Lys Lys Trp Arg Asp Lys Arg Glu Lys Leu Glu Trp Glu
                885                 890                 895
Thr Asn Ile Val Tyr Lys Glu Ala Lys Glu Ser Val Asp Ala Leu Phe
                900                 905                 910
Val Asn Ser Gln Tyr Asp Gln Leu Gln Ala Asp Thr Asn Ile Ala Met
                915                 920                 925
Ile His Ala Ala Asp Lys Arg Val His Ser Ile Arg Glu Ala Tyr Leu
930                 935                 940
Pro Glu Leu Ser Val Ile Pro Gly Val Asn Ala Ala Ile Phe Glu Glu
945                 950                 955                 960
Leu Glu Gly Arg Ile Phe Thr Ala Phe Ser Leu Tyr Asp Ala Arg Asn
                965                 970                 975
Val Ile Lys Asn Gly Asp Phe Asn Asn Gly Leu Ser Cys Trp Asn Val
                980                 985                 990
Lys Gly His Val Asp Val Glu Glu Gln Asn Asn Gln Arg Ser Val Leu
                995                 1000                1005
Val Val Pro Glu Trp Glu Ala Glu Val Ser Gln Glu Val Arg Val
1010                1015                1020
Cys Pro Gly Arg Gly Tyr Ile Leu Arg Val Thr Ala Tyr Lys Glu
1025                1030                1035
Gly Tyr Gly Glu Gly Cys Val Thr Ile His Glu Ile Glu Asn Asn
1040                1045                1050
Thr Asp Glu Leu Lys Phe Ser Asn Cys Val Glu Glu Ile Tyr
1055                1060                1065
Pro Asn Asn Thr Val Thr Cys Asn Asp Tyr Thr Val Asn Gln Glu
1070                1075                1080
Glu Tyr Gly Gly Ala Tyr Thr Ser Arg Asn Arg Gly Tyr Asn Glu
1085                1090                1095
Ala Pro Ser Val Pro Ala Asp Tyr Ala Ser Val Tyr Glu Glu Lys
```

```
                1100                 1105               1110

Ser  Tyr  Thr  Asp  Gly  Arg  Arg  Glu  Asn  Pro  Cys  Glu  Phe  Asn  Arg
          1115                 1120                      1125

Gly  Tyr  Arg  Asp  Tyr  Thr  Pro  Leu  Pro  Val  Gly  Tyr  Val  Thr  Lys
     1130                1135                     1140

Glu  Leu  Glu  Tyr  Phe  Pro  Glu  Thr  Asp  Lys  Val  Trp  Ile  Glu  Ile
     1145                1150                     1155

Gly  Glu  Thr  Glu  Gly  Thr  Phe  Ile  Val  Asp  Ser  Val  Glu  Leu  Leu
     1160                1165                     1170

Leu  Met  Glu  Glu
     1175

<210> SEQ ID NO 11
<211> LENGTH: 3534
<212> TYPE: DNA
<213> ORGANISM: Artificial Sequence
<220> FEATURE:
<223> OTHER INFORMATION: Fully Synthetic Nucleotide Sequence Encoding
      BCW 003 For Use In Plants
<220> FEATURE:
<221> NAME/KEY: CDS
<222> LOCATION: (1)..(3531)
<223> OTHER INFORMATION: BCW 003

<400> SEQUENCE: 11 atg gac aac aac ccg aac atc aac gag tgc atc ccc tac aac tgc ctc      48
Met Asp Asn Asn Pro Asn Ile Asn Glu Cys Ile Pro Tyr Asn Cys Leu
1               5                   10                  15 tcc aac ccg gag gtc gag gtg ctg ggc ggc gaa agg atc gag acc ggc      96
Ser Asn Pro Glu Val Glu Val Leu Gly Gly Glu Arg Ile Glu Thr Gly
                20                  25                  30 tac act ccc atc gac atc agc ctc agc ctg acc cag ttc ctg ctc tct     144
Tyr Thr Pro Ile Asp Ile Ser Leu Ser Leu Thr Gln Phe Leu Leu Ser
            35                  40                  45 gag ttc gtg ccc ggc gcg ggg ttc gtt ctc ggc ctg gtc gac atc atc     192
Glu Phe Val Pro Gly Ala Gly Phe Val Leu Gly Leu Val Asp Ile Ile
        50                  55                  60 tgg ggc atc ttc ggt ccg agc cag tgg gac gcc ttt ctc gtt cag att     240
Trp Gly Ile Phe Gly Pro Ser Gln Trp Asp Ala Phe Leu Val Gln Ile
65                  70                  75                  80 gag cag ctg atc aac cag cgc atc gag gag ttc gcc cgc aac cag gcg     288
Glu Gln Leu Ile Asn Gln Arg Ile Glu Glu Phe Ala Arg Asn Gln Ala
                85                  90                  95 atc tcc cgg ctg gag ggc ctc tcc aac ctg tac caa atc tac gcc gag     336
Ile Ser Arg Leu Glu Gly Leu Ser Asn Leu Tyr Gln Ile Tyr Ala Glu
            100                 105                 110 agc ttc cgg gag tgg gaa gcc gat ccg acc aac ccc gct ctc agg gag     384
Ser Phe Arg Glu Trp Glu Ala Asp Pro Thr Asn Pro Ala Leu Arg Glu
        115                 120                 125 gag atg cgg att cag ttc aac gac atg aac tcc gct ctc acg act gcc     432
Glu Met Arg Ile Gln Phe Asn Asp Met Asn Ser Ala Leu Thr Thr Ala
    130                 135                 140 atc cca ctc ctc gct gtg cag aac tac caa gtg ccg ctc ctg tcc gtg     480
Ile Pro Leu Leu Ala Val Gln Asn Tyr Gln Val Pro Leu Leu Ser Val
145                 150                 155                 160 tac gtg cag gcc gcc aat ctg cac ctc tcc gtc ctc cgg gac gtt agc     528
Tyr Val Gln Ala Ala Asn Leu His Leu Ser Val Leu Arg Asp Val Ser
                165                 170                 175 gtg ttc ggg cag cgc tgg ggc ttc gac gcc gct acc atc aac tcc cgt     576
Val Phe Gly Gln Arg Trp Gly Phe Asp Ala Ala Thr Ile Asn Ser Arg
            180                 185                 190
```

-continued

| | | |
|---|---|---|
| tac aac gat ctc act cgc ctc atc ggc aac tac acc gac tat gcc gtg<br>Tyr Asn Asp Leu Thr Arg Leu Ile Gly Asn Tyr Thr Asp Tyr Ala Val<br>                195                    200                    205 | 624 |

```
tac aac gat ctc act cgc ctc atc ggc aac tac acc gac tat gcc gtg      624
Tyr Asn Asp Leu Thr Arg Leu Ile Gly Asn Tyr Thr Asp Tyr Ala Val
            195                 200                 205 cgc tgg tac aac act ggt ctt gag aga gtc tgg ggc ccg gac agc cgc      672
Arg Trp Tyr Asn Thr Gly Leu Glu Arg Val Trp Gly Pro Asp Ser Arg
        210                 215                 220 gac tgg gtg cgc tac aac cag ttc cgg cgc gag ctg acc ctc acc gtg      720
Asp Trp Val Arg Tyr Asn Gln Phe Arg Arg Glu Leu Thr Leu Thr Val
225                 230                 235                 240 ctc gac atc gta gcc ctc ttt ccc aac tac gac tcc cgg cgc tac ccg      768
Leu Asp Ile Val Ala Leu Phe Pro Asn Tyr Asp Ser Arg Arg Tyr Pro
            245                 250                 255 att cgc acc gtc agc cag ctc acc agg gag atc tac acc aac cct gtg      816
Ile Arg Thr Val Ser Gln Leu Thr Arg Glu Ile Tyr Thr Asn Pro Val
        260                 265                 270 ctg gag aac ttc gac ggc tcc ttt cgc ggg atg gcc caa cgc ata gag      864
Leu Glu Asn Phe Asp Gly Ser Phe Arg Gly Met Ala Gln Arg Ile Glu
    275                 280                 285 cag aac atc cgc caa cct cat ctg atg gac atc ctt aat tct atc acc      912
Gln Asn Ile Arg Gln Pro His Leu Met Asp Ile Leu Asn Ser Ile Thr
290                 295                 300 atc tac act gac gtt cat cgc ggg ttt aac tac tgg tcg ggc cac caa      960
Ile Tyr Thr Asp Val His Arg Gly Phe Asn Tyr Trp Ser Gly His Gln
305                 310                 315                 320 atc act gcg tcg ccc gtt ggt ttc tcc ggc ccg gag ttc gcg ttc cct     1008
Ile Thr Ala Ser Pro Val Gly Phe Ser Gly Pro Glu Phe Ala Phe Pro
            325                 330                 335 ctg ttc gga aac gcg ggc aat gcc gct cca ccc gta ttg gtg agc ctg     1056
Leu Phe Gly Asn Ala Gly Asn Ala Ala Pro Pro Val Leu Val Ser Leu
        340                 345                 350 acc ggc ctc ggc atc ttc cgt aca ctg tct agc cct ctg tac aga agg     1104
Thr Gly Leu Gly Ile Phe Arg Thr Leu Ser Ser Pro Leu Tyr Arg Arg
    355                 360                 365 atc att ctt ggc agc ggt ccc aat aac cag gaa ctc ttc gtg ttg gac     1152
Ile Ile Leu Gly Ser Gly Pro Asn Asn Gln Glu Leu Phe Val Leu Asp
370                 375                 380 ggc acc gag ttc agc ttc gcc agt ctt acg acc aat ttg ccc tcc aca     1200
Gly Thr Glu Phe Ser Phe Ala Ser Leu Thr Thr Asn Leu Pro Ser Thr
385                 390                 395                 400 atc tat cgc cag cgc ggt act gtg gac tcc ctt gat gtg ata cca cct     1248
Ile Tyr Arg Gln Arg Gly Thr Val Asp Ser Leu Asp Val Ile Pro Pro
            405                 410                 415 cag gac aac tct gtc cca cct cgc gcc ggt ttc tcc cac cgc ctc agc     1296
Gln Asp Asn Ser Val Pro Pro Arg Ala Gly Phe Ser His Arg Leu Ser
        420                 425                 430 cac gtc act atg ctg agt cag gct gcg gga gcc gtg tac acc ctt cgg     1344
His Val Thr Met Leu Ser Gln Ala Ala Gly Ala Val Tyr Thr Leu Arg
    435                 440                 445 gct ccg acg ttt agc tgg cag cac agg agc gcg act acc acg aac atc     1392
Ala Pro Thr Phe Ser Trp Gln His Arg Ser Ala Thr Thr Thr Asn Ile
450                 455                 460 att gcg gct gac tcc atc act caa atc cct gcc gtt aag ggt cgc tcc     1440
Ile Ala Ala Asp Ser Ile Thr Gln Ile Pro Ala Val Lys Gly Arg Ser
465                 470                 475                 480 atc atc aac aat ggg aca gtg atc tcg gga ccg ggc ttc acc ggc ggt     1488
Ile Ile Asn Asn Gly Thr Val Ile Ser Gly Pro Gly Phe Thr Gly Gly
            485                 490                 495 gac ctg gtg agg ctg tac aac gcg gac ttc aac atc aac aac agg gcg     1536
Asp Leu Val Arg Leu Tyr Asn Ala Asp Phe Asn Ile Asn Asn Arg Ala
```

```
                500                 505                 510
tac ctc gaa gtc ccg atc ttc ttc cag tcg ccc agc acg aac tat cgt      1584
Tyr Leu Glu Val Pro Ile Phe Phe Gln Ser Pro Ser Thr Asn Tyr Arg
            515                 520                 525 gtc agg gtc cgg tac gcc tca acc tca tcc ctc ccg gtc gat gtg gtc      1632
Val Arg Val Arg Tyr Ala Ser Thr Ser Ser Leu Pro Val Asp Val Val
530                 535                 540 ttc ggc aac atc agc cac ccg acc acg ttt ccg gct acc gcc cga tcc      1680
Phe Gly Asn Ile Ser His Pro Thr Thr Phe Pro Ala Thr Ala Arg Ser
545                 550                 555                 560 ctg gac aat ctg caa agc aac gat ttc ggc tac att gac att gcc ggg      1728
Leu Asp Asn Leu Gln Ser Asn Asp Phe Gly Tyr Ile Asp Ile Ala Gly
            565                 570                 575 acg ttc ctc ccg agc ctc ggc cca tcc atc ggc atc cgg ccc atg ctc      1776
Thr Phe Leu Pro Ser Leu Gly Pro Ser Ile Gly Ile Arg Pro Met Leu
                580                 585                 590 tcc acc atc aac ctg atc gtg gat cgg ttt gag ttc atc cca gtg aca      1824
Ser Thr Ile Asn Leu Ile Val Asp Arg Phe Glu Phe Ile Pro Val Thr
                595                 600                 605 gcc act ttc gag gct gag tcc gac cta gag cgt gct cag aag gca gtc      1872
Ala Thr Phe Glu Ala Glu Ser Asp Leu Glu Arg Ala Gln Lys Ala Val
610                 615                 620 aat gct ctg ttt acc tcc acc aat cag ctc ggc att aag acc gat gtg      1920
Asn Ala Leu Phe Thr Ser Thr Asn Gln Leu Gly Ile Lys Thr Asp Val
625                 630                 635                 640 acc gat tac cac att gac caa gtc tca aac ctc gtt gag tgc ctc tcg      1968
Thr Asp Tyr His Ile Asp Gln Val Ser Asn Leu Val Glu Cys Leu Ser
            645                 650                 655 gat gag ttc tac ctt gat gag aag agg gag ctt tca gag aaa gtt aag      2016
Asp Glu Phe Tyr Leu Asp Glu Lys Arg Glu Leu Ser Glu Lys Val Lys
        660                 665                 670 cac gct aag aga ctc tcg gac gaa cgc aat ctg ttg caa gat ccc aac      2064
His Ala Lys Arg Leu Ser Asp Glu Arg Asn Leu Leu Gln Asp Pro Asn
            675                 680                 685 ttc aga ggg atc aac cgt cag cca gac cgg gga tgg cgc ggg tcc acg      2112
Phe Arg Gly Ile Asn Arg Gln Pro Asp Arg Gly Trp Arg Gly Ser Thr
        690                 695                 700 gac atc act atc cag ggc ggt gat gac gtc ttc aag gag aac tac gtg      2160
Asp Ile Thr Ile Gln Gly Gly Asp Asp Val Phe Lys Glu Asn Tyr Val
705                 710                 715                 720 acc ctg ccg ggc acc ttt gac gaa tgc tac ccc act tac ctc tac cag      2208
Thr Leu Pro Gly Thr Phe Asp Glu Cys Tyr Pro Thr Tyr Leu Tyr Gln
                725                 730                 735 aag att gac gag tcc aag ctc aag gcg ttc aca cgc tac cag ctc agg      2256
Lys Ile Asp Glu Ser Lys Leu Lys Ala Phe Thr Arg Tyr Gln Leu Arg
            740                 745                 750 ggt tac atc gag gac tcc caa gac ctg gaa atc tac ctg atc cgc tac      2304
Gly Tyr Ile Glu Asp Ser Gln Asp Leu Glu Ile Tyr Leu Ile Arg Tyr
        755                 760                 765 aac gct aag cac gag act gtc aac gtg ccc ggc acc ggc agc ctg tgg      2352
Asn Ala Lys His Glu Thr Val Asn Val Pro Gly Thr Gly Ser Leu Trp
        770                 775                 780 ccc ttg tcc gct cag agc cca atc ggc aag tgc ggc gag ccc aac cgc      2400
Pro Leu Ser Ala Gln Ser Pro Ile Gly Lys Cys Gly Glu Pro Asn Arg
785                 790                 795                 800 tgc gcg ccc cac ctg gaa tgg aac ccc gac ctc gac tgt agc tgc cgc      2448
Cys Ala Pro His Leu Glu Trp Asn Pro Asp Leu Asp Cys Ser Cys Arg
                805                 810                 815 gac gga gag aag tgc gcg cat cac tcc cac cac ttc agc ctc gac atc      2496
```

|  |  |  |  |  |  |  |  |  |  |  |  |  |  |  |
|---|---|---|---|---|---|---|---|---|---|---|---|---|---|---|
| Asp | Gly | Glu | Lys<br>820 | Cys | Ala | His | His<br>825 | Ser | His | His | Phe | Ser | Leu<br>830 | Asp | Ile |

| gac | gtc | ggt | tgc | acc | gac | ctt | aac | gag | gat | ctg | ggc | gtt | tgg | gtg | atc | 2544 |
|---|---|---|---|---|---|---|---|---|---|---|---|---|---|---|---|---|
| Asp | Val | Gly<br>835 | Cys | Thr | Asp | Leu | Asn<br>840 | Glu | Asp | Leu | Gly | Val<br>845 | Trp | Val | Ile | |

| ttc | aag | atc | aag | act | cag | gac | ggc | cac | gcc | cgc | ctg | gga | aac | ctg | gag | 2592 |
|---|---|---|---|---|---|---|---|---|---|---|---|---|---|---|---|---|
| Phe | Lys | Ile | Lys<br>850 | Thr | Gln | Asp | Gly | His<br>855 | Ala | Arg | Leu | Gly | Asn<br>860 | Leu | Glu | |

| ttc | ctg | gag | gag | aag | ccc | ctc | gtt | ggc | gag | gcc | ctg | gcc | cgc | gtc | aag | 2640 |
|---|---|---|---|---|---|---|---|---|---|---|---|---|---|---|---|---|
| Phe<br>865 | Leu | Glu | Glu | Lys | Pro<br>870 | Leu | Val | Gly | Glu | Ala<br>875 | Leu | Ala | Arg | Val | Lys<br>880 | |

| agg | gcc | gag | aag | aaa | tgg | cgc | gac | aag | cgc | gag | aag | ctg | gag | tgg | gag | 2688 |
|---|---|---|---|---|---|---|---|---|---|---|---|---|---|---|---|---|
| Arg | Ala | Glu | Lys | Lys<br>885 | Trp | Arg | Asp | Lys | Arg<br>890 | Glu | Lys | Leu | Glu | Trp<br>895 | Glu | |

| acc | aac | atc | gtg | tac | aag | gaa | gcg | aag | gag | tca | gtt | gac | gcc | ctg | ttc | 2736 |
|---|---|---|---|---|---|---|---|---|---|---|---|---|---|---|---|---|
| Thr | Asn | Ile | Val<br>900 | Tyr | Lys | Glu | Ala | Lys<br>905 | Glu | Ser | Val | Asp | Ala<br>910 | Leu | Phe | |

| gtc | aac | agc | cag | tac | gac | cag | ctc | cag | gca | gac | aca | aac | atc | gct | atg | 2784 |
|---|---|---|---|---|---|---|---|---|---|---|---|---|---|---|---|---|
| Val | Asn | Ser<br>915 | Gln | Tyr | Asp | Gln | Leu<br>920 | Gln | Ala | Asp | Thr | Asn<br>925 | Ile | Ala | Met | |

| atc | cat | gcg | gcc | gac | aag | cgc | gtc | cac | tcc | atc | cgc | gag | gcg | tac | ctg | 2832 |
|---|---|---|---|---|---|---|---|---|---|---|---|---|---|---|---|---|
| Ile<br>930 | His | Ala | Ala | Asp | Lys<br>935 | Arg | Val | His | Ser | Ile<br>940 | Arg | Glu | Ala | Tyr | Leu | |

| ccc | gag | ctg | tcc | gtc | atc | ccc | ggc | gtc | aac | gcc | gcg | atc | ttt | gag | gag | 2880 |
|---|---|---|---|---|---|---|---|---|---|---|---|---|---|---|---|---|
| Pro<br>945 | Glu | Leu | Ser | Val | Ile<br>950 | Pro | Gly | Val | Asn | Ala<br>955 | Ala | Ile | Phe | Glu | Glu<br>960 | |

| ctg | gag | ggc | cgc | atc | ttc | acc | gcc | ttc | tcc | ctc | tac | gac | gca | cgc | aac | 2928 |
|---|---|---|---|---|---|---|---|---|---|---|---|---|---|---|---|---|
| Leu | Glu | Gly | Arg | Ile<br>965 | Phe | Thr | Ala | Phe | Ser<br>970 | Leu | Tyr | Asp | Ala | Arg<br>975 | Asn | |

| gtt | atc | aag | aat | ggc | gac | ttc | aac | aac | ggg | ctg | tcc | tgc | tgg | aat | gtc | 2976 |
|---|---|---|---|---|---|---|---|---|---|---|---|---|---|---|---|---|
| Val | Ile | Lys | Asn<br>980 | Gly | Asp | Phe | Asn | Asn<br>985 | Gly | Leu | Ser | Cys | Trp<br>990 | Asn | Val | |

| aag | ggc | cac | gtg | gac | gtc | gag | gag | cag | aac | aac | cag | cgc | tca | gtc | ctg | 3024 |
|---|---|---|---|---|---|---|---|---|---|---|---|---|---|---|---|---|
| Lys | Gly | His<br>995 | Val | Asp | Val | Glu | Glu<br>1000 | Gln | Asn | Asn | Gln | Arg<br>1005 | Ser | Val | Leu | |

| gtc | gtc | ccg | gag | tgg | gag | gcc | gaa | gtc | agc | cag | gaa | gtc | cgc | gtc | 3069 |
|---|---|---|---|---|---|---|---|---|---|---|---|---|---|---|---|
| Val | Val<br>1010 | Pro | Glu | Trp | Glu | Ala<br>1015 | Glu | Val | Ser | Gln | Glu<br>1020 | Val | Arg | Val | |

| tgc | cct | gga | cgc | ggg | tac | atc | ctg | cgc | gtc | act | gcc | tac | aag | gaa | 3114 |
|---|---|---|---|---|---|---|---|---|---|---|---|---|---|---|---|
| Cys<br>1025 | Pro | Gly | Arg | Gly | Tyr<br>1030 | Ile | Leu | Arg | Val | Thr<br>1035 | Ala | Tyr | Lys | Glu | |

| ggc | tac | gga | gag | ggc | tgc | gtc | acc | atc | cat | gag | atc | gaa | aac | aac | 3159 |
|---|---|---|---|---|---|---|---|---|---|---|---|---|---|---|---|
| Gly | Tyr<br>1040 | Gly | Glu | Gly | Cys | Val<br>1045 | Thr | Ile | His | Glu | Ile<br>1050 | Glu | Asn | Asn | |

| acg | gat | gag | ctt | aag | ttc | agc | aac | tgt | gtt | gaa | gag | gaa | atc | tac | 3204 |
|---|---|---|---|---|---|---|---|---|---|---|---|---|---|---|---|
| Thr | Asp<br>1055 | Glu | Leu | Lys | Phe | Ser<br>1060 | Asn | Cys | Val | Glu | Glu<br>1065 | Glu | Ile | Tyr | |

| ccg | aac | aac | acg | gtc | acc | tgc | aat | gat | tac | acc | gtc | aac | cag | gag | 3249 |
|---|---|---|---|---|---|---|---|---|---|---|---|---|---|---|---|
| Pro | Asn<br>1070 | Asn | Thr | Val | Thr | Cys<br>1075 | Asn | Asp | Tyr | Thr | Val<br>1080 | Asn | Gln | Glu | |

| gaa | tac | ggt | gga | gct | tac | acc | tcc | cgc | aac | agg | ggc | tac | aac | gag | 3294 |
|---|---|---|---|---|---|---|---|---|---|---|---|---|---|---|---|
| Glu | Tyr<br>1085 | Gly | Gly | Ala | Tyr | Thr<br>1090 | Ser | Arg | Asn | Arg | Gly<br>1095 | Tyr | Asn | Glu | |

| gca | ccc | tct | gtc | ccg | gcc | gac | tac | gct | tca | gtc | tac | gaa | gag | aag | 3339 |
|---|---|---|---|---|---|---|---|---|---|---|---|---|---|---|---|
| Ala | Pro<br>1100 | Ser | Val | Pro | Ala | Asp<br>1105 | Tyr | Ala | Ser | Val | Tyr<br>1110 | Glu | Glu | Lys | |

| tcg | tac | acc | gac | gga | cgc | aga | gag | aac | ccg | tgt | gag | ttc | aac | cgc | 3384 |
|---|---|---|---|---|---|---|---|---|---|---|---|---|---|---|---|
| Ser | Tyr<br>1115 | Thr | Asp | Gly | Arg | Arg<br>1120 | Glu | Asn | Pro | Cys | Glu<br>1125 | Phe | Asn | Arg | |

```
ggc  tac  cgc  gat  tac  acc  ccg  ctg  cct  gtc  ggg  tac  gtc  acc  aaa           3429
Gly  Tyr  Arg  Asp  Tyr  Thr  Pro  Leu  Pro  Val  Gly  Tyr  Val  Thr  Lys
1130                     1135                     1140 gag  ctg  gaa  tac  ttc  cca  gag  acc  gac  aaa  gtc  tgg  att  gag  atc           3474
Glu  Leu  Glu  Tyr  Phe  Pro  Glu  Thr  Asp  Lys  Val  Trp  Ile  Glu  Ile
     1145                     1150                     1155 ggc  gag  acc  gag  ggc  acg  ttc  atc  gtg  gac  tcc  gtc  gaa  ctc  ctt           3519
Gly  Glu  Thr  Glu  Gly  Thr  Phe  Ile  Val  Asp  Ser  Val  Glu  Leu  Leu
1160                     1165                     1170 ctg  atg  gaa  gag  tga                                                             3534
Leu  Met  Glu  Glu
     1175
```

<210> SEQ ID NO 12
<211> LENGTH: 1177
<212> TYPE: PRT
<213> ORGANISM: Artificial Sequence
<220> FEATURE:
<223> OTHER INFORMATION: Synthetic Construct

<400> SEQUENCE: 12

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285
```

```
Gln Asn Ile Arg Gln Pro His Leu Met Asp Ile Leu Asn Ser Ile Thr
    290                 295                 300
Ile Tyr Thr Asp Val His Arg Gly Phe Asn Tyr Trp Ser Gly His Gln
305                 310                 315                 320
Ile Thr Ala Ser Pro Val Gly Phe Ser Gly Pro Glu Phe Ala Phe Pro
                325                 330                 335
Leu Phe Gly Asn Ala Gly Asn Ala Ala Pro Val Leu Val Ser Leu
            340                 345                 350
Thr Gly Leu Gly Ile Phe Arg Thr Leu Ser Ser Pro Leu Tyr Arg Arg
        355                 360                 365
Ile Ile Leu Gly Ser Gly Pro Asn Asn Gln Glu Leu Phe Val Leu Asp
370                 375                 380
Gly Thr Glu Phe Ser Phe Ala Ser Leu Thr Thr Asn Leu Pro Ser Thr
385                 390                 395                 400
Ile Tyr Arg Gln Arg Gly Thr Val Asp Ser Leu Asp Val Ile Pro Pro
                405                 410                 415
Gln Asp Asn Ser Val Pro Pro Arg Ala Gly Phe Ser His Arg Leu Ser
            420                 425                 430
His Val Thr Met Leu Ser Gln Ala Ala Gly Ala Val Tyr Thr Leu Arg
        435                 440                 445
Ala Pro Thr Phe Ser Trp Gln His Arg Ser Ala Thr Thr Thr Asn Ile
450                 455                 460
Ile Ala Ala Asp Ser Ile Thr Gln Ile Pro Ala Val Lys Gly Arg Ser
465                 470                 475                 480
Ile Ile Asn Asn Gly Thr Val Ile Ser Gly Pro Gly Phe Thr Gly Gly
                485                 490                 495
Asp Leu Val Arg Leu Tyr Asn Ala Asp Phe Asn Ile Asn Asn Arg Ala
            500                 505                 510
Tyr Leu Glu Val Pro Ile Phe Phe Gln Ser Pro Ser Thr Asn Tyr Arg
        515                 520                 525
Val Arg Val Arg Tyr Ala Ser Thr Ser Ser Leu Pro Val Asp Val Val
530                 535                 540
Phe Gly Asn Ile Ser His Pro Thr Thr Phe Pro Ala Thr Ala Arg Ser
545                 550                 555                 560
Leu Asp Asn Leu Gln Ser Asn Asp Phe Gly Tyr Ile Asp Ile Ala Gly
                565                 570                 575
Thr Phe Leu Pro Ser Leu Gly Pro Ser Ile Gly Ile Arg Pro Met Leu
            580                 585                 590
Ser Thr Ile Asn Leu Ile Val Asp Arg Phe Glu Phe Ile Pro Val Thr
        595                 600                 605
Ala Thr Phe Glu Ala Glu Ser Asp Leu Glu Arg Ala Gln Lys Ala Val
610                 615                 620
Asn Ala Leu Phe Thr Ser Thr Asn Gln Leu Gly Ile Lys Thr Asp Val
625                 630                 635                 640
Thr Asp Tyr His Ile Asp Gln Val Ser Asn Leu Val Glu Cys Leu Ser
                645                 650                 655
Asp Glu Phe Tyr Leu Asp Glu Lys Arg Glu Leu Ser Glu Lys Val Lys
            660                 665                 670
His Ala Lys Arg Leu Ser Asp Glu Arg Asn Leu Leu Gln Asp Pro Asn
        675                 680                 685
Phe Arg Gly Ile Asn Arg Gln Pro Asp Arg Gly Trp Arg Gly Ser Thr
690                 695                 700
```

```
Asp Ile Thr Ile Gln Gly Gly Asp Asp Val Phe Lys Glu Asn Tyr Val
705                 710                 715                 720

Thr Leu Pro Gly Thr Phe Asp Glu Cys Tyr Pro Thr Tyr Leu Tyr Gln
            725                 730                 735

Lys Ile Asp Glu Ser Lys Leu Lys Ala Phe Thr Arg Tyr Gln Leu Arg
                740                 745                 750

Gly Tyr Ile Glu Asp Ser Gln Asp Leu Glu Ile Tyr Leu Ile Arg Tyr
            755                 760                 765

Asn Ala Lys His Glu Thr Val Asn Val Pro Gly Thr Gly Ser Leu Trp
770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
            805                 810                 815

Asp Gly Glu Lys Cys Ala His His Ser His His Phe Ser Leu Asp Ile
                820                 825                 830

Asp Val Gly Cys Thr Asp Leu Asn Glu Asp Leu Gly Val Trp Val Ile
            835                 840                 845

Phe Lys Ile Lys Thr Gln Asp Gly His Ala Arg Leu Gly Asn Leu Glu
850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Gln Leu Gln Ala Asp Thr Asn Ile Ala Met
            915                 920                 925

Ile His Ala Ala Asp Lys Arg Val His Ser Ile Arg Glu Ala Tyr Leu
930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn Gln Arg Ser Val Leu
                995                 1000                1005

Val Val Pro Glu Trp Glu Ala Glu Val Ser Gln Glu Val Arg Val
            1010                1015                1020

Cys Pro Gly Arg Gly Tyr Ile Leu Arg Val Thr Ala Tyr Lys Glu
            1025                1030                1035

Gly Tyr Gly Glu Gly Cys Val Thr Ile His Glu Ile Glu Asn Asn
            1040                1045                1050

Thr Asp Glu Leu Lys Phe Ser Asn Cys Val Glu Glu Glu Ile Tyr
            1055                1060                1065

Pro Asn Asn Thr Val Thr Cys Asn Asp Tyr Thr Val Asn Gln Glu
            1070                1075                1080

Glu Tyr Gly Gly Ala Tyr Thr Ser Arg Asn Arg Gly Tyr Asn Glu
            1085                1090                1095

Ala Pro Ser Val Pro Ala Asp Tyr Ala Ser Val Tyr Glu Glu Lys
            1100                1105                1110

Ser Tyr Thr Asp Gly Arg Arg Glu Asn Pro Cys Glu Phe Asn Arg
```

-continued

```
        1115                    1120                    1125

Gly Tyr Arg Asp Tyr Thr Pro Leu Pro Val Gly Tyr Val Thr Lys
        1130                    1135            1140

Glu Leu Glu Tyr Phe Pro Glu Thr Asp Lys Val Trp Ile Glu Ile
        1145                    1150            1155

Gly Glu Thr Glu Gly Thr Phe Ile Val Asp Ser Val Glu Leu Leu
        1160                    1165            1170

Leu Met Glu Glu
        1175
```